United States Patent
Tolani et al.

(10) Patent No.: US 9,522,743 B1
(45) Date of Patent: Dec. 20, 2016

(54) PARACHUTE DATA RECORDER SYSTEM

(71) Applicant: Intelligent Automation, Inc., Rockville, MD (US)

(72) Inventors: Devendra Kumar Tolani, Germantown, MD (US); Michael J. Clark, Germantown, MD (US); Jakob P. Henriksson, I, Hyattsville, MD (US); Jyotirmaya Nanda, Gaithersburg, MD (US); Chujen Lin, North Potomac, MD (US)

(73) Assignee: Intelligent Automation, Inc., Rockville, MD (US)

( * ) Notice: Subject to any disclaimer, the term of this patent is extended or adjusted under 35 U.S.C. 154(b) by 47 days.

(21) Appl. No.: 14/541,234

(22) Filed: Nov. 14, 2014

Related U.S. Application Data

(60) Provisional application No. 61/906,580, filed on Nov. 20, 2013.

(51) Int. Cl.
| | |
|---|---|
| *G08B 1/08* | (2006.01) |
| *B64D 47/00* | (2006.01) |
| *G01D 9/28* | (2006.01) |
| *B64D 21/00* | (2006.01) |
| *B64D 23/00* | (2006.01) |
| *A61B 5/0205* | (2006.01) |
| *A61B 5/021* | (2006.01) |
| *A61B 5/024* | (2006.01) |

(52) U.S. Cl.
CPC ........... *B64D 47/00* (2013.01); *A61B 5/02055* (2013.01); *B64D 21/00* (2013.01); *B64D 23/00* (2013.01); *G01D 9/28* (2013.01); *A61B 5/021* (2013.01); *A61B 5/024* (2013.01)

(58) Field of Classification Search
CPC ........ B64D 17/00; H04B 1/034; H04B 1/3827
See application file for complete search history.

(56) References Cited

U.S. PATENT DOCUMENTS

| | | | |
|---|---|---|---|
| 8,200,379 B2* | 6/2012 | Manfredi | B64D 25/00 244/122 A |
| 2002/0166925 A1* | 11/2002 | Benney | B64D 17/00 244/142 |
| 2005/0067816 A1* | 3/2005 | Buckman | A41D 13/018 280/730.1 |
| 2005/0127243 A1* | 6/2005 | Voronka | B64D 17/56 244/150 |
| 2007/0233382 A1* | 10/2007 | Preston | G01C 21/20 701/500 |

(Continued)

Primary Examiner — Emily C Terrell
(74) Attorney, Agent, or Firm — Faegre Baker Daniels LLP

(57) ABSTRACT

A parachute data recorder system is provided that includes a housing, the housing having a seal for resistance to moisture and environmental impact; a plurality of sensors mounted in the housing, including an accelerometer, an altimeter, a gyrometer, and a GPS; a microprocessor mounted in the housing for recording and processing data from the sensors; a wireless connection unit mounted in the housing for transmitting data in the microprocessor; and an electronic connection port. The parachute data recorder system may further include a second accelerometer, one of the accelerometers being a low-g accelerometer and the other being a high-g accelerometer. The initiation of recording can be started by stress or strain inducement from parachute deployment.

19 Claims, 47 Drawing Sheets

(56) References Cited

U.S. PATENT DOCUMENTS

| | | | | |
|---|---|---|---|---|
| 2010/0318294 A1* | 12/2010 | Rosing | ............... | G01C 21/165 |
| | | | | 701/500 |
| 2014/0031703 A1* | 1/2014 | Rayner | ............. | A61B 5/02055 |
| | | | | 600/484 |
| 2014/0070931 A1* | 3/2014 | Savaresi | ............ | B60R 21/0132 |
| | | | | 340/436 |
| 2014/0292510 A1* | 10/2014 | Cholhan | ............ | G08B 25/016 |
| | | | | 340/539.13 |

\* cited by examiner

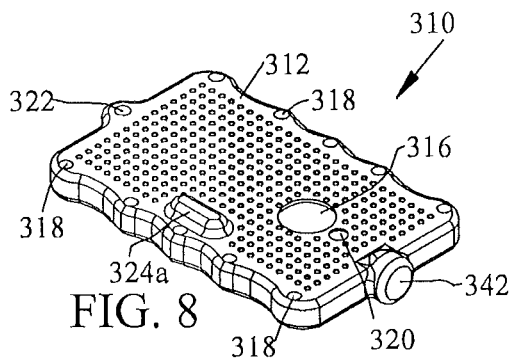
FIG. 8
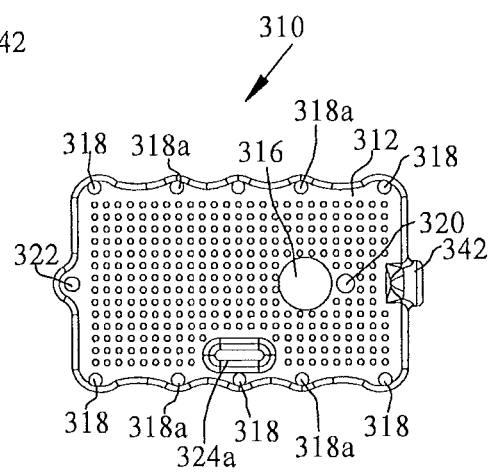
FIG. 9
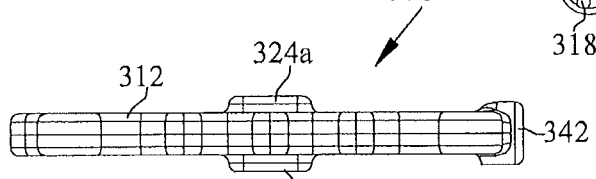
FIG. 10
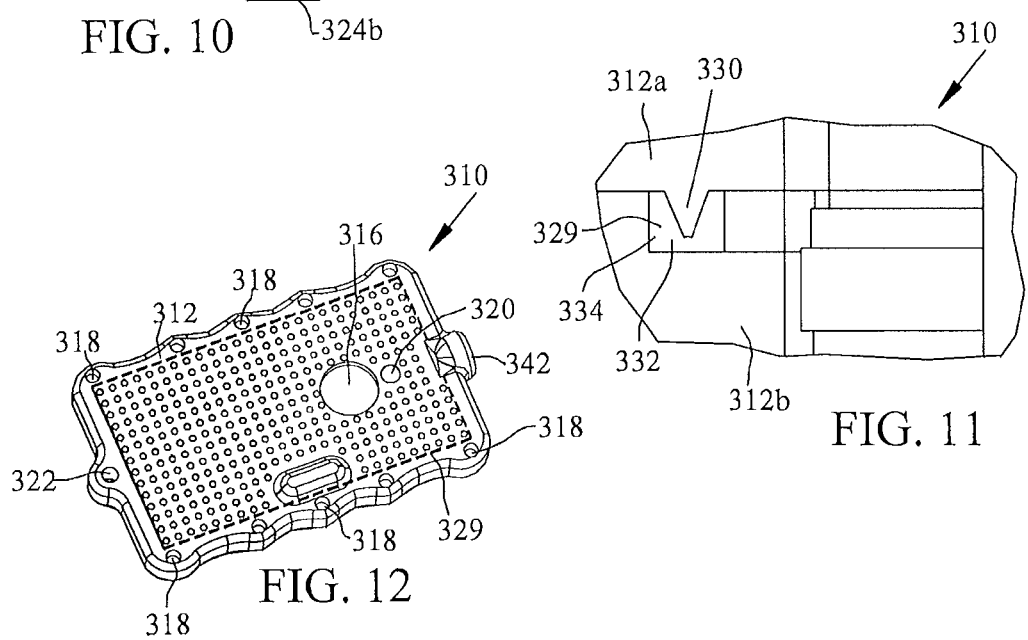
FIG. 11
FIG. 12

PARACHUTE DATA RECORDER   HOME SESSION      SYNC     ADMIN CONTACT           ADMIN
USERS                                                                    +NEW USER
CLICK ON THE USER NAME TO EDIT THE USER INFORMATION

| USER NAME | FIRST NAME | LAST NAME |
|---|---|---|
| USER 1 | XXXA | YYYA |
| USER 2 | XXXB | YYYB |
| USER 3 | XXXC | YYYC |
| USER 4 | XXXD | YYYD |
| USER 5 | XXXE | YYYE |
| USER 6 | XXXF | YYYF |
| USER 7 | XXXG | YYYG |
| USER 8 | XXXH | YYYH |
| USER 9 | XXXI | YYYI |
| USER 10 | XXXJ | YYYJ |

PARACHUTE DATA RECORDER  HOME  SESSIONS  SYNC  ADMIN  CONTACT

<ALL USERS

CREATE NEW USER

USER NAME  [USER NAME]

PASSWORD  [PASSWORD]

RE-TYPE PASSWORD  [RE-TYPE PASSWORD]

FIRST NAME  [FIRST NAME]
*PROVIDING A FIRST NAME IS OPTIONAL*

LAST NAME  [LAST NAME]
*PROVIDING A LAST NAME IS OPTIONAL*

ROLES  ROLE_ADMIN
       ROLE_JUMPER
       ROLE_JUMP_MASTER
       ROLE_QUARTER_MASTER

[CREATE]

PARACHUTE DATA RECORDER   HOME SESSION        SYNC      ADMIN CONTACT        ADMIN

SESSION
TIME 2013-03-01            13:00 - 2013-03-01  19:00
VIEW PERFORMANCE DATA      ASSOCIATE JUMPS
SESSION NAME

| FLORIDA HAHO |

THE SESSION NAME IS OPTIONAL

JUMP MASTER

| JUMPER X1 |

THE JUMPER MASTER FOR THIS SESSION

JUMPERS

- o   / JUMPER XX1
- o   / JUMPER XX2

WARNING: JUMPER XX2 HAS NO ASSIGNED PARACHUTE

- o   / JUMPER XX3

WARNING: JUMPER XX3 HAS NO ASSIGNED PARACHUTE

| + ADD JUMPER |

FIG. 39

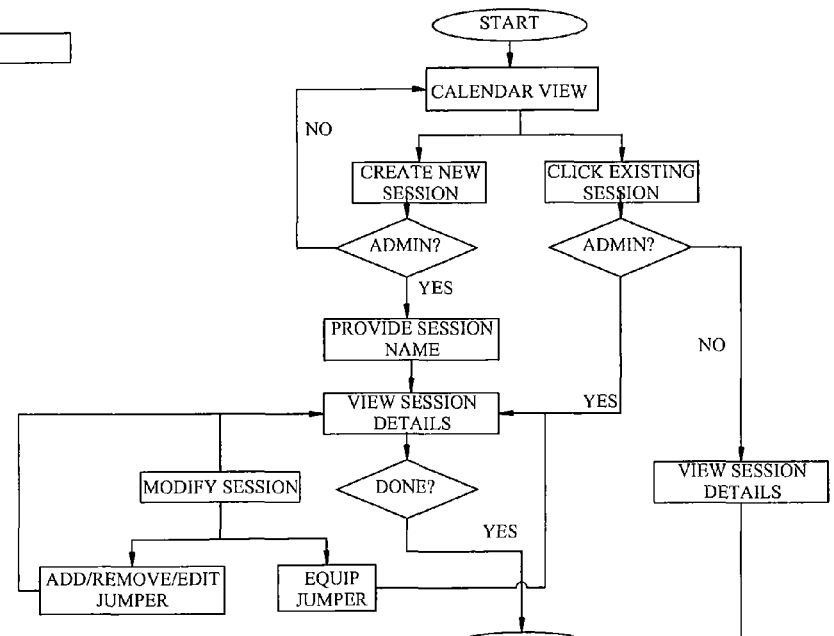

FIG. 40

PARACHUTE DATA RECORDER   HOME   SESSIONS   SYNC   ADMIN   CONTACT

CONFIGURING DEVICE 001

MODIFY THE CONFIGURATION AND THEN CLICK "SAVE CHANGES"

SENSORS

☑ ALTIMETER
  ENABLE ALTIMETER SENSOR

☑ GYRO
  ENABLE GYRO AND LC SENSOR

☑ LowG ACCELERATOR
  ENABLE LOW-G ACCELEROMETER

☑ HighG ACCELERATOR
  ENABLE High-G ACCELEROMETER

☐ GPS
  ENABLE GPS ACCELEROMETER

FIG. 44

| ▶DATA_ACCEL_HIGH_G | ▶DATA_GYRO | ▶DATA_ALTIMETER | ▶DATA_TEMPERATURE | ▶DATA_GYRO |
|---|---|---|---|---|
| O id INT | O id INT | O id INT | O id INT | O id INT |
| O pdr VARCHAR(4) | O pdr VARCHAR(4) | O pdr VARCHAR(4) | O pdr VARCHAR(4) | O pdr VARCHAR(4) |
| O day DATE | O day DATE | O day DATE | O day DATE | O day DATE |
| O jump INT | O jump INT | O jump INT | O jump INT | O jump INT |
| O seconds DECIMAL | O seconds DECIMAL | O seconds DECIMAL | O seconds DECIMAL | O seconds DECIMAL |
| O x DECIMAL | O x DECIMAL | O pressure DECIMAL | O TEMPERATURE DECIMAL | O lat DECIMAL |
| O y DECIMAL | O y DECIMAL | INDEXES ▲ | INDEXES ▲ | O lon DECIMAL |
| O z DECIMAL | O z DECIMAL | | | O height DOUBLE |
| INDEXES ▲ | INDEXES ▲ | | | INDEXES ▲ |

FIG. 47

PARACHUTE DATA RECORDER   HOME  SESSIONS   SYNC   ADMIN  CONTACT

JOBS
ID:1, PROGRESS: 5%, STATUS: RUNNING

[ DELETE ALL JOBS ]

| | A | B | C | D | E | F | G | H | I |
|---|---|---|---|---|---|---|---|---|---|
| 1 | WEIGHT (lb) | MASS (sl) | Vi (ft/s) | DELTA t (s) | DRAG INTEGRAL | F aver(horiz) eq. 4a. in lbs | F aver(vert) eq. 4b. in lbs | F peak (horiz) eq. 7a or 8a in lbs | F peak (vert) eq. 7b or 8b in lbs |
| 2 | | | | | | | | | |
| 3 | 220 | 6.838669568 | 159 | 2.5 | 0.4 | 434.9393845 | 654.9393845 | 1067.34861 | 1307.348461 |
| 4 | 220 | 6.838669568 | 166 | 2.5 | 0.4 | 454.0876593 | 674.0876593 | 1135.219148 | 1355.219148 |
| 5 | 220 | 6.838669568 | 159 | 2.5 | 0.5 | 434.9393845 | 654.9393845 | 869.878769 | 1089.878769 |
| 6 | 220 | 6.838669568 | 166 | 2.5 | 0.5 | 454.0876593 | 674.0876593 | 908.1753186 | 1128.175319 |
| 7 | | | | | | | | | |
| 8 | | | | | | | | | |
| 9 | | is input | | | | | | | |
| 10 | | is calculated | | | | | | | |
| 11 | | is calculated | | | | | | | |
| 12 | | | | | | | | | |
| 13 | | | | | | | | | |

FIG. 58

| | A | B | C | D | E | F | G | H | I |
|---|---|---|---|---|---|---|---|---|---|
| 1 | WEIGHT (lb) | MASS (sl) | Vi (ft/s) | DELTA t (s) | DRAG INTEGRAL | | a aver(vert) eq. 4b. in lbs | | a peak (vert) eq. 7b or 8b in lbs |
| 2 | | | | | | | | | |
| 3 | 220 | 6.838669568 | 159 | 2.5 | 0.4 | | 1.976997202 | | 4.942493006 |
| 4 | 220 | 6.838669568 | 166 | 2.5 | 0.4 | | 2.064034815 | | 5.160087038 |
| 5 | 220 | 6.838669568 | 159 | 2.5 | 0.5 | | 1.976997202 | | 3.953994405 |
| 6 | 220 | 6.838669568 | 166 | 2.5 | 0.5 | | 2.064034815 | | 4.12806963 |
| 7 | | | | | | | | | |
| 8 | | | | | | | | | |
| 9 | | is input | | | | | | | |
| 10 | | is calculated | | | | | | | |
| 11 | | is calculated | | | | | | | |
| 12 | | | | | | | | | |
| 13 | | | | | | | | | |

| J | K | L | M | N | O | P | Q | R |
|---|---|---|---|---|---|---|---|---|
| ALT(m) | ALT(ft) | PRESSURE (mbar) STANDARD ATM | dP OVER dH | Vff m/s | Vff (ft/s) | Vff (mph) | | |
| 1000 | 3280 | 898.7272111 | -0.109037448 | -48.5677 | -159.302 | -108.369 | A | 2.25577E-05 |
| 1500 | 4920 | 845.5337981 | -0.103781343 | -51.0275 | -167.37 | -113.857 | B | 5.257075184 |
| 2000 | 6560 | 794.9190572 | -0.098721316 | -56.6429 | -175.949 | -119.693 | dP OVER dT | 5.2957 |
| 2500 | 8200 | 746.7862396 | -0.09385224 | -56.4259 | -185.077 | -125.903 | | |
| 3000 | 9840 | 701.0411412 | -.089169063 | -59.3894 | -194.797 | -132.515 | | |
FIG. 66
| P | Q | R | S | T | U | V | W | X |
|---|---|---|---|---|---|---|---|---|
| ALT(m) | ALT(ft) | PRESSURE (mbar) STANDARD ATM | dP OVER dH | Vff m/s | Vff (ft/s) | Vff (mph) | | |
| 1000 | 3280 | 898.7272111 | -0.109037448 | -50.6248 | -166.049 | -112.959 | A | 2.25577E-05 |
| 1500 | 4920 | 845.5337981 | -0.103781343 | -53.1888 | -174.459 | -118.68 | B | 5.257075184 |
| 2000 | 6560 | 794.9190572 | -0.098721316 | -55.915 | -183.401 | -124.763 | dP OVER dT | 5.52 |
| 2500 | 8200 | 746.7862396 | -0.09385224 | -58.8159 | -192.916 | -131.235 | | |
| 3000 | 9840 | 701.0411412 | -.089169063 | -61.9049 | -203.048 | -138.128 | | |
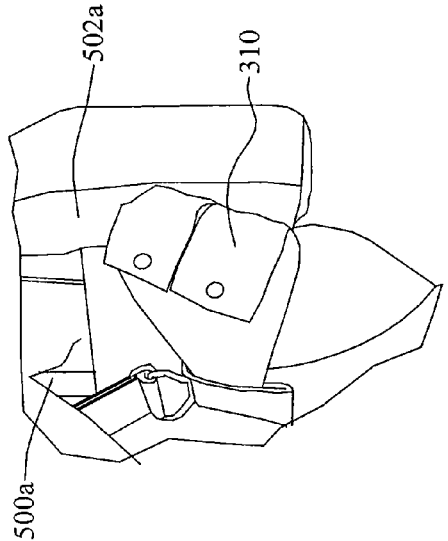
FIG. 67A
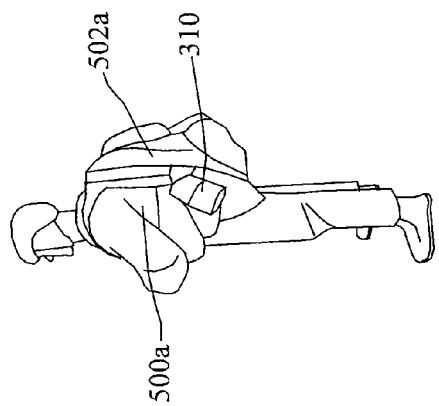
FIG. 67

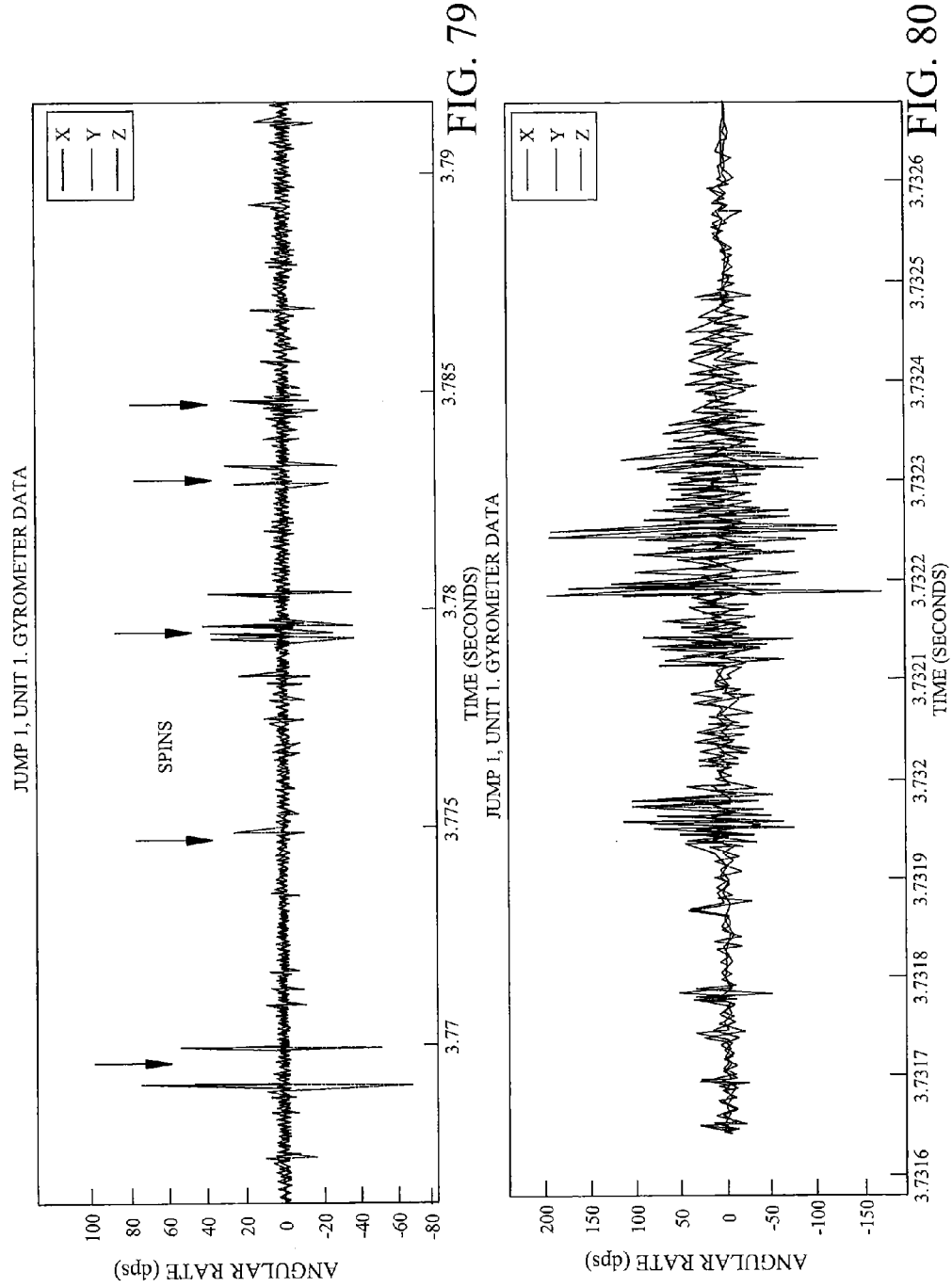

PARACHUTE DATA RECORDER SYSTEM

This is a nonprovisional application claiming priority from U.S. provisional patent application Ser. No. 61/906,580, filed on Nov. 20, 2013, the entirety of which is incorporated by reference herein.

This invention was made with government support under Contract No. W91CRB-11-C-0021, Natick Soldier Research Development and Engineering Center, U.S. Army Research Development and Engineering Command. The government has certain rights in the invention.

BACKGROUND OF THE INVENTION

This invention relates to a system end device for recording data related to parachute training, testing, and evaluation, and in particular, to a system and device including motion-based sensors and other equipment capable of monitoring, recording and analyzing 3-axis acceleration, pressure, temperature, 3-axis angular velocity and Global Positioning System (GPS) location.

For air drop operations, both personal and cargo, tracking performance and usage data is necessary for routine maintenance and training, as well as incident investigations. Currently, this data tracking, which is limited to parachute usage and packing frequency, is handled by manually recording usage information in logbooks and used to determine maintenance and repacking schedules. Furthermore, these manually recorded data are prone to human error and are labor intensive. Of course, if parachute systems are left in service too long, this increases the safety risk. For incident investigations, only usage data and eye witness accounts are available. For example, information relating to parachute performance such as the opening shock force, descent rate, etc., can be very valuable especially in instances resulting in a parachute failure, and wherein if injury or a fatality results. Heretofore, there has been no consistent means of data collection whereby parameters such as deployment time, location, altitude, and opening shock force can be made available. If this data collection management system could be automated, it would be more efficient, more accurate and more comprehensive.

Therefore, an object of the invention is to provide an innovative Parachute Data Recorder (PDR) system. It is also an object of the invention to provide an automatic data recording device whereby both routine performance and usage parameters critical to an accident investigation can be reliably collected upon parachute deployment. Another object of the invention is that the PDR be portable, network ready, sensor rich, and capable of recording and managing data for parachuting applications. It is a further object of the invention that the device for the PDR system is designed as a retro-fit for attachment to personnel and/or cargo being parachuted and have a relatively small, lightweight, and low-power design that would allow for easy integration into existing parachute systems without altering safety characteristics. A further object of the invention that the air drop system's main components, harnessing container should serve as the database key to allow for flexibility between reserve and main parachutes.

A further object of the invention that data recording may be initiated upon parachute deployment by means of stress/strain inducement and capture time, location, altitude, and opening shock. This further object depends on pressure sensing technology that can be used to record altitude, while integration with GPS technology can record both location and provide a real-time stamp for data logging. Additionally, the system may provide an interface to allow the parachute rigger to record packing information including a method to record the parachute rigger's identification (i.e., signature via smart card technology or other electronic means). A further object is that the system could maintain the current state of the art and capture all current logbook information for the life of the parachute system as well as parachute performance data.

Another object of the invention is that the system be compatible with both static line and military free-fall parachute systems and that information for each jump be capable of being broken down into primary and secondary needs. Primary needs represent data collected without significant modifications to the parachute system, which for a static line include: parachute packed by and date and serial number; reserve packed by and date and serial number; jumper identification; aircraft type; date of jump; DZ location; parachute harness type; equipment configuration; jumper weight; and jump master inspection by. Secondary needs represent data collection requiring additional equipment development to be attached to the parachute system or jumper, which for a static line include: opening shock profile; rate of descent profile; and altitude.

The free-fall primary needs include: altitude at exit-user input; altitude at opening-user input; main parachute type and serial number; reserve parachute type and serial number; parachute harness type and serial number; automatic activation device type and serial number; oxygen equipment type and serial number; parachute packed by and date; reserve packed by and date; jumper identification; aircraft type; aircraft speed-user input; date of jump; DZ location; equipment configuration; altimeter type and setting; and jump master inspection by. The secondary needs for free-fall include: altitude at exit-automated; altitude at opening-automated; and measured opening shock.

A further object of the invention is that data can be retrieved via a wired USB interface or wirelessly (WiFi) and can be used using a handheld device with a web-based graphical user interface. It is also an object of the invention that the PDR components of the parachute system, including but not limited to a riser, the parachute canopy, oxygen, altimeter, etc., may be scanned wherein identification numbers associated with each of the parameters could be tracked by the PDR and a software package is provided wherein the database of each component, the jumper, the rigger, etc., may be monitored, recorded, and observed. This allows clear tracking of inventory and uses of the equipment for reliable analysis and life usage calculations. It is a further object of the invention to link the scanned items to a database including factory recall alerts or maintenance action requests to easily identify which equipment has been recalled or is in need of maintenance. An additional object of the invention is that the database include alerts to the rigger when certain components have exceed their design specifications, for instance, such as temperature, excessive shock, or exceeded the maximum number of jumps. It is a further object of the invention that the PDR may be able to incorporate health monitoring features, such as pulse, blood pressure, temperature, etc., which may be maintained in a database to monitor health parameters and identify potential health issues of the jumpers.

SUMMARY OF THE INVENTION

In one embodiment of the invention, a parachute data recorder system is provided that includes a housing, the housing having a seal for resistance to moisture and environmental impact; a plurality of sensors mounted in the housing, including an accelerometer, an altimeter, a gyrometer, and a GPS; a microprocessor mounted in the housing for recording and processing data from the sensors; a wireless connection unit mounted in the housing for transmitting data in the microprocessor; and an electronic connection port.

The parachute data recorder system may further include a second accelerometer, one of the accelerometers being a low-g accelerometer and the other being a high-g accelerometer. The initiation of recording can be started by stress or strain inducement from parachute deployment.

The parachute data recorder system may also include an interface configured to support recording information including a parachute rigger's identification, date and serial number for both the primary and secondary parachutes as well as jumper identification, aircraft type, date of jump, jump location, parachute harness type, equipment configuration, jumper weight, and jump master inspection.

The housing may include a front cover and a rear cover mounted together with fasteners received in threaded apertures or threaded inserts in the apertures, and one or more apertures is devoid of a fastener for receiving tie-offs to mount the housing. The parachute data recorder system may also include a sealed cap covering the electronic connection port.

The parachute data recorder system may further include a main control button including a tactile switch wherein pressing and holding the main button enables the unit and wherein a subsequent quick push activates recording capabilities or pressing and holding the button disables the unit.

The parachute data recorder system may further include an LED indicator, including four unique states including an idol status showing as a solid first color, a recording status wherein the first color is blinking, a busy status showing as a solid second color, and a solid third color indicating an unrecordable system error.

The parachute data recorder system may further including a strict power sequential sensing and initialization routine in inquiry whether a main button is pressed wherein recording is enabled or if USB is attached to said electronic connection port, to connect the unit to a mass-storage device driver or enable wireless connection.

The parachute data recorder system can also calculate average and peak riser forces sustained during jumps.

In another aspect of the invention a method of recording dynamic and static data for parachute jumps is provided including the steps of: providing a sensor and recording system including a sealed housing, sensors including a GPS, a low-g accelerometer, a high-g accelerometer, an altimeter, and a gyrometer, and a microprocessor; imputing data related to a jump to be performed including a parachute rigger's identification, a date a parachute was packed, serial number of the parachute; activating the unit prior to a jump; the sensors recording dynamic jumping data relative to a parachute jump.

The method of recording dynamic and static data for parachute jumps may further include the steps of selecting and holding a main control switch to power the system on, and quickly pushing the main control switch to activate recording capabilities. The method may further include the step of pressing and holding the main control switch to disable the system.

The method of recording dynamic and static data for parachute jumps may further include the step of initiating recording of sensor data by stress or strain inducement from parachute deployment.

The method of recording dynamic and static data for parachute jumps may also further include the steps of providing an interface to the sensor and recording system and recording information related to a parachute riggers identification, packing date, and serial number for both primary and secondary parachutes, jumper identification, aircraft type, date of jump, jump location, parachute harness type, equipment configuration, jump plate, or jump master inspection.

The method of recording dynamic and static data for parachute jumps may also include the steps of providing front and rear covers mounted together with fasteners and apertures, leaving one or more apertures devoid of a fastener, and using the apertures as tie-offs to mount the housing.

The method of recording dynamic and static data for parachute jumps can additionally include the steps of providing an LED indicator, and indicating the unique states of the system using said LED indicator, wherein an idol status shows as a solid first color, a recording status shows with the first color blinking, a busy status shows as a solid second color, and an unrecoverable system error shows as a solid third color.

The method of recording dynamic and static data for parachute jumps may also include the steps of calculating average and peak rise of forces sustained during jumps, and transforming coordinate and axes of the sensor and recording system to other referenced frames coinciding with a jumper's center of gravity and on the ground.

The method of recording dynamic and static data for parachute jumps may also include the step of providing a wireless connection and web-based graphical user interface for tracking of inventory and uses of parachute equipment and for downloading data from the recording system.

BRIEF DESCRIPTION OF THE DRAWINGS

The above-mentioned and other features and objects of this invention and the manner of obtaining them will become more apparent, and the invention itself will be better understood by reference to the following description of embodiments of the present invention taken in conjunction with the accompanying drawings, wherein:

FIG. 8 is a perspective view of another embodiment of PDR device in accordance with the subject invention;

FIG. 9 is a plan view of the PDR device of FIG. 8;

FIG. 10 is a side view of the PDR device of FIG. 8;

FIG. 11 is a partial cross-sectional view showing a tongue and groove closure for the PDR device of FIG. 8;

FIG. 12 is a plan view of the PDR device of FIG. 8 showing an interlocking groove and seal;

FIG. 37 is a screen shot showing how a new user is added on the PDR software;

FIG. 38 is a screen shot showing calendars in which the GUI allows users to plan jump sessions;

FIG. 39 is details for an example jump session;

FIG. 40 is a block flow diagram for creating, viewing and editing jump sessions;

FIG. 44 is a screen shot for configuring the PDR device;

FIG. 47 shows table definitions for low G acceleration, gyrometer, altimeter, temperature, and GPS;

FIG. 48 is a screen shot showing the progress of performance data importing from the PDR device;

FIG. 57 shows riser force calculations for a test jump;

FIG. 58 shows deceleration for test jumps;

FIG. 66 shows sample calculations of fall rate comparisons during two different test jumps;

FIG. 67 is a side view of another parachutist having the PDR device located in a pouch on the left side of the parachute;

FIG. 67A is an enlarged view of the pouch holding the PDR device from FIG. 67;

FIG. 79 is filtered gyrometer data output from the PDR device during the middle portion of the jump associated with FIG. 78;

FIG. 80 is a graph of gyrometer data output for the jump associated with FIG. 78 during the free-fall and deployment/inflation part of the jump;

Figure 1:
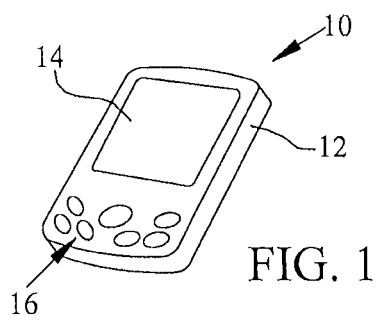
FIG. 1 is a perspective view of one embodiment of a parachute data analyzer device in accordance with subject invention.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates embodiments of the invention, and such exemplifications are not to be construed as limiting the scope of the invention in any manner.

DETAILED DESCRIPTION OF EMBODIMENTS OF THE INVENTION

For the purpose of promoting an understanding of the principles of the invention, reference will now be made to the embodiments illustrated in the drawings, which are described below. It will nevertheless be understood that no limitation of the scope of the invention is thereby intended. The invention includes any alterations and further modifications in the illustrated devices and described methods and further applications of the principles of the invention, which would normally occur to one skilled in the art to which the invention relates.

A parachute data recorder system and device is provided having a relatively small size and low power consumption that can be readily integrated into existing parachute systems without altering their safety characteristics.

Now referring to FIG. 1, one embodiment of a Parachute Data Analyzer (PDA) device is shown, generally indicated as 10. PDA device 10 includes a case or housing 12, a display 14, and a plurality of control buttons, generally indicated as 16. The PDA can be used to receive downloaded data from a PDR and analyze/display the data.

Figure 2:
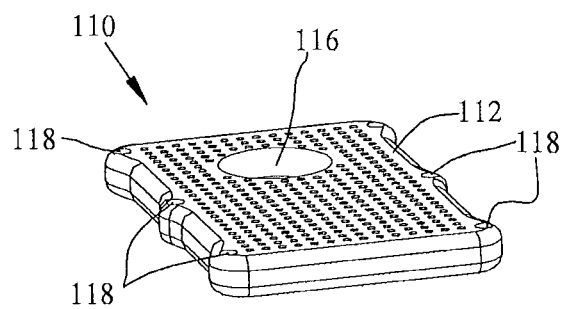
FIG. 2 is a perspective view of one embodiment of a PDR device in accordance with the subject invention.
Figure 3:
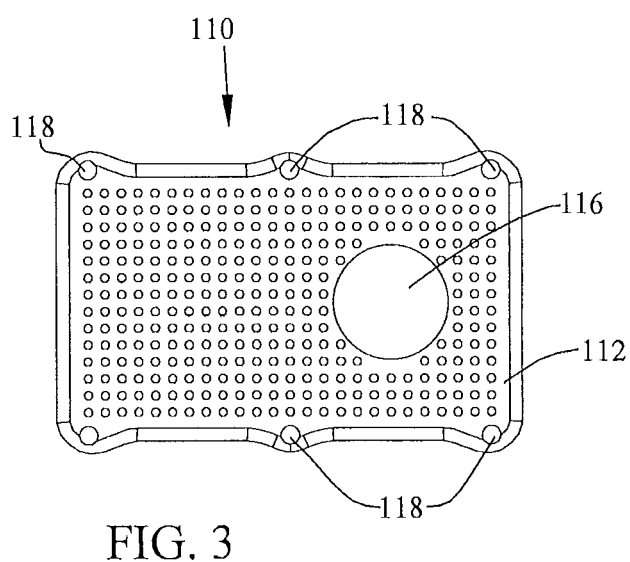
FIG. 3 is a plan view of the PDR of FIG. 2.
Figure 4:
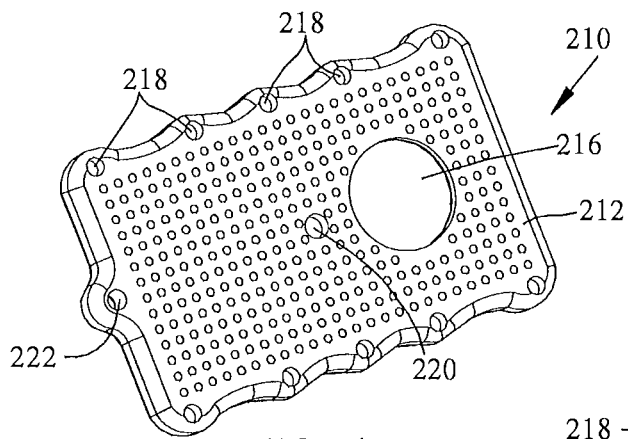
FIG. 4 is a perspective view of another embodiment of a PDR device in accordance with the subject invention.

Now referring to FIGS. 2-3, one embodiment of the packaging design for a PDR device is shown, generally indicated as 110. PDR device 110 includes a case or housing 112, a main control button 116, and apertures with threaded fasteners 118 for securely holding case 112, which may be supplied with front and back covers, together.

Figure 5:
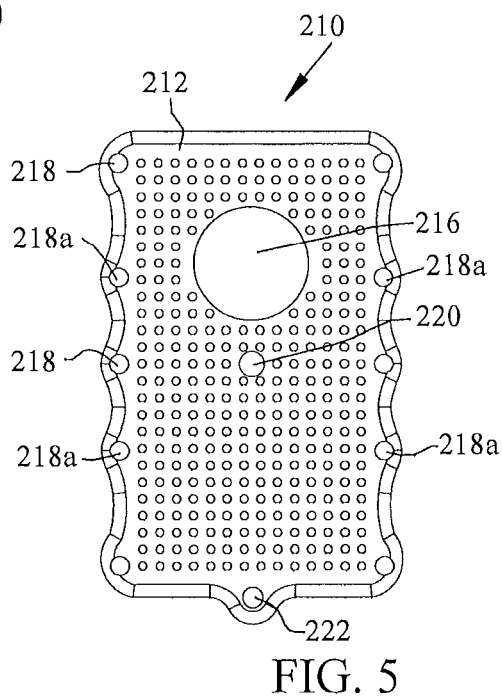
FIG. 5 is a plan view of the front side of the PDR device of FIG. 4.

Now referring to FIGS. 4-7, an alternate embodiment PDR device is shown, generally indicated as 210. PDR device 210 includes a case or housing 212, a main control button 216, and a plurality of apertures with threaded fasteners 218, which may be used to hold front and rear covers making up case 212, together. Device 210 also includes an LED light 220, and a bottom aperture or tie off point 222. A parachute chord may be tied and/or weaved through the tie off points for added security of the device. As best shown in FIG. 5, some threaded fasteners may be left out of apertures 218 to provide additional tie off points 218a along the sides of case 212. The embodiment of PDR device 210 shown in FIG. 5 includes four side tie off points 218a. Case 212 should be manufactured from a material having sufficient strength, lightness of weight and that is compatible with the electronics and wireless systems contained therein. Case 212 may be made from Nylon 6.

Figure 6:
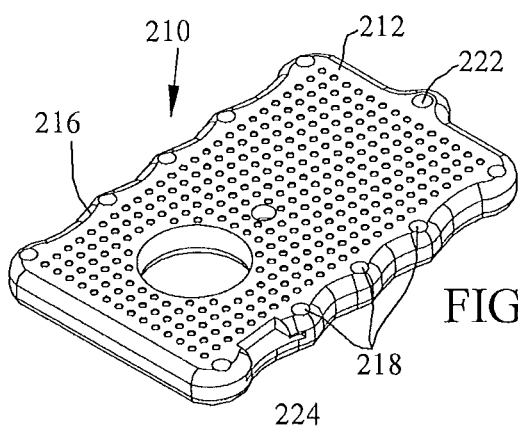
FIG. 6 is a perspective bottom view of the PDR device of FIG. 4.
Figure 7:
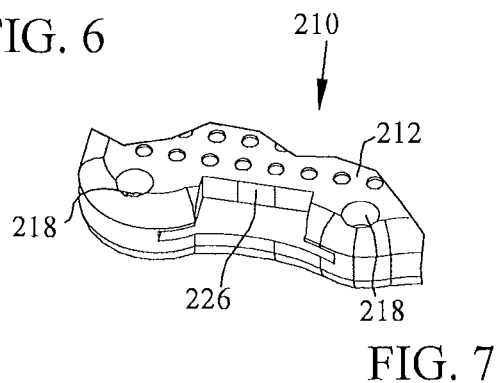
FIG. 7 is an enlarged view showing a USB port of the PDR device of FIG. 4.
Figure 13:
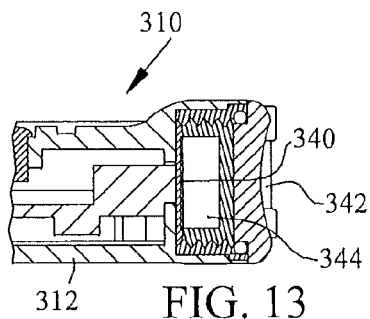
FIG. 13 is an enlarged partial cross-sectional view of the USB port and sealing cap of the PDR device of FIG. 8.
Figure 14:
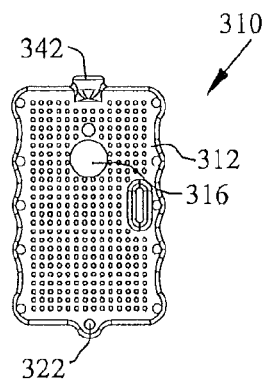
FIG. 14 is another plan view of the PDR device of FIG. 8.

It should be appreciated that preferably PDR device 210 is water tight and appropriate sealing means may be employed. Referring to FIGS. 6 and 7, an access door 224 may also be provided in case 210. The access door may be removed by removing an applicable threaded fastener 218. When access door 224 is removed, (as best shown in FIG. 7), a USB port 226 is exposed. It should be appreciated that an appropriate seal may be used around access door 224 to provide a water tight compartment in which USB port 226 is located.

Figure 15:
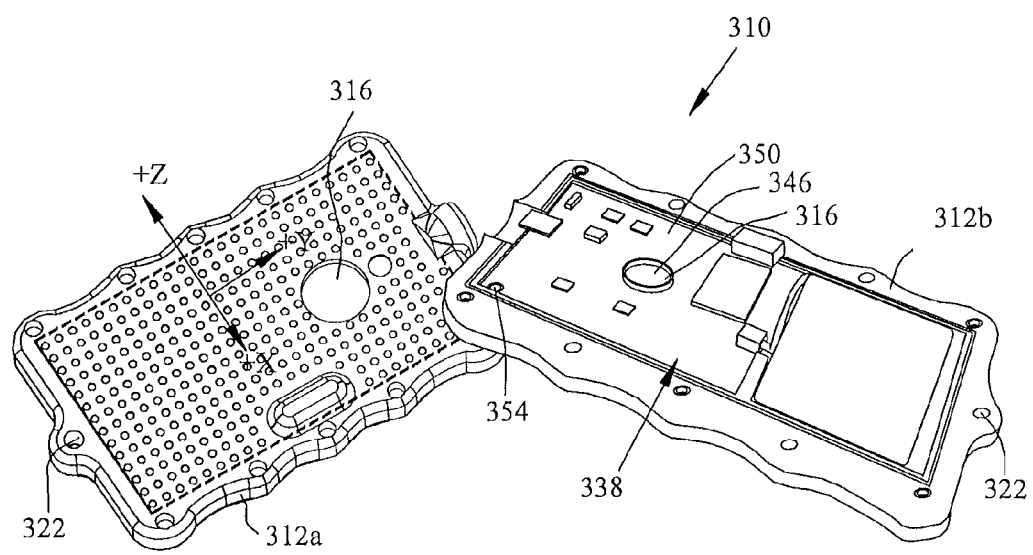
FIG. 15 is a perspective view of the PDR device of FIG. 8 with a cover of the case removed.

Now referring to FIGS. 8-20, yet another alternate embodiment PDR is shown, generally indicated as 310. As with PDR device embodiments 110 and 210, PDR device 310 includes a case or housing 312, a main control button 316 and a plurality of apertures with threaded fasteners 318 for securely holding case 312 together, which includes a front cover 312a and a rear cover 312b (FIG. 15). PDR device 310 also includes an LED 320 and a lower aperture or tie off point 322. Also, as with PDR device 210, PDR device 310 may include side tie off points 318a where threaded fasteners may be omitted (as best shown in FIG. 9).

As indicated that it is desirous to maintain the PDR devices with as low a profile as possible. Accordingly, housing 312 has as low a profile while still meeting specifications. Housing 312 includes two slightly higher areas than the remainder of the housing. One is a localized protrusion or protruding area 324a on front cover 312a, and the other protrusion or protruding area 324b is in rear cover 312b.

Figure 20:
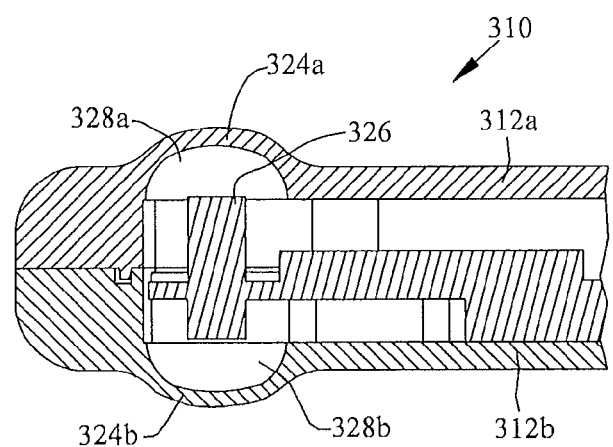
FIG. 20 is a cross-sectional view through protruding pocketed areas of the PDR device of FIG. 8 where the antenna is located.

Referring to FIG. 20, protrusions 324a and 324b surround an antenna 326 and extend outwardly beyond the remainder of case 312 to provide pocketed areas 328a and 328b around antenna 326 to ensure that the enclosure is at least 0.25 inches away from any area in the case for proper functionality. Structural integrity of case 312 is maintained in protrusions 324a and 324b.

In one embodiment of a prototype produced in accordance with the design of PDR device 310, the maximum length of the device was 4.9 inches, the maximum width was 2.91 inches, and the height was a maximum of 0.8 inches.

As it is desirable that device 310 maintain water tightness to a depth of five meters for duration of at least 30 minutes, a seal 329 is provided (FIGS. 11 and 12) that includes a V-shaped tongue 330 extending from front cover 312a, which is received in a square groove 332 in rear cover 312b. Groove 332 may be filled with a sealant 334, such as RTV silicon, whereby the front cover 312a and rear cover 312b are pressed together and sealed and ultimately screwed down tight using apertures and fasteners 318 to provide a suitable seal. Seal 329 makes a smooth path around the flat plane of the enclosure (FIGS. 11 and 12). It should be noted, that the groove is also formed around a USB opening to ensure sealing in that area as well. It is not necessary to seal the screws as they are located to the exterior of seal 329 and do not affect the internal waterproof integrity except by firmly securing the two halves together.

It should be appreciated that a material such as Nylon 6 for construction of housing 312 assures that the housing is EMI/RF transparent and also provides adequate strength while maintaining transparency for wireless devices and antennae to function properly. It was found that no EMI shielding was required nor EMI paint on the inside of the enclosure to maintain the wireless transparency.

Covers 212a and 212b may be attached with an internal ball and chain system (not shown) with a revolving mount to allow the cover to be screwed together and apart without binding the chain. This would assure that the covers do not become lost or separated from one another when unscrewed but still allows adequate access to an internal USB connector. A prototype of the case with the aforementioned design met testing requirements in accordance with the water tightness criteria to a depth of five meters for a duration of at least 30 minutes.

Figure 16:
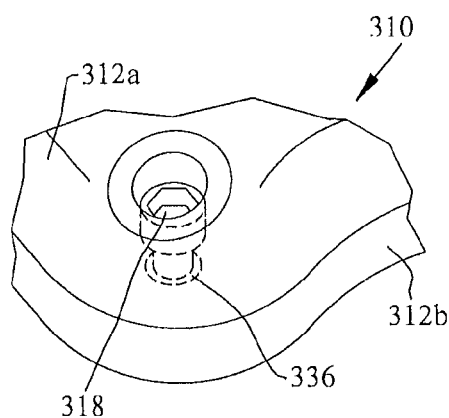
FIG. 16 is an enlarged view of one end of the case of the PDR device of FIG. 8 showing securement of the case together.

Referring now to FIG. 16, a close up enlarged view of an aperture and threaded fastener 318 is shown. Securement of housing 312 (i.e., front cover 312a and rear cover 312b) is achieved through the bonding of the RTV silicon in seal 329 along with the threaded fasteners/apertures 318. For corrosion resistance, military spec type stainless steel screws may be used, whereby the screws mate with a metal insert 336, which is screwed into rear cover 312b, This design is found to be vibration-resistant.

Figure 17:
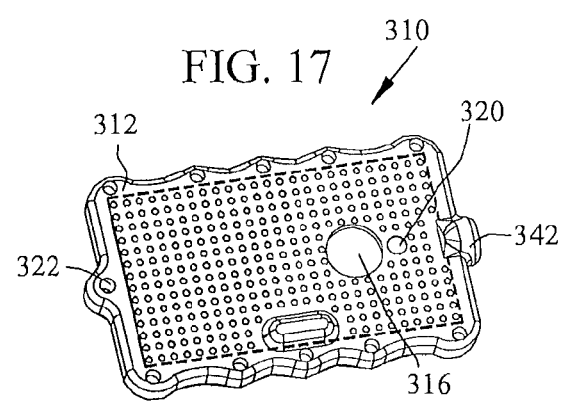
FIG. 17 is a perspective view of the PDR device of FIG. 8 showing the circuit board and voids.
Figure 18:
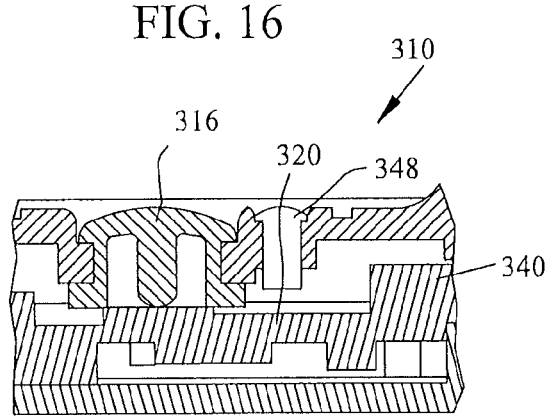
FIG. 18 is a partial cross-sectional view showing the control button and LED.
Figure 19:
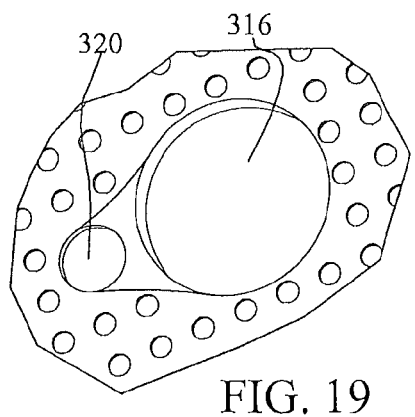
FIG. 19 is an enlarged plan view of the PDR device of FIG. 8 showing the main control button and LED.
Figure 21:
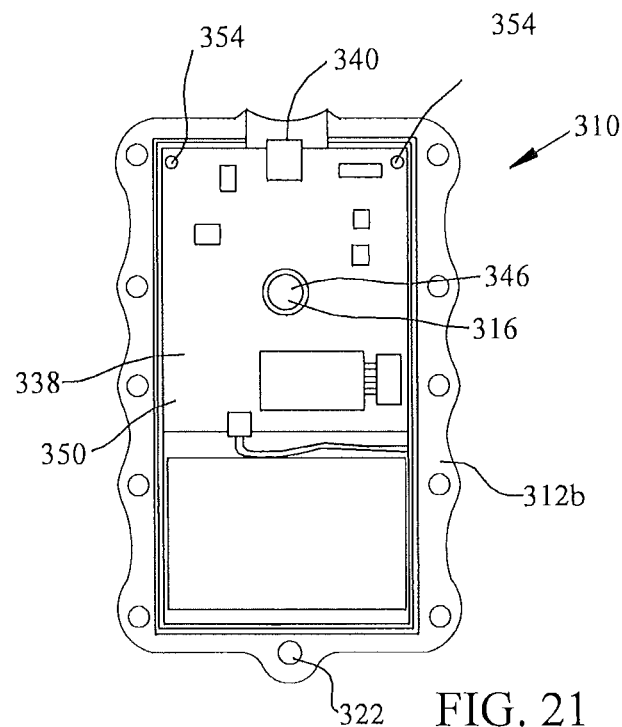
FIG. 21 is a plan view of the PDR device of FIG. 8 with the cover removed and showing a printed circuit board.

Referring now to FIGS. 15 and 21, electronics, which are contained on a printed circuit board, generally indicated as 338, are screwed to the nylon case 312, and neoprene padding is placed under the battery and voids between electronics and the inside of the enclosure where possible, as best shown in FIG. 17. Furthermore, all parts have nylon support tabs internally to hold circuit board 338 and the battery and position under high vibration and g conditions.

A USB connector 340 (FIG. 13) is provided beneath a sealed end cap 342. USB connector 340 is of the internal female type, but it should be noted that a slim overmolded male USB cable could be utilized to allow the cable to fit inside the open space 344 (FIG. 13) beneath end cap 342 and that mates with the internal USB female connector 340.

Figure 22:
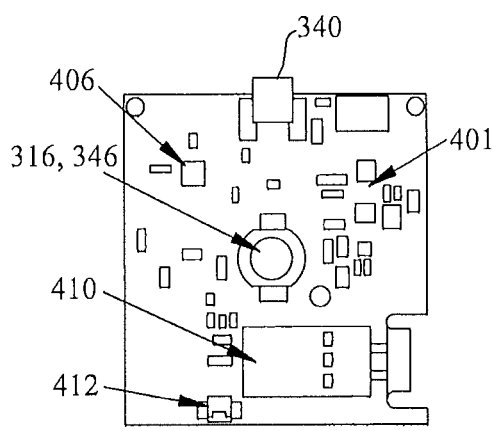
FIG. 22 is an enlarged partial front plan view of the front side of the printed circuit board of the PDR device of FIG. 8.

Coupled with main control button 316, which is a flexible switch cover, is a tactile switch 346 (FIGS. 15, 21, and 22). Main control button 316 allows the switch to be pressed while maintaining its tactile feel. This pass through is made to maintain the low profile so that the switch is not accidentally depressed while stored. The pass through is made to be pressed similar to a grommet and then additionally sealed with RTV silicon so as to maintain the waterproof integrity (see FIG. 19). Additionally, a light pipe 348 (see FIG. 18) is provided to allow the internal LED 320 to be viewed externally while maintaining a water tight seal. The light pipe is pressed into the front cover 312a of case 312 and sealed around a perimeter with RTV silicon or other suitable sealant to ensure the integrity of the seal.

The PDR system of the subject invention includes a web-based Graphical User Interface (GUI) application as well as one or more of the above hardware devices. The system runs a firmware in the PDR hardware to provide real-time control of sensors, communications, power management, and user interface. The PDR hardware is composed of several subsystems including power management, sensors, Wi-Fi, and 4 GB flash storage.

Figure 23:
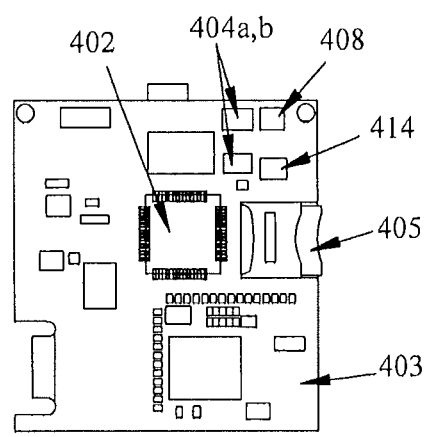
FIG. 23 is an enlarged partial rear plan view of the printed circuit board of the PDR device of FIG. 8.
Figure 24:
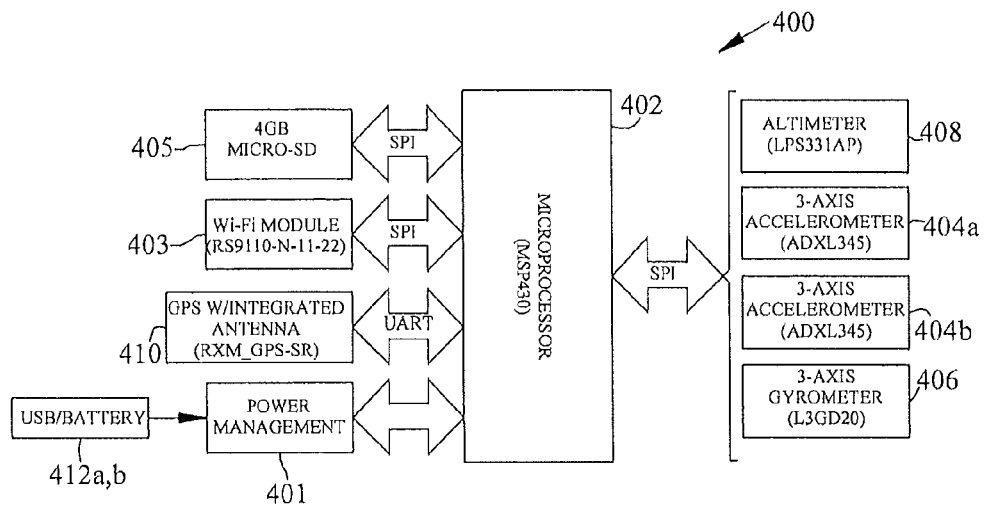
FIG. 24 is a block diagram for the PDR hardware.
Figure 25:
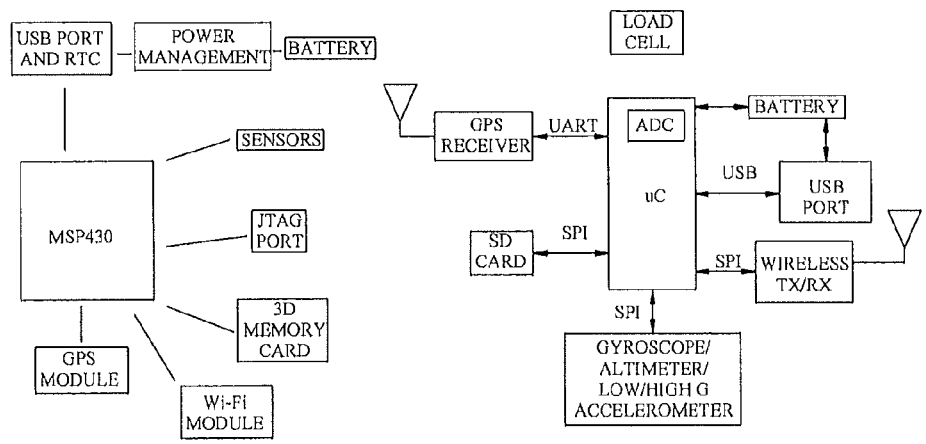
FIG. 25 is another block diagram of PDR hardware.
Figure 26:
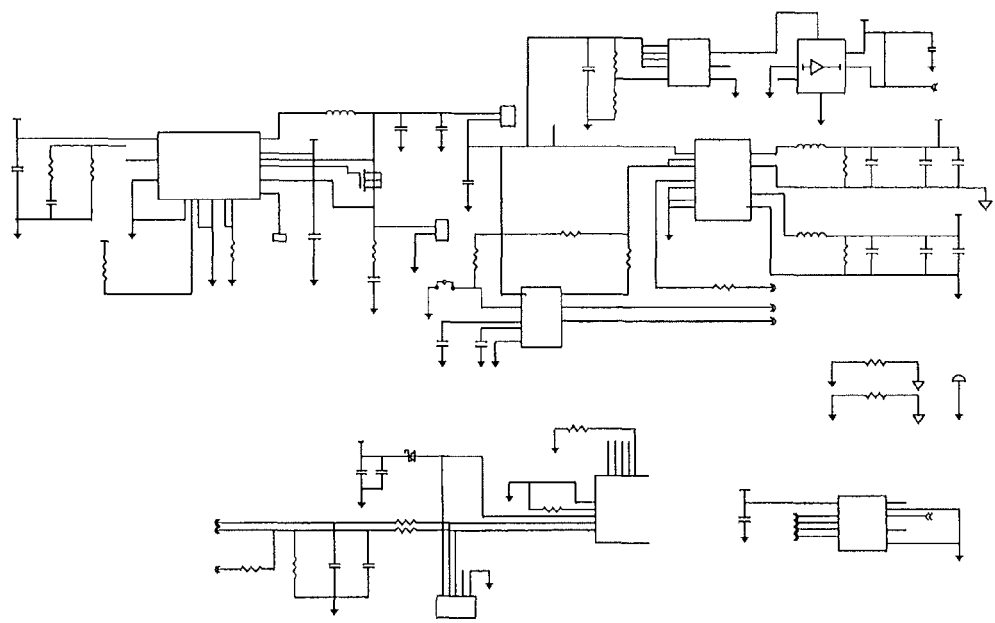
FIG. 26 is an electrical schematic diagram of power management of the PDR.
Figure 27:
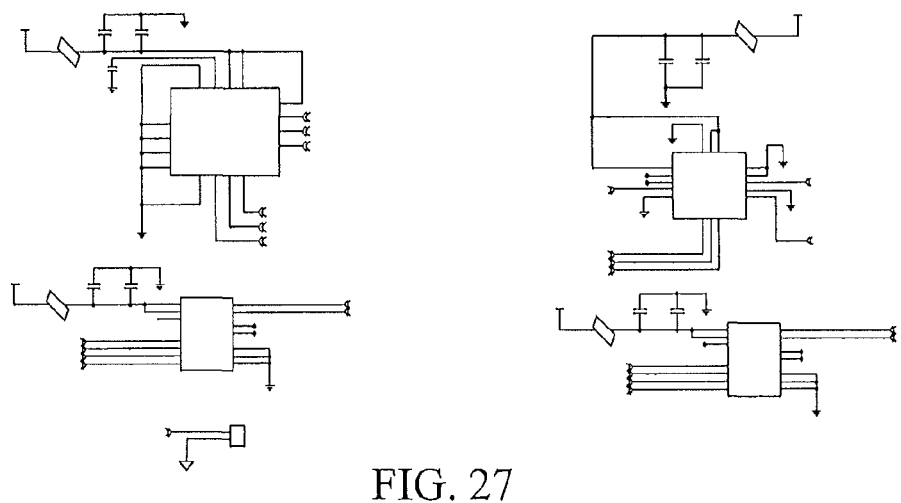
FIG. 27 are electrical schematic diagrams for the PDR sensors.
Figure 28:
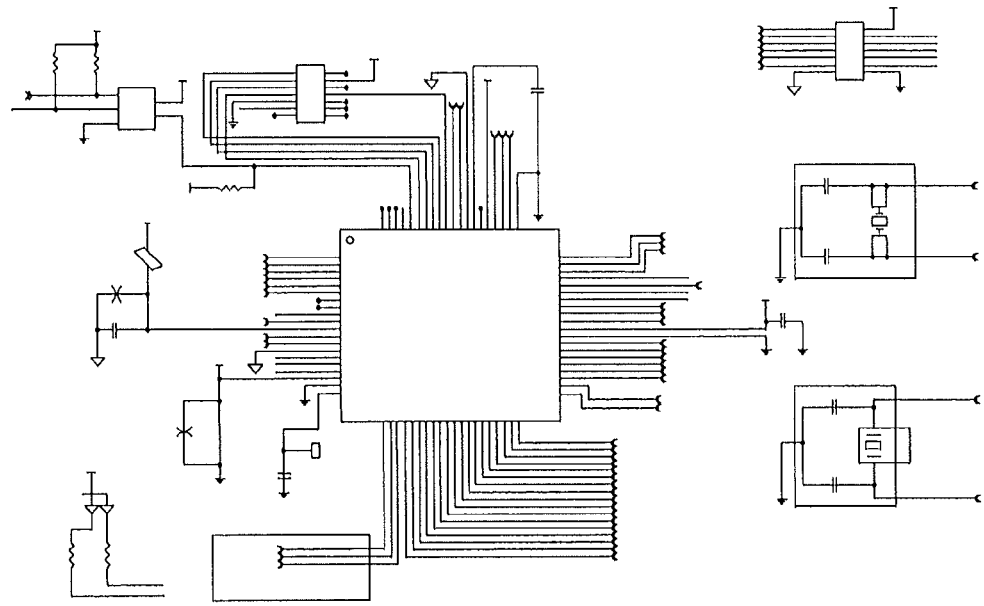
FIG. 28 is an electrical schematic diagram for the PDR microprocessor.
Figure 29:
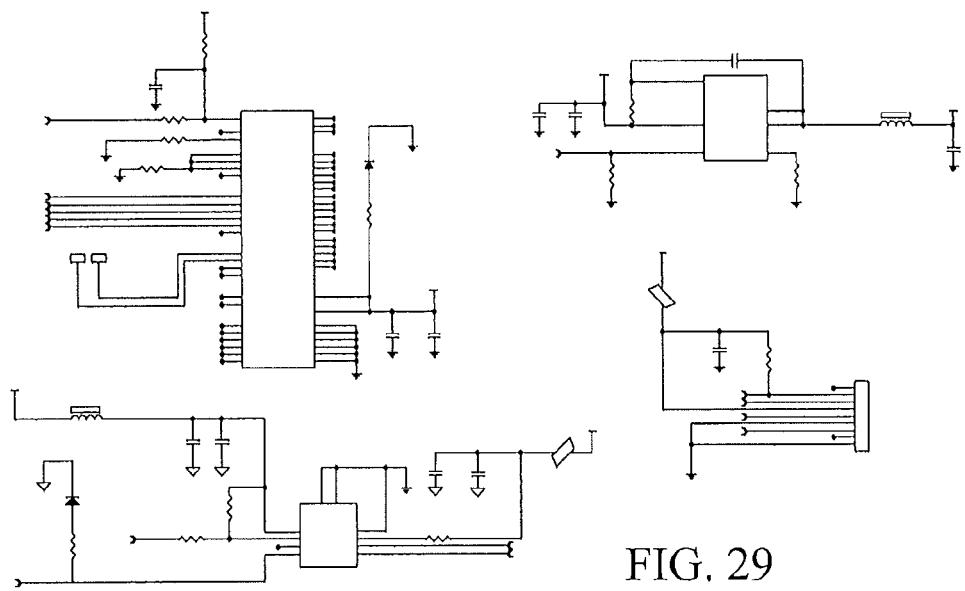
FIG. 29 is an electrical schematic diagram of the Wi-Fi and GBS receiver.

The PDR device is a rugged, network-ready, ultra-low power embedded device that is used to collect, store and transfer motion-based sensing data. Referring now to FIG. 24 (see also FIGS. 21-23), a hardware block diagram is indicated, generally as 400. The hardware is composed of several subsystems including: power management 401, sensors, Wi-Fi 403 and 4 GB flash storage 405. A microprocessor 402 is provided and may be based on the TI MSP430x family, which is an ultra-low power processor for multimedia applications. The PDR devices are equipped with several motion-based sensors including: 3-axis accelerometers 404a, 404b, 3-axis gyrometer 406, an altimeter 408 and GPS 410. Data is time-stamped and stored in real-time to removable flash 405, which can be access via USB 340 or Wi-Fi 403. The device may be powered by a battery and/or USB 412. A real-time clock 414 is also provided (FIG. 23). The device is also highly configurable, which can be modified to program power consumption, sensors, rates, calibration and network services. Sensors can be disabled or set at different sample rates to meet a large range of power requirements for different applications. Each sensor is a self-contained, mixed-signal, low-power system-on-chip (SOC) that supports detection events, programmability and high resolution data.

The web-based GUI is a cross-platform Java application that is supported on most handheld devices and personal computers. The GUI provides an easy interface to manage users and equipment (PDR devices, parachutes, etc.), schedule parachute jump sessions for a group of users (which may or may not have PDR devices installed on their equipment), and configure PDR devices (USB or WiFi). User and performance data is stored in a SQL database, which can be accessed over a local area network (or the Internet if the user chooses to do so) for further analysis. It should further be appreciated that the PDR device and system can include a scanner for scanning different components of the parachute system, such the riser, parachute canopy, oxygen, and altimeter. Each of the components has an associated ID number that can be tracked by the PDR and wherein a software package is provided to maintain a database for each component and further including information relating to the jumper, the rigger, etc. The software can be made to be accessible on-line and further includes the ability to link scanned items to a database that can provide factory recall alerts or maintenance action requests. This would alert the jumper or the rigger that there has been a factory recall or maintenance request for one of the parachute system components for addressing the same. Additionally, it should be appreciated that the database is equipped with the ability to present red flags or alerts to the rigger and/or jumper when certain components have exceed their design specifications or are the subject of a recall alert or maintenance request. As such, the database can provide an alert when the operational temperature of the parachute or equipment has been exceeded, the equipment has received excessive shock, or if the equipment has exceeded the maximum number of jumps recommended. It should further be appreciated that the PDR may be used as a health monitoring device to monitor such things including but not limited to pulse rate, blood pressure, and body temperature.

In one embodiment, the PDR hardware uses the Texas Instruments MSP430x ultra-low power microprocessor 402 as its main controller. The processor offers numerous advantages such as five low-power modes, numerous bus interfaces (SPI, UART, etc.), 12-bit analog-to-digital converters, 100 kB of internal Flash and 8 KB of RAM. Resources (memory and processing) are limited, so USB, Wi-Fi or recording cannot be enabled simultaneously.

The hardware consists of several motion-based digital sensors including the altimeter 408, the gyrometer 406, GPS module with integrated antenna 410, and the two accelerometers (low/high g-range) 404a, 404b. To reduce power consumption, the sensors are only powered and enabled when the device is in the recording mode. Micro-SD FAT16 file system 405 holds up to 4 GB and is supported to store configuration, firmware, and sensor log files, which are accessible via Wi-Fi 403 and USB 340 services. The USB 340 service is based on the mass-storage device driver class (MSC), which provides a user-friendly environment to browse the file system. The Wi-Fi module 403 may be from Redpine Signals, Inc. and is a self-contained Wi-Fi that includes an integrated MAC, baseband processor, RF transceiver, and power amplifier. The module is a complete end-to-end solution for ultra-low power WLAN applications such as data streaming, file transfer protocol (FTP) and other network services.

Now referring to FIGS. 15, and 21-22, in one embodiment the hardware includes a four-layer printed circuit board (PCB) 350 which may have a configuration size of 54.4× 60.2×10.9 mm. Schematics of the PDR hardware are shown in FIGS. 25-29. For PDR device 310, PCB 350 and battery 412, which may be of a lithium-ion type are properly secured and isolated to avoid measurement noise caused by vibrations. As discussed previously, enclosure material may be made from Nylon 6 fibers, which have a high tensile strength and elasticity. The front cover 312a of case 312 includes LED 220 for status indication, the main push button control 316, and USB port 340 which is made water tight with sealed end cap 342. Additionally, the axis orientation is preferably permanently labeled on the front cover of the enclosure (not shown).

As best shown in FIGS. 15 and 21, PCB 350 is secured to case 312, and in particular, to bottom cover 312b using two threaded fasteners 354.

The PDR user operations are based on main button 316, bi-color status LED 32 and mini-USB connector 340. Main button 316 is used to power the device by pressing and holding the button for a duration of greater than 2 seconds. When powered, the recording service 32 is enabled or disabled by pressing main button 316 and quickly releasing. The duration of the button press for recording mode is user-defined in the configuration file and cannot exceed 2 seconds. The default is set to 750 milliseconds.

To enable USB or Wi-Fi services, device 316 must be in the idle mode and the device must be connected to a USB source. If the source is a USB host (such as a PC), the USB mass-storage interface is enabled, and the device's file system is accessible from the USB host. If the USB is connected to a 5 volt-powered source instead of a USB host, then Wi-Fi is enabled, which allows access point scanning and the file transfer network protocol (FTP).

The following Table 1 summarizes the user operations for PDR device 310:

TABLE 1

PDR Device 310 User Operations

| Operation | Description |
| --- | --- |
| Power ON | Press and Hold button 316 for 2 second or until LED 320 enables |
| Power OFF | Press and Hold button 316 for 2 second or until LED 320 disables |
| Record ON | While powered on, press and release button 316 (<750 ms) |
| Record OFF | When powered on and recording, press and release button 316 (<750 ms) |
| USB-MSC | Connect PDR 310 USB port 340 to a USB host to mount the file system |
| Wi-Fi | Connect PDR 310 USB port 340 to a 5 V-power source to enable Wi-Fi scanning and FTP service. |

Status LED 320 provides up to four unique states including: IDLE Status (Solid Green): The device is ready and set to a low-power mode (<30 mW); Recording Status (Blinking Green): The device enables all sensors and continuously records sensor data to removable flash (FAT16 file system 405); Busy Status (Solid Orange): The device is busy performing an operation (Wi-Fi, USB, configuration, etc.). (Note: It is recommended that the user waits until the device enters the idle mode before performing the next operation); and Unrecoverable System Error (Solid Red): The device's firmware detected a hardware or software error and requires power cycling. Device and application settings can be modified in the configuration file to determine the cause.

A FAT16 file system is organized on 4 GB flash 405 via a micro-SD card. The file system includes the PDR configuration file, a firmware folder and sensor data files. The directory structure is described in Table 2.

TABLE 2

PDR Device 310 Directory Structure

| Item | Comments |
| --- | --- |
| Root | Root directory |
| fw | Firmware files (Wi-Fi) |
| config.pdr | Hardware configuration file |
| 20120105 | Top level recording folder for a given date |
| SESS_0 | Recording instance folder |
| ENSOR.BIN | Binary sensor log file |
| SESS_X | |
| ENSOR.BIN | Binary sensor log file |

The sensor data files (SENSOR.BIN) are organized by date (YYYYMMDD) and instance (i.e., SESS_0, SESS_1, . . . , SESS_N). The date and time when the binary log file is created provides an approximate time when the recording sessions started. All sampled data are time-stamped in seconds (millisecond accuracy) relative to midnight for a given day.

Figure 30:
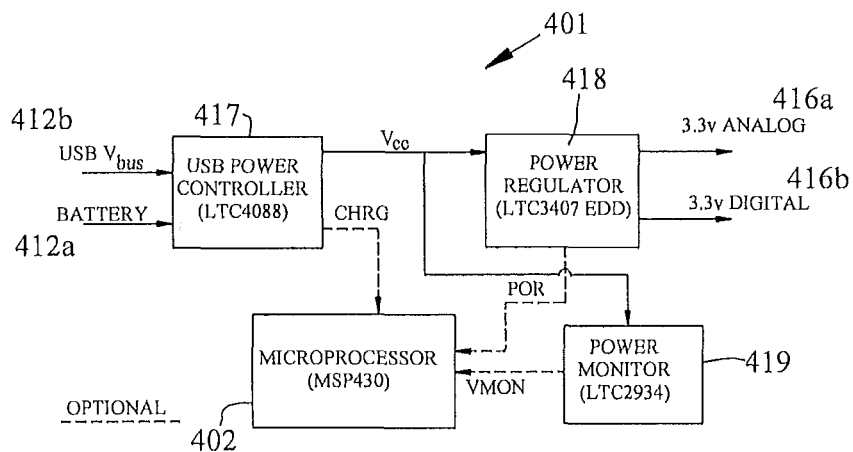
FIG. 30 is a block diagram of the power management system for the PDR.

Power management module (PMM) 401 is based on a standard chipset for power regulation, distribution, monitoring and battery recharging. As shown in FIG. 30, power is supplied by a powered USB device 412b or a lithium-ion battery 412a, which is regulated to an analog 416a and digital 3.3 v 416b (<800 mA) supply bus. The power management module 401 also includes a power controller 417 and power monitor 419. Three types of power monitoring signals are supplied to the microprocessor 402: power on reset (POR), battery charging (CHRG) and $V_{CC}$ voltage monitor. A power regulator 418 provides the POR signal, which asserts if the desired output power is out-of-range by 8%. The CHRG signal determines if the battery is charging (i.e., USB attached), and the VMON signal assert when $V_{CC}$ drops below 2.8 v. By default, these monitoring signals are not installed on the PCB, and are used for debugging purposes.

PDR device 316 supports multiple power modes based as shown below in Table 3 on enabled sensors and data rates. Power consumption can easily be customized per application by setting up the configuration file located on the device's file system.

TABLE 3

Power Consumption Ratings

| Mode | Current Rating (mA peak @ 3.3 v) | Hours of Operation | Comments |
|---|---|---|---|
| Idle (w/LED) | 8.8 | 107 | Device is power and in idle mode. This includes power from MSP430, LEDs and on board electronics |
| Idle (w/o LED) | 6.8 | 139.0 | All LEDs are removed from PCB |
| Recording (L1) | 26.5 | 35.0 | Alt: 25 Hz, 2x Accel: 200 Hz, Gyro: 190 Hz, GPS disabled. |
| Recording (L2) | 49.8 | 19.0 | Alt: 25 Hz, 2x Accel: 800 Hz, Gyro: 760 Hz, GPS disabled. |
| Recording (L3) | 78.8 | 12.0 | Alt: 25 Hz, 2x Accel: 800 Hz, Gyro: 760 Hz GPS: Unlocked. |
| Recording (L4) | 77.4 | 12.0 | Alt: 25 Hz, 2x Accel: 800 Hz, Gyro: 760 Hz GPS: Locked |
| Wi-Fi | <193 | <4.5 | Measured during FTP file transfer |
| USB-MSC | <57 | <16.5 | Measured during USB file transfer |

The PDR hardware supports two real-time clocks (RTC) 414 to maintain the current date and time for time-of-day time-stamping. The MSP430x processor 402 does not support an RTC battery backup pin, so the date and time is maintained on an external RTC (RV-2123). During firmware initialization the date and time is read from the external RTC, which is used to set the internal RTC 414 for fast access times while recording. Times-tamping sensor data is accomplished by reporting the number of second's relative from midnight with microsecond accuracy. This is accomplished by synchronizing a hardware timer with the internal RTC 414.

The PDR hardware supports five integrated sensors on a single SPI bus: tri-axis gyrometer 406, tri-axis low-g accelerometer 404a, tri-axis high-g accelerometer 404b, altimeter 408, and GPS 410 with integrated antenna. Each sensor is programmable (rates, filtering, etc.) and offers unique features such as low-power detection modes (e.g., free-fall). A summary of each sensor's specification used in the prototype PDR device 310 is listed in Table 4. More detailed information of these sensors is provided below.

TABLE 4

Sensor Specifications

| Device | Data rates (Hz) | Data Resolution (bits) | Data Range | Operating Current Rating (mA) | Idle Current Rating (mA) |
|---|---|---|---|---|---|
| Low-G Accelerometer 404a | <800 | 11 | ±4 g | <0.140 | 0.0001 |
| High-G Accelerometer 404b | <800 | 13 | ±16 g | <0.140 | 0.0001 |
| Altimeter (Pressure/Temperature) 408 | 25 | 24 16 | 260-1260 mBar 0-80° C. | <0.030 | 0.0005 |
| Gyrometer 406 | <800 | 16 | ±2000 dps | <6.1 | 0.0005 |

The combined data throughput is limited by the rate of processor 402 (25 MHz) and the SPI interface (12.5 Mb/s), which has a maximum flash 512-byte write-access rate of 100 kB/s. The effective data rate is much less due to the overheads for servicing sensor (data) interrupts. The maximum effective sensor data rate is defined as 800 Hz (if supported) when all sensors are enabled. At maximum capacity dropped samples are likely due to CPU processing load.

One suitable accelerometer is the ADXL345 accelerometer from Analog Devices which is an ultra-low power, factory calibrated, 3-axis accelerometer with high resolution (13-bit) and a measurement range up to ±16 g. The PDR hardware consists of two accelerometers 404a,b, which are configured for two different g-ranges: ±4 g and ±16 g. The design also includes two accelerometers 404a,b to provide additional hardware detectors (total of 4) for ultra-low power event triggering (e.g., free-fall and bi-threshold detection). In future firmware versions, the low-g acceleration is expected to be used as a detector to provide time-stamped event markers. The specifications for the ADXL345 are defined in Table 5.

TABLE 5

ADXL345 Accelerometer Specifications
ADXL345 Specifications

| | |
|---|---|
| Supply Voltage | 2.4 V to 3.6 V |
| Operating Temperature | −40° C. to +85° C. |
| Sample Resolution | 11-bit (4 g), 13-bit (16 g) |
| Operating Current Consumption | <140 uA |
| Power Down Current Consumption | 0.1 uA |
| Sensitivity | 3.9 mg/LSB |
| Data Rates | 0.10/0.20/0.39/0.78/1.56/3.13/ 6.25/12.5/25/50/100/200/400/ 800/1600/3200 Hz |
| Shock Survival | 10,000 g |

One suitable altimeter 408 is the LPS331AP altimeter from STMicroelectronics, which is an ultra-low power, factory calibrated pressure and temperature sensor that includes a SPI/IC digital interface, and integrated bi-threshold detector. Table 6 shows a brief summary of the device's hardware specification.

TABLE 6

LPS331AP Altimeter Specification
LPS331AP Specifications

| | |
|---|---|
| Supply Voltage | 1.71 V to 3.6 V |
| Operating temperature range | −40° C. to +85° C. |
| Full accuracy temperature range | 0° C. to +80° C. |
| Operating pressure range | 260 mbar~1260 mbar |
| Sample Resolution | 24-bit (pressure), 16-bit (temperature) |
| Operating Current Consumption | <30 uA at 1 Hz |
| Power Down Current Consumption | 0.5 uA |
| Sensitivity | 4096 LSB/mbar (pressure), 480 LSB/° C. (temperature) |
| Data Rates | 1/7/12.5/25 Hz (for pressure and temperature) |
| Shock Survival | 10,000 g |

One suitable gyrometer 406 is the L3GD20 gyrometer from STMicroelectronics, which is a low-power, factory calibrated, 3-axis angular rate sensor that includes a SPI/IC digital interface. The sensor is a mixed-signal integrated circuit that includes numerous features such as filtering, power modes, signal detection and temperature output. The PDR device hard-codes the data range to +/−2000 degrees per second (dps), which is adequate for most applications. Table 7 shows a brief summary of the devices hardware specification.

TABLE 7

L3GD20 Gyrometer Specifications
L3GD20 Specifications

| | |
|---|---|
| Supply Voltage | 2.4 V to 3.6 V |
| Operating Temperature | −40° C. to +85° C. |
| Sample Resolution | 16-bit (signed) |
| Operating Current Consumption | 6.1 mA |
| Power Down Current Consumption | 5 uA |
| Sensitivity | 70 mdps/LSB @ 2000 dps |
| Data Rates | 95/190/380/760 Hz |

One suitable GPS 410 is the RXM-GPS-SR GPS module from Linx Technologies is a self-contained low-power GPS module with integrated patch antenna, LNA and SAW filter. It is based on the SiRFstar III chipset and targets low power applications. The low-power consumption is based on an adaptive trickle power control, which cycles between power modes once a position fix is determined. The GPS module consumes the most power than all other sensors, so disabling the GPS module can save hours of battery-life. Table 8 shows a brief summary of the devices hardware specification.

TABLE 8

RXM-GPS-SR GPS Specifications
RXM-GPS-SR Specifications

| | |
|---|---|
| Supply Voltage | 3.0 V to 4.3 V |
| Operating Temperature | −30° C. to +85° C. |
| Sample Resolution | 32-bit (float) |
| Operating Current Consumption | <49 mA (9 mA avg. when locked) |
| Channels | 20 |
| Hot Startup Time | 2 seconds (open sky) |
| Cold Startup Time | 35 second (open sky) |
| Position Accuracy | 10 m, 5 m (SBAS) |
| Max Altitude | 60,000 feet |
| Max Velocity | 1,000 knots |
| Data Rate | 1 Hz |
| Supported Protocol | NMEA 0183 ver. 3.0 |

A binary converter utility (Windows executable file) is provided to convert the binary sensor log files to a human readable comma delimited format (CSV), which also normalizes the data units as described below in Table 9.

TABLE 9

CSV Files and Units

| File | Sensor | Format [unit] |
|---|---|---|
| accelerometer_lg.csv | 3-axis acceleration +/− 4 G | <time [sec], x [g], y [g], z[g]> |
| accelerometer_hg.csv | 3-axis acceleration +/− 16 G | <time [sec], x [g], y [g], z[g]> |
| altimeter.csv | Pressure | <time [sec], pressure [mbar]> |
| gyro.csv | 3-axis gyrometer (angular velocity) | <time [sec], x [dps], y [dps], z [dps]> |
| gps.csv | GPS | <time [sec], latitude [deg], longitude [deg]. height [m]> |
| temperature.csv | Temperature associated with altimeter | <time [sec], temp [degC.]> |

To execute the conversion tool, specify the input file path and the optional output directory path and rotation angles as shown below:

BinaryLogConverter.exe <filepath> [output directory] [x-axis rotation (deg)] [y-axis rotation (deg)] [z-axis rotation (deg)]

If a parsing error occurs (e.g., file corruption) the binary log converter will drop corrupted samples and continue parsing.

Figure 31:
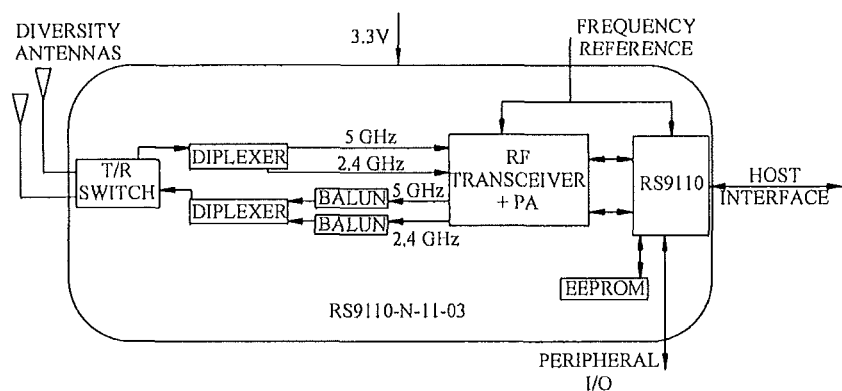
FIG. 31 is a system diagram of a wireless network module.

PDR device 316 includes networking capabilities by using the self-contained wireless module 403, which may be provided by Redpine Signals. This module is an IEEE 802.11abgn Wi-Fi client with integrated RF, baseband processing, MAC and power savings. A low-level SPI driver is provided and supported by Repine Signals, which required minor modification for our purposes. FIG. 31 illustrates a high-level system diagram for the module.

The memory capacity on the MSP430xF55xx processor 402 is 8 KB plus an additional 2 KB reserved memory for the USB peripheral. The firmware takes advantage of the additional 2 KB of memory by creating a dynamic memory pool for general purpose usage when USB services are not enabled. The firmware currently does not have sufficient RAM to offer all available features such as data streaming service, axis rotations, and motion-based event triggering. As results these features are disabled. To overcome this limitation, the MSP430 processor with 16 KB of RAM can be used with hardware revisions.

PDR device 310 power consumption varies based on enabled sensors/devices, data rates and sensor states (e.g., GPS lock). The PDR has to have two main operating modes: idle and recording. Idle mode is a low power (<1 mA) operation mode for automatic record triggering.

Figure 32:
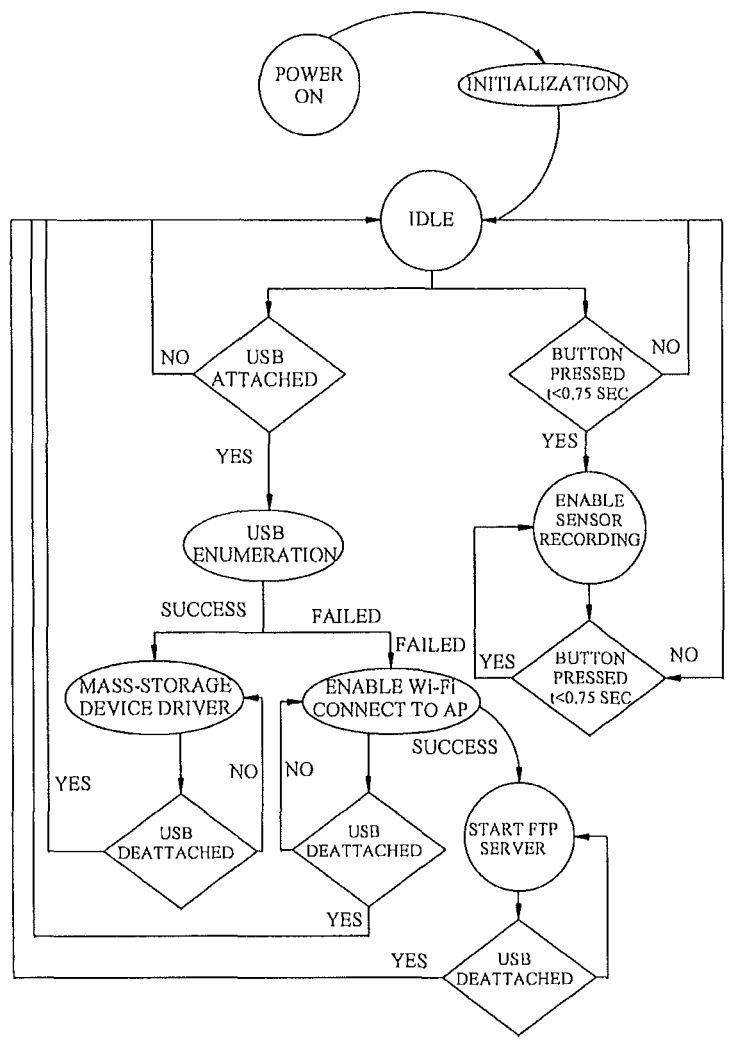
FIG. 32 is a flow chart for the PDR firmware.

The PDR firmware consists of the program and data memory associated with the hardware that gets executed on the MSP430x 16-bit microprocessor 402. The operating system or kernel is based on SYS/BIOS 6.x kernel, which provides real-time scheduling and hardware specific options such as power management. The firmware is designed to support all data bus (UART, SPI, etc.) and user-interfaces (e.g., button & LED), FAT16 file system, file configuration parsing, and services such as recording, USB mass-storage (USB MSC), and the file transfer network protocol (FTP). A high-level flow chart for the firmware is illustrated in FIG. 32.

When device 310 is powered on, all interfaces and devices are initialized. If a component fails, the device reports an unrecoverable system error (red LED status) and the unit must be power-cycled. This should not happen, but to assure successful initialization, sensor or application level features can be disabled in the configuration file.

Once the device is in idle mode, three different services are supported: sensor recording, mass-storage interface and networking. The recording service powers on and enables all sensors and interfaces to log raw binary data to external flash, which includes a FAT16 file system. The remaining services are used to retrieve binary log files and perform common file system tasks: File transfer network protocol (FTP) and USB mass-storage interface.

Figure 33:
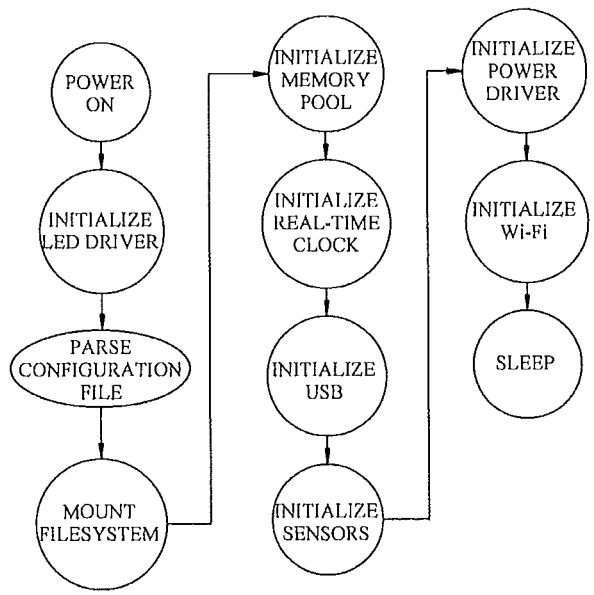
FIG. 33 is an initialization block diagram for the PDR hardware.

The PDR hardware has a complex and strict power sequencing and initialization routine as illustrated in FIG. 33. If any process or hardware component fails, the PDR device will report an unrecoverable system error (red status LED) and will require power cycling. Components and processes can be disabled in the configuration file for debugging and identifying the cause of the initialization error.

Initialization include parsing the configuration file and initializing device drivers (e.g., sensors, flash, Wi-Fi, etc.). Once initialization is completed successfully, the device is powered down into low-power mode 0 (LPM0), which disables all MSP430x system clocks and consumes approximately 300 uW of power. The device automatically wakes up when an interrupt from the main button or a sensor is received by the CPU.

The device configuration file allows the user to configure sensors, rates, networking and other application specific settings. The configuration filename is "config.pdr" and is located in the root directory of the 4 GB micro-SD flash drive. The configuration file is defined by a set of groups with <key,value> pairs. The configuration file is based on a strict ASCII format and is easily acceptable to parsing errors.

The device group defines read-only hardware specific settings.

TABLE 10

Device Group Settings

| Device | Value | Notes |
| --- | --- | --- |
| HWVer | 0-65536 | A unique 16-bit hex code to identify the hardware version (020A -> 02.10) |
| DeviceId | 0-65536 | A unique 16-but hex code to identify the PDR device |
| BtnThreshold | 0-255 | A hardware dependent threshold for the push button controller. | device
{
   HWVer=0400
   DeviceId=0001
   BtnThreshold=750
}

The application group controls the user interface and services. This group is only meant for debugging purposes, but LED 320 can be disabled to reduce power consumption (2 mA).

TABLE 11

Application Group Settings

| Application | Value | Application level control |
| --- | --- | --- |
| recording | Bool (true or false) | Enables or disables the recording |
| led | Bool | Enables or disables the status LED |
| wifi | Bool | Enables or disables Wi-Fi |
| rtc | Bool | Enables or disables real-time clock | application
{
   recording=true
   led=true
   wifi=true
   rtc=true
}

The sensor group is used to enable and disable individual sensors. This is useful when a sensor fails and needs to be disabled, or when lower power consumption or longer recording time is required.

TABLE 12

Sensor Group Settings

| Sensors | Value | Notes |
| --- | --- | --- |
| altimeter 408 | Bool (true or false) | Enables or disables the altimeter |
| gyro 406 | Bool | Enables or disables the gyrometer |
| lowg_accel 404a | Bool | Enables or disables the low-g accelerometer |
| highg_accel 404b | Bool | Enables or disables the high-g accelerometer |
| gps 410 | Bool | Enables or disables the GPS | sensors
{
   altimeter=true
   gyro=true
   lowg_accel=true
   highg_accel=true
   gps=true
}

The rate group controls the data rate for each sensor. The maximum supported data rate is 800 Hz, which is supported by the accelerometers 404a,b and gyrometers 406.

TABLE 13

Sensor Group Settings

| Rates | Values | Notes |
| --- | --- | --- |
| altimeter | 0 | (0) 25 Hz |
| gyro 406 | 0-3 | (0) 95 Hz |
| | | (1) 190 Hz |
| | | (2) 380 Hz |
| | | (3) 760 Hz |
| lowg_accel 404a | 0-5 | (0) 25 Hz |
| | | (1) 50 Hz |
| | | (2) 100 Hz |
| | | (3) 200 Hz |
| | | (4) 400 Hz |
| | | (5) 800 Hz |
| highg_accel 404b | 0-5 | (0) 25 Hz |
| | | (1) 50 Hz |
| | | (2) 100 Hz |
| | | (3) 200 Hz |
| | | (4) 400 Hz |
| | | (5) 800 Hz | rates
{
   altimeter=3
   gyro=3
   lowg_accel=5
   highg_accel=5
}

The calibration group is used to linearly bias the raw samples to compensate for PCB placement errors. All of the sensors are factory calibrated over the specified operating temperature.

TABLE 14

Calibration Group Settings

| Calibration | Values | Notes |
| --- | --- | --- |
| accellg_x/y/z | +/- 4000 [mg] | Low-G accelerometer 3-axis calibration offsets in mg. |
| accelhg_x/y/z | +/- 16000 [mg] | High-G accelerometer 3-axis calibration offsets in mg. |

TABLE 14-continued

| Calibration Group Settings | | |
|---|---|---|
| Calibration | Values | Notes |
| gyro_x/y/z | +/− 2000.0000 [dps] | Gyro 3-axis calibration offsets in degrees/sec. |

```
calibration
{
  # Low-G accelerometer [mg]
  accellg_x=0
  accellg_y=0
  accellg_z=0
  # High-G accelerometer [mg]
  accelhg_x=0
  accelhg_y=0
  accelhg_z=0
  # Gyrometer (degrees/sec)
  gyro_x=0
  gyro_y=0
  gyro_z=0
}
```

The rotation applies a 3D axis rotation by specifying the Euler angles for each axis. Setting all angles to zero bypasses the matrix computation, which increases processing capabilities (i.e., supports high data rates). When the rotation is enabled, the sensor data rates should be lowered due an increase in processing load to avoid data loss.

TABLE 15

| Rotation Group Settings | | |
|---|---|---|
| Rotation | Value | Notes |
| x | [degrees] | X-axis rotation in degrees |
| Y | [degrees] | Y-axis rotation in degrees |
| z | [degrees] | Z-axis rotation in degrees |

```
rotation
{
  x=0
  y=0
  z=0
}
```

The interface group defines the network interface settings to establish a static or dynamic IP address with a wireless access point.

TABLE 16

| Interface Group Settings | | |
|---|---|---|
| Interface | Value | Notes |
| dhcp | Bool | Enables or disables DHCP support |
| address | String "xxx.xxx.xxx.xxx" | Static IP address |
| netmask | String "xxx.xxx.xxx.xxx" | Static netmask IP address |
| gateway | String "xxx.xxx.xxx.xxx" | Static gateway IP address |

TABLE 16-continued

| Interface Group Settings | | |
|---|---|---|
| Interface | Value | Notes |
| dns | String "xxx.xxx.xxx.xxx" | DNS IP address |
| band | 0-1 | RF Band (0) 2.4 GHz, (1) 5 GHz |

```
interface
{
  dhcp=false
  address=192.168.0.130
  netmask=255.255.255.0
  gateway=192.168.0.1
  dns=192.168.0.1
  band=0
}
```

The access point group defines access points and security settings to connect to after performing a scan. Up to five access-point groups can be defined in the configuration file, which is a prioritized list.

TABLE 17

| Access Point Group Settings | | |
|---|---|---|
| accesspoint [x] | Value | Notes |
| ssid | string | Service set identifier |
| type | 0-1 | RF Band (0) ad-hoc (1) infrastructure |
| security | string | Open, WPA1, WPA2, WEP |
| powerlvl | string | low (6-9 dBm), medium (10-14 dBm), high (15-17 dBm) |
| psk | String/hex code (wep) | pre-shared key (32 byte) |

```
accesspoint
{
  ssid=asygps
  type=1
  security=wep
  powerlvl=high
  psk=8D57DE8605
}
```

The FTP group defines the file transfer protocol (FTP) username and password.

TABLE 18

| FTP Group Settings | | |
|---|---|---|
| FTP | Value | Notes |
| username | string | FTP username |
| password | string | FTP password |

```
ftp
{
  username=pdr
  password=pdr
}
```

Data storage is supported with a 4 GB external flash via a removable micro-SD card 405. The flash is expected to be formatted to FAT16 to provide an easy-to-use drive interface. Data processing consists of handling data events (interrupts) from all sensors, processing samples (scaling, rotating, etc.) and then writing to a managed and thread safe buffer. Each sensor (accelerometers 404*a,b*, altimeter 408, GPS 410, gyrometer 406) consists of a hardware interrupt that automatically notifies the MSP430x processor 402 when new data is ready. Each sample is then converted and time stamped into a binary packet. The data packet includes a 10-byte header and payload section, where the header includes the packet type, code word and time (millisecond resolution).

Figure 34:
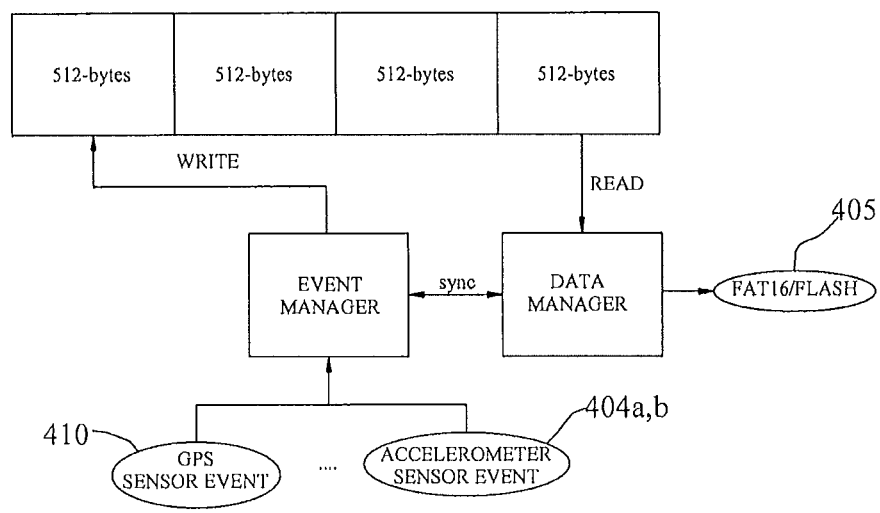
FIG. 34 is a block diagram of buffer management.

The buffer consists of 2048 bytes of memory laid out in 4 blocks of 512 bytes as shown in FIG. 34. A block of 512 bytes is used to match the flash's block size, where the minimal transfer size to flash is 512 bytes. Since RAM is limited, the reserved USB 340 memory is used; therefore USB 340 features are not supported during recording operations. The event and data manager synchronize read operations from sensor events (i.e., samples) and write operations to external flash (micro-SD). The buffer manager also includes a flush operation when recording is disabled. This is required because a data packet can cross a 512-byte boundary.

If a buffer overflow occurs due to limited processing power, the PDR device will report an unrecoverable system error. To reduce likelihood of such error, the sensor data rates should be reduced.

The sensor data rates (i.e., bandwidth) are also limited by the write-access time for external flash. The upper limited was measured to be 100 KB/s when no additional processes were running. The effective throughput is lower, and is determined by CPU processing loads during interrupt handling, rate and computation. The estimated recording bandwidth is 35.4 KB/s as shown in Table 19.

TABLE 19

Expected Write-Access Bandwidth

| Device | Packet Size | Max Sample Rate (Hz) | Bandwidth (KB/s) |
|---|---|---|---|
| Low-G Accelerometer 404a | 15 | 800 | 12 |
| High-G Accelerometer 404b | 15 | 800 | 12 |
| Altimeter 408 | 15 | 25 | 0.375 |
| Gyrometer 406 | 15 | 760 | 11.4 |
| GPS 410 | 21 | 1 | 0.021 |
| Total Bandwidth | | | 35.376 |

Automatic event triggering is used to toggle operation modes (e.g., idle to recording) based on events driven by the hardware sensors (e.g., free-fall, thresholds, etc.).

Gyrometer 406 in the prototype is not an ultra-low power components (<1 mA), so to minimize power consumption in the idle mode, the accelerometers 404*a,b* and altimeter 408 detectors are expected to be used for automatic triggering. One benefit of having two accelerometers 404*a,b* is to have up to 4 independent event triggers. The following describes the hardware detectors supported for each sensor:

Accelerometer (404*a*, 404*b*)
  Single threshold event
  Double threshold event
  Activity and inactivity events (threshold over time)
  Free-fall
Altimeter (408)
  Single threshold event
Gyrometer (406)
  Single threshold detection event
  Duration threshold events (e.g., how long above threshold)

The firmware supports Wi-Fi 403 network service when a 5V-powered USB 412*b* is attached to the device (no USB host). The primary service is the File Transfer Protocol (FTP), which provides a standard and well known method to access the device's file system, perform file transfers and other site-specific features. As part of the FTP service a sensor data streaming service (SDSS) is also supported. This allows a user to visualize sensor data in a readable and normalized format from a client application. The SDSS service is currently not supported by the web-based GUI application, but may include a binary format to achieve faster transfer rates.

The file transfer protocol (FTP) server in one embodiment is a limited version of the specification, but offers minimal feature to be compatible with well-known applications such as WinSCP and FileZilla. Table 20 provides a list of the supported commands.

TABLE 20

Supported FTP Commands

| Supported Commands | Description |
|---|---|
| CDUP | Makes the parent of the current directory be the current directory |
| CWD | Makes the given directory be the current directory on the remote host |
| DELE | Deletes the given file on the remote host |
| LIST | sends information about that file, or sends information about each file in that directory |
| MKD | Creates the named directory on the remote host |
| NLST | Returns a list of filenames in the given directory |
| NOOP | Does nothing except return a response |
| PASS | After sending the USER command, send password to complete login |
| PASV | Tells the server to enter "passive mode" |
| PWD | Returns the name of the current directory on the remote host |
| RETR | Begins transmission of a file from the remote host |
| RMD | Deletes the named directory on the remote host |
| SITE | Executes a site-specific command |
| STOR | Begins transmission of a file to the remote site |
| TYPE | Sets the type of file to be transferred |
| USER | Send this command to begin the login process |
| FEAT | Requests the list of featured commands |
| QUIT | Terminates and restarts the FTP service |

The FTP service supports several site-specific commands that are used for configuration and controlling additional services as shown in Table 21.

TABLE 21

FTP Site-Specific Commands

| Supported Commands | Command Format | Description |
|---|---|---|
| STM | SITE STM <port>, <date rate[ms]> | Enables sensor data streaming service |
| QSTM | SITE QSTM | Disable sensor data streaming service |
| RTC | SITE RTC [YYYYMMDDHHMMSS] | Queries or sets the RTC time (24-hour mode) |

The external real-time clock (RTC) 414 of PDR device 310 is used to maintain the date and time while the device is powered off. The battery 412*a* supplies RTC 414 power, so if the battery 412*a* is removed or exhausted the date and time will be reset. The site-specific RTC command enables the user to remotely set or query the RTC time.

The next command includes a secondary Wi-Fi 403 service called the sensor data streaming service (SDSS). This service enables sensors as requested and transmits normalized samples in a CSV ASCII format over a TCP network connection. Once the service is initialized, five TCP servers are created. The port identifier for each service is determined by the specific port field when sending the STM command. Each server (e.g., sensor) has a unique port identifier that is indexed based on the base port identifier. Once a client connects to the service, the sensor is enabled and data is automatically transmitted from the device at the specified rate.

TABLE 22

Sensor Data Streaming Servers

| TCP Port ID | Sensor |
| --- | --- |
| Port +0 | Low-g Accelerometer |
| Port +1 | High-g Accelerometer |
| Port +2 | Altimeter (pressure & temperature) |
| Port +3 | Gyrometer |
| Port +4 | GPS |

The software is a web-based GUI application that incorporates Applicant's Java based software infrastructure. The application manages user and performance data, and consists of additional tools for device scanning, configuration, data extraction, and visualization. The user data is associated with scheduling, users, and their roles (admin, jumper, jumpmaster, etc.) as well as equipment (e.g., parachutes, equipment, PDR devices 310). The performance data is associated with the processed or raw sensor data from PDR device 310. The user and performance data is stored in a SQL database.

The software is a web-based application written using the Grails application framework. Grails is an Open Source, full stack, web application framework for the JVM. It takes advantage of the Groovy programming language and convention over configuration to provide a productive and stream-lined development experience. Java 7 a Grails version 2.2.1 were used to developed the PDR software.

Figures 35, 36:
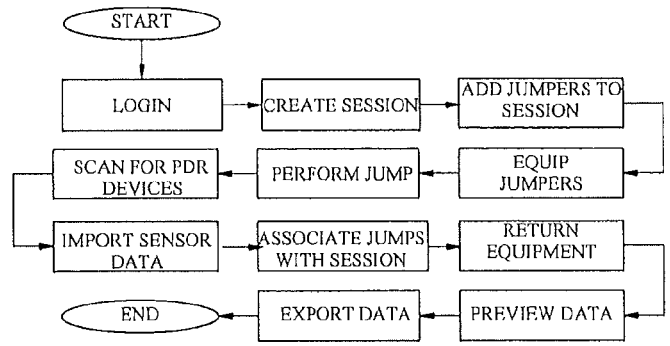
FIG. 35 is a work flow diagram.
FIG. 36 is an example of a list of current users on the Graphical User Interface (GUI)

Other libraries that are used include:
ftp4j (http://www.sauronsoftware.it/projects/ftp4j/), FTP library
jQuery (http://jquery.com/), JavaScript framework
Bootstrap (http://twitter.github.com/bootstrap/), CSS framework
Rickshaw (http://code.shutterstock.com/rickshaw/), data plotting JavaScript framework
Full calendar (http://arshaw.com/fullcalendar/), jQuery JavaScript plugin for calendar views FIG. 35 illustrates the overall workflow. A jump session is first created and the session is configured with jumpers and equipment (including assigning jumpmaster and checking out equipment including PDR devices). Then the jumps can be performed. Once back at the "base," an administrator can scan for the returned devices and import the recorded performance data. The imported performance data should then be associated with the appropriate session (has to be done manually). Once this is done, the used equipment can be returned to make it available for future jumpers. Now the performance data can be previewed and exported for further analysis.

It is possible for an administrator to create new, and delete existing users. Each user can have one or multiple roles. The roles presently include, but are not limited to:
Administrator
Jumper
Jumpmaster
Quarter master Not all roles need to be used. The administrator has full access to the application and can modify any database object, and is also the only user who can create or modify users. FIG. 36 shows an example of the GUI showing a list of current users. User details can be seen by clicking on the username of a particular user. There is also a link to create a new user in the upper right corner.

Each user can also have the following information associated with it:
Username
Password
First name
Last name FIG. 37 shows a screenshot for adding a new user using the PDR software. Only defined users can be associated with jump sessions and be associated with performance data.

Figure 38:
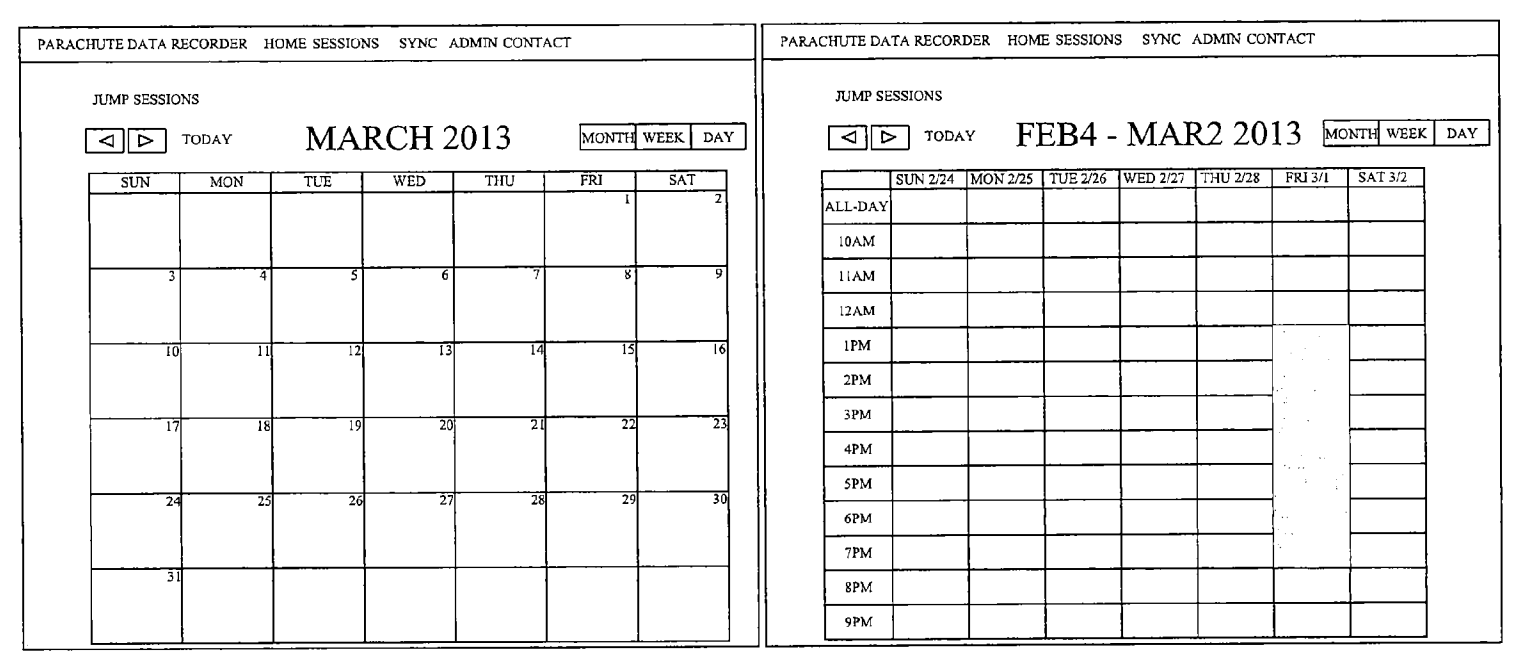

The session section of the GUI allows users to plan jump sessions. This includes stating when the jump session will take place using an intuitive calendar view. The calendar provides an overview of all the jump sessions, either in a month, week, or day view. Example of a month view and a day view are shown in FIG. 38.

Clicking on a session allows regular users to view information about the session, including any performance data that may be associated with the session.

Administrator users on the other hand can create new sessions and edit existing sessions. To create a session the administrator can click (month view), or click and drag (week and day view), on the calendar. After this is done the user will be prompted to provide a session name. The administrator can now add or remove jumpers from the session, state which jumper is the jumpmaster, and equip the jumpers. Equipment includes parachutes, PDR devices, or other equipment (e.g., oxygen tanks, video cameras). FIG. 39 shows the details of an example session.

Future sessions are jump sessions that have not yet taken place. Whether a session that has taken place is not determined by the session time vs. the current time, but is rather determined by whether or not any performance data has been associated with the session (i.e., performance data has been collected). If this is the case, then the session is considered "historical," otherwise it is considered a "future" session.

FIG. 40 illustrates the general workflow for creating, viewing and editing jump sessions.

When an administrator edits a future session by assigning equipment to the declared jumpers, the equipment is "checked out," i.e., made not available to other jumpers. After a jump session is performed and the performance data is imported, a depot manager can collect the equipment and then click a "return all equipment" button while editing the session to mark the equipment as returned and available to be lent out again. After a session is considered historical, editing the session (including equipping jumpers and making other modifications) does not affect the status of equipment. Hence, only the "return all equipment" functionality actually marks equipment as available. This allows for administrators to make corrections to historical sessions while not affecting the workflows of other future sessions and the availability of equipment.

The PDR devices 110, 210, 310 can be accessed both over USB 340 and over a Wi-Fi wireless connection 403. When the device is connected via USB 340 to a computer, it is shown as a standard USB mass storage drive and its contents can be accessed via the file system. Furthermore, the contents of PDR devices 110, 210, 310 can be accessed over a wireless network 403 using the FTP server built into the device.

Figure 41:
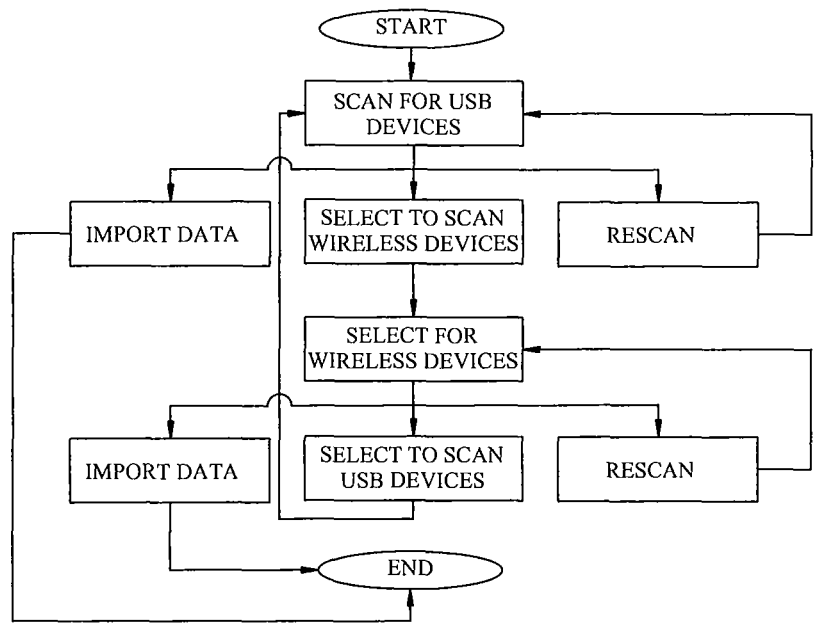
FIG. 41 is a block diagram showing the work flow for scanning for USB devices or wireless devices.

Syncing the PDR's sensor data is typically an action performed by an administrator. We separate between the USB and the wireless mode. Hence, the user can either scan for USB devices 340 or wireless devices 403. FIG. 41 shows the overview of this workflow.

Figure 42:
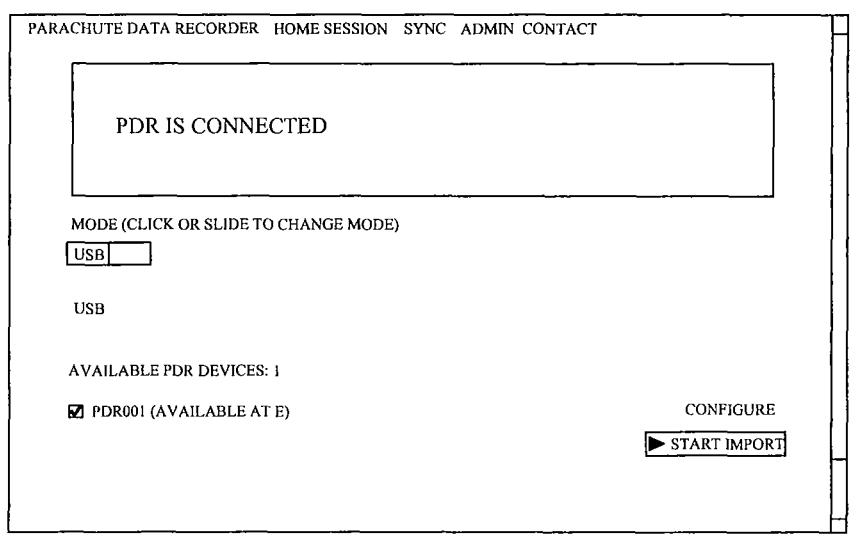
FIG. 42 is a screen shot showing the PDR connected via USB.

When USB devices 340 are scanned for, the software tries to find all the "root" devices attached to the computer in question (how this is done is platform specific, but we are assuming a Windows platform here). Root devices include hard-drives or any mounted USB devices 340 with a file system which are searched for config.pdr files. The availability of this file may identify the root device in question as a PDR device. Next the configuration file is parsed to get the device ID. If this is successful, the device is identified as a PDR device and added to the list of found devices. See FIG. 42 for an example of a PDR device found via USB.

Figure 43:
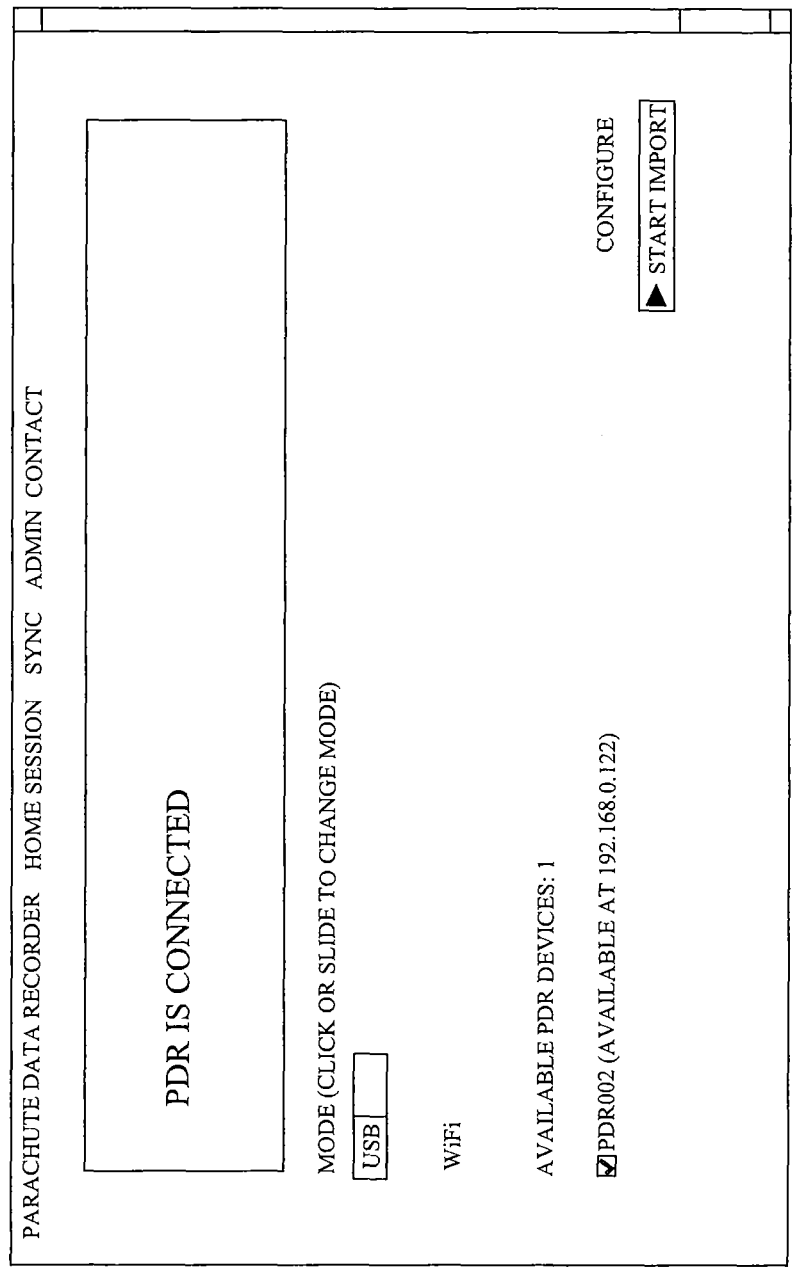
FIG. 43 is a screen shot showing the PDR connected via Wi-Fi.

To scan for devices over a wireless network we need the network to scan and the range of IP addresses to scan. An administrator can configure this in the software by providing a range of IP addresses. This is specified as e.g., "192.1681.*". This means that 256 addresses will be scanned, ranging from 192.168.1.0 to 192.168.1.255. In one embodiment of the system, only the last part of the IP configuration can accept a wildcard (*). When saved, this information will be stored in a Java properties file named pdrweb.properties. For each IP address in the range, it is attempted to connect to the IP via FTP (port 21). If the connection is successful, an attempt to download (using the "RETR" command) the configuration file config.pdr is made. If this is successful and the file can be parsed to retrieve the device ID to be added to the list of found devices. An example of a PDR device found via Wi-Fi is shown in FIG. 43.

The open-source FTP library ftp4j at http://www.sauron-software.it/projects/ftp4j/ can be used to interact with the FTP server on the PDR devices.

For each scanning mode (USB 340 or wireless 403), when the list of found devices has been retrieved, they can be displayed to the user in a list. Each device in the list can be checked or unchecked to indicate whether the device should be included when trying to import sensor data from the device.

After scanning for devices over USB 340 or wireless 403 and displaying the list of found devices to the user, the user can optionally click to configure any of the found devices. Doing so opens up a separate page where the user can easily change any of the values in the configuration file.

After scanning for devices, it is important to remember where the path was found. In the case of USB 340, the path is a file system path, i.e., "e:/" or "f:/" depending on the location of the USB device. In the case of wireless 403, the path is the IP address where the device was found. Using this path we can directly retrieve the configuration file (config-.pdr), parse it and populate the UI with the contents. Again, how we retrieve the configuration file depends on the format of the path. If the path is a valid IP address, the configuration file is accessed using the ftp4j library, and if the path is a valid file path, it is retrieved and parsed using the file system. A screenshot for configuring a PDR device is shown in FIG. 44.

After the user has made any modifications to the configuration and clicks "Save," the file is written back from where it was fetched (over the file system in the case of USB and using the FTP command "STOR" in the case of wireless).

An underlying SQL (MySQL implementation) database stores all the user and performance data. The Grails framework: Grails Object Relational Mapping (GORM) database layer (which is implemented using Hibernate) can be used. The GORM layer allows specifying database tables as class objects and can automatically create and update the database tables. GORM also provides functionality to query the stored data using standard object-oriented access methods.

The database used is configured in the conf/DataSource-.groovy class. Alternatively, the database access configuration can be overridden by providing a $HOME/.grails/pdrweb-config.groovy file. This second alternative makes it easy to override the database configuration when the application has already been deployed.

In the sections below, additional details of database models are provided and how data is being managed.

Figure 45:
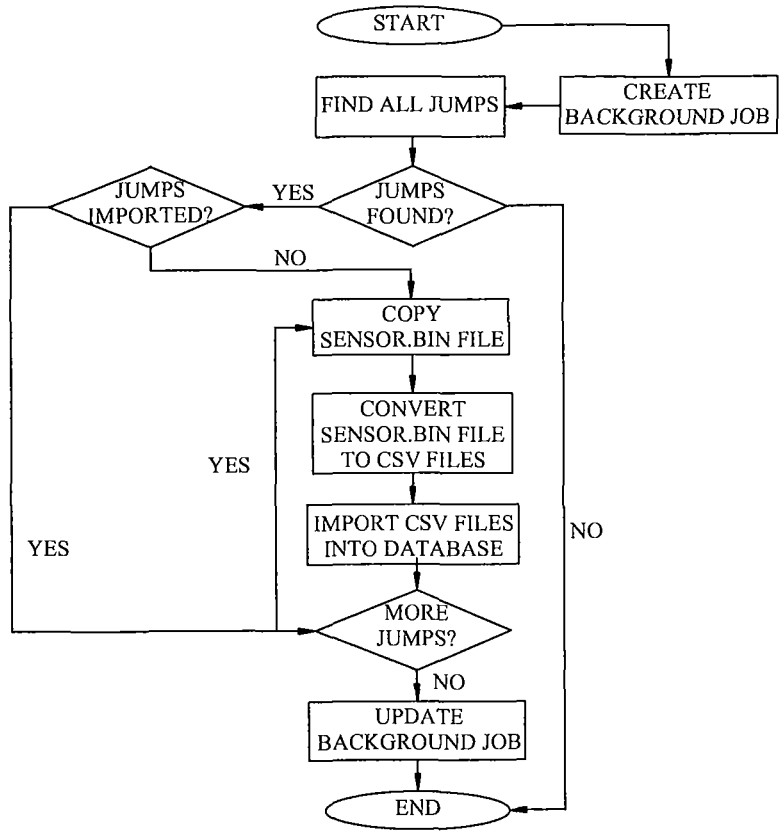
FIG. 45 is a general work flow diagram for importing data from the PDR device.

Once the importing of data is started from a device, the general workflow in FIG. 45 is followed.

If no jumps are found, there is nothing to do. Jumps are found by iterating over the file structure on the device (either directly if over USB or via FTP if accessing the device over the wireless network). The sensor data are stored in SENSOR.BIN files in a pre-defined folder structure:
/DEVICEROOT/[DAYFOLDER]/REC_[JUMP NUMBER]/SENSOR.BIN The DAYFOLDER is formatted according to "yyyyMMdd" where "yyyy" is the year, "MM" the month and "dd" the day of the month. For example, the folder may be named "20130324". In such day folders, there may be any number of jump folders with the naming convention "REC_[JUMP NUMBER]" where JUMP_NUMBER is a non-negative integer ({0, 1, 2, 3, . . . }). For each jump there is a SENSOR.BIN file that contains the recorded sensor data.

For each SENSOR.BIN file found, it is checked to see if the jump has already been imported. A jump is uniquely identified by the tuple <device id, day of jump, jump number>. If the jump has already been imported, it is skipped. If it has not been imported, the SENSOR.BIN file is copied from the device onto the local hard drive. Once copied, the SENSOR.BIN file is converted into a set of Comma Separated Value (CSV) files. Each CSV file contains the data from a specific sensor on the PDR device. For each generated CSV file, all its data is inserted into the database.

Each sensor type has its own table in the database. Each such sensor data table contains three common columns:
1. id (The ID of the record)
2. pdr (The PDR device ID)
3. day (The day of the jump)
4. jump (The jump number)

Figure 46:
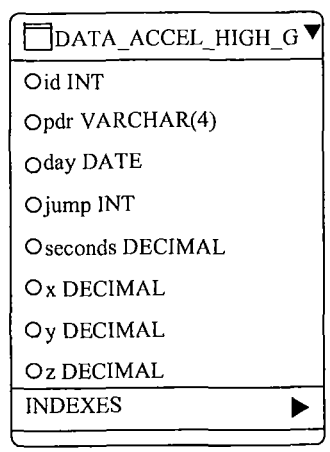
FIG. 46 shows the table definition for high G acceleration data.

The remaining columns in each sensor data table are specific to the particular data that is being stored. FIG. 46 shows the table definition for the High G acceleration data.

As can be seen in FIG. 46, the High G Acceleration data has four data specific columns:
1. seconds (the number of seconds from midnight on the particular day)
2. x (the x-axis value)
3. y (the y-axis value)
4. z (the z-axis value)

To insert the High G Acceleration data into this table, an efficient mechanism supported by MySQL is used to insert data from CSV files. The following SQL prepared statement is created to do this:
LOAD DATA INFILE [path to CSV file] INTO TABLE [table]
FIELDS TERMINATED BY ',' ([columns]) SET pdr=?, day=?, jump=?

The path to the CSV file is specified, as well as the table name and the columns that are specific to the sensor data type. The questions marks (?) are part of the prepared statement and are instantiated before the command is issued. They ensure that each data record has the appropriate data to allow it to be known where the data comes from. A concrete SQL statement would be:
LOAD DATA INFILE 'c:/data/accel_high_g.csv' INTO TABLE data_accel_high_g
FIELDS TERMINATED BY ',' (seconds, x, y, z) SET pdr=0001, day='2013-12-01', jump=1

This is a very efficient way of inserting data from CSV files into a MySQL database. The other sensor data database table definitions can be found in FIG. 47.

Despite using efficient methods to insert the data into the database, it might take some time to insert all the data; especially if the data files are large. To avoid locking up the application, these imports are done in background threads. A separate thread is created for each device. To allow the user to know how the import job is progressing, a job status object can be generated for each background thread. As the job is processing, progress status is updated (0-100%) and a jobs log with messages that describe that progress. This information is displayed to the user while the background job is processing. When the job is done, the progress bar shows that it is at 100% and the job's complete status flag is set to "true." FIG. 48 is a screenshot showing the progress of performance data importing.

Figure 49:
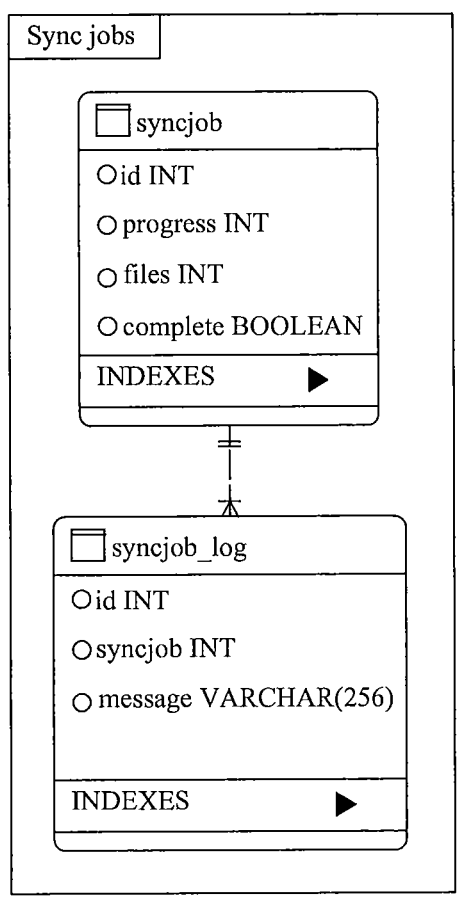
FIG. 49 is a database table structure for jobs and their logs.

The database table structure for jobs and their logs is shown in FIG. 49.

Once performance data has been imported and inserted into the database, the connection between sessions and jumps must be known, i.e., which session was an imported jump part of? In one embodiment, no automated reasoning is provided to determine this. Rather, the administrator must declare which jump sessions imported jumps should be part of.

Once this connection is declared, a hierarchical structure of a jump session can be represented and any associated performance data as:
Session
  Jumper 1
    [Link to view performance data]
  Jumper 2
    [no performance data—did not carry a PDR]
  . . . .

Figure 50:
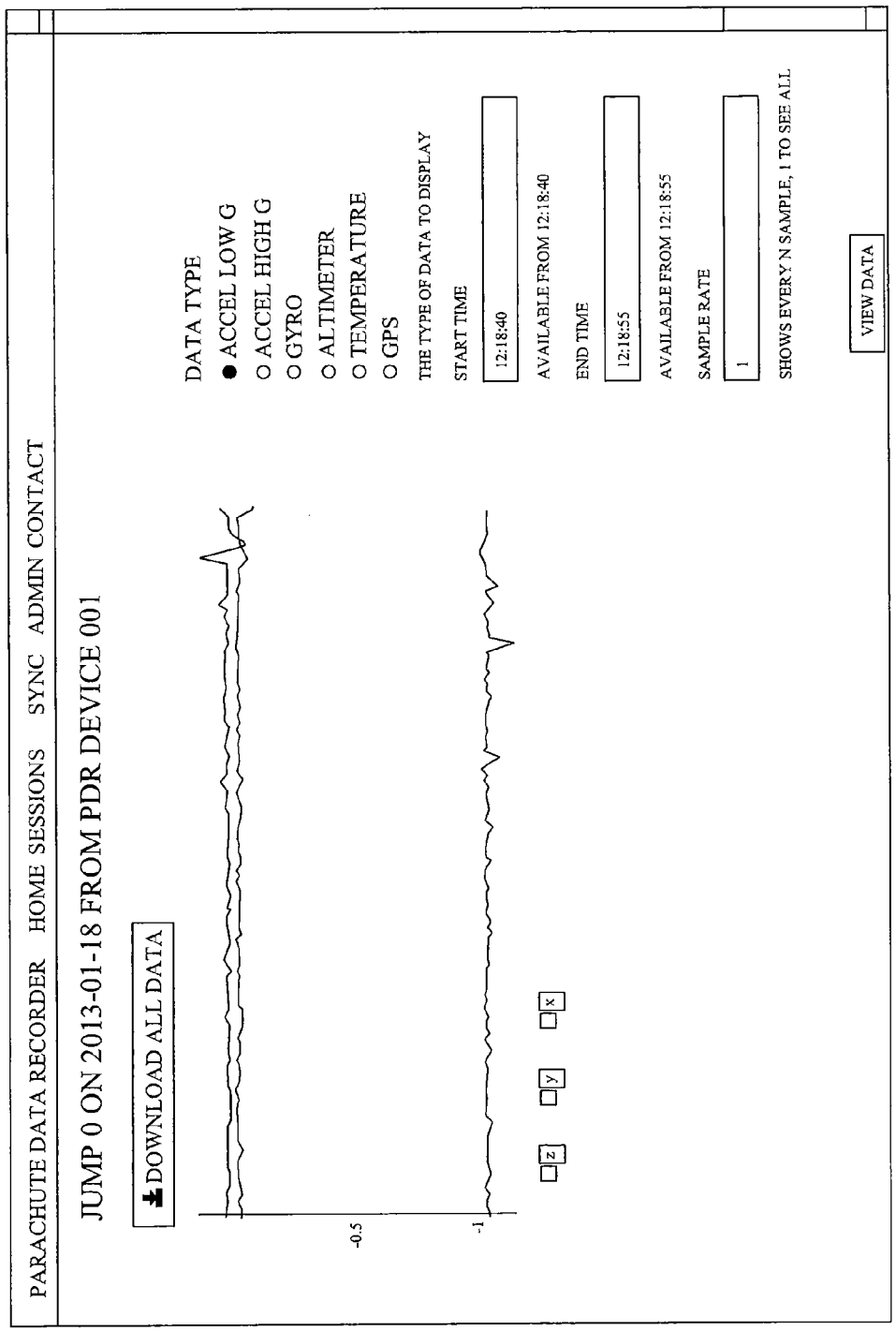
FIG. 50 is an example screen shot showing a sensor data previewing function.

The Web application provides a simple interface and plotting capability to preview sensor data (see an example in FIG. 50). The user can select:
The sensor type to view data from
The time window of data to view (i.e., start and end point)
The sample rate (i.e., how many data points to view)

The specified data is fetched from the database and displayed in the Web application. The Rickshaw JavaScript library is used to visualize the data. In this embodiment of the invention, no analytical capabilities are provided, but simply allow the user to view the data.

To support the full cycle of data management, all the data associated with a jump can be exported. All the performance data from the jump can easily be exported using a single click by pressing the "Download all data" button (see FIG. 50). Each sensor data type that is available for a jump is exported into a separate CSV file. When this is done for each sensor type, the CSV files are archived into a ZIP file and make this file available for download.

In a reversal of the way the data was imported from CSV files, the export is done using the following command:
SELECT [columns] INTO OUTFILE '[output file]'
FIELDS TERMINATED BY ',' LINES TERMINATED BY '\\n'
FROM [table name]
WHERE pdr=? AND day=? AND jump=? ORDER BY 'seconds'

The columns that should be exported is specific to the data type, the output file is given a name related to the sensor data type, and the table name again depends on the sensor type. The "pdr," "day" and "jump" values come from the specific jump from which the data is being exported.

A concrete SQL statement for High G Acceleration data can look as the following:
SELECT seconds, x, y, z INTO OUTFILE 'c:/data/accel_high_g.csv'
FIELDS TERMINATED BY ',' LINES TERMINATED BY '\\n'
FROM data_accel_high_g
WHERE pdr=0001 AND day='2013-12-01' AND jump=1
ORDER BY 'seconds'

The exported data can be used for further analysis.

In one embodiment, only limited visualization of the data is provided in a simple way of previewing the data. More robust visualization capabilities can be added to the PDR software.

In one embodiment, no analytic capabilities are provided in the PDR software; however, as users may want to perform analytics on the data, preliminary algorithms have been developed to extract event markers and information of interest to parachute designers, users, commanders, and instructors. These analytical capabilities can be added to the PDR software.

In one embodiment, finding PDR devices over the wireless network requires knowing what network to scan, and what range of IP addresses to scan. In another embodiment, it can be specified exactly which IP addresses to scan in a compact way, i.e., to be very precise in what range of addresses to scan. Scanning the network and finding USB devices can be time consuming, so scanning only the required IP address for devices can speed up the response time of the application.

In one embodiment, the PDR software assumes an intended workflow and an order of performed steps, and if these steps are not followed, errors may occur, but it is possible to improve error handling if the workflow is not followed.

In one embodiment, PDR devices are identified by a hexadecimal number while the application currently treats the IDs as strings, but a common way of handling device IDs can also be used.

In one embodiment, the Parachute Data Recorder (PDR) stores data measured by two sets of tri-axial accelerometers 404*a,b* (i.e., "low-g" limited at 4 gs and "high-g" limited at 16 gs), a suite of tri-axial gyros 406, a temperature gauge, and a pressure sensor (for calculation of altitude). Such data are integrated into a single unit to provide basic physical information about all stages of a parachute jump, namely: jump from the aircraft; free-fall; parachute deployment and opening; descent and landing. This physical information includes fall (or free-fall) duration, parachute deployment and opening durations, and parachute descent duration; rates of altitude loss; accelerations and decelerations, as well as its rotational rates.

Figure 51:
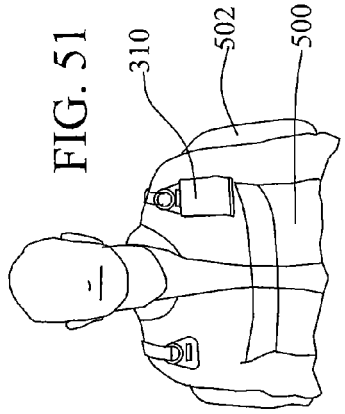
FIG. 51 shows a jump suit used during jump trials including the PDR device.
Figure 53:
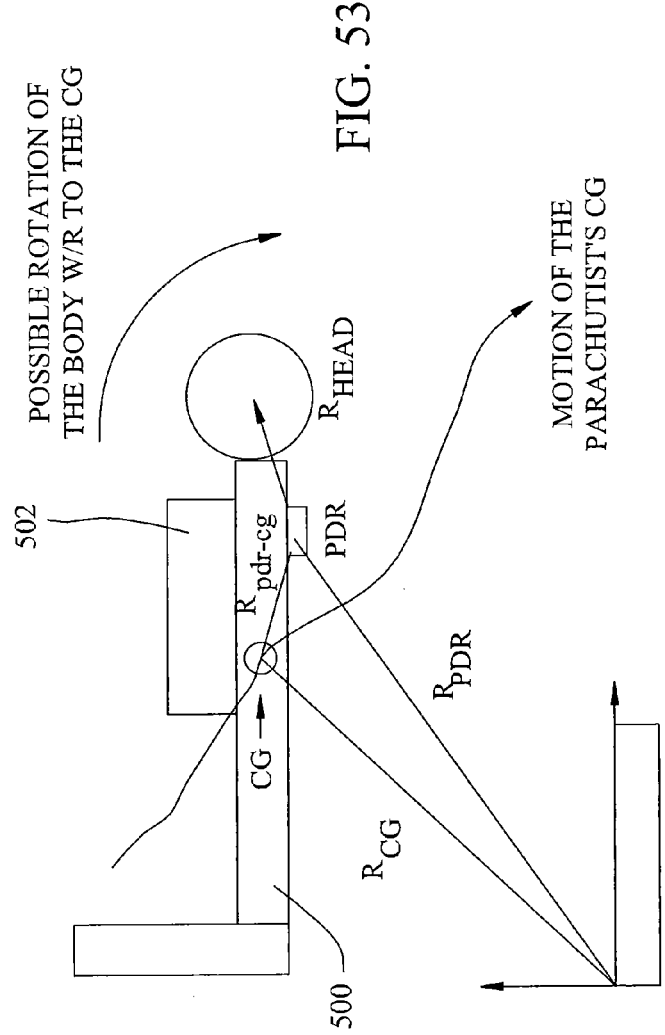
FIG. 53 is a sketch of motion and position vectors of the PDR device and a parachutist during free-fall as described with respect to a reference frame fixed on the ground.

Some of the raw PDR data, like event durations and altitudes, can be directly applied to the dynamics and kinematics of the parachutist (or "jumper") 500 (FIG. 51). However, most of the PDR output necessitates extensive analysis and interpretation before being relevant to a jumper's body motions and dynamics. Such is the case with PDR accelerations and gyro rates, which at face value only apply to PDR translations and gyrations. As sketched in FIG. 53, connecting PDR device 310 and jumper body 50 motions require coordinate and axes transformations from the PDR's reference axes to other reference frames fixed on both the parachutist's center of gravity (CG) and to the ground.

Figure 52:
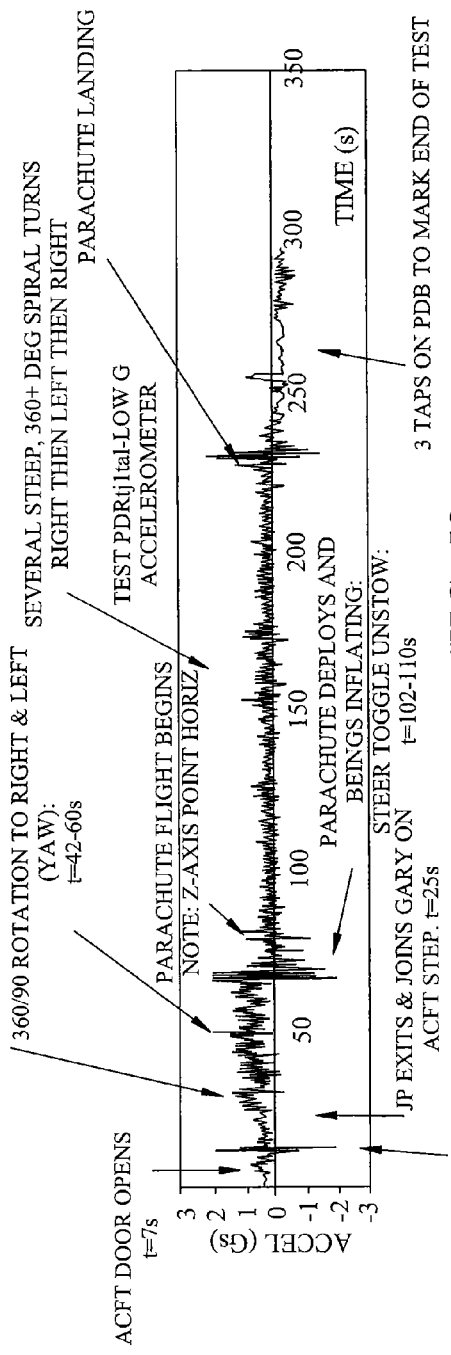
FIG. 52 is a printout of data recorded by the PDR device's low-g accelerometer output during a jump.
Figure 54:
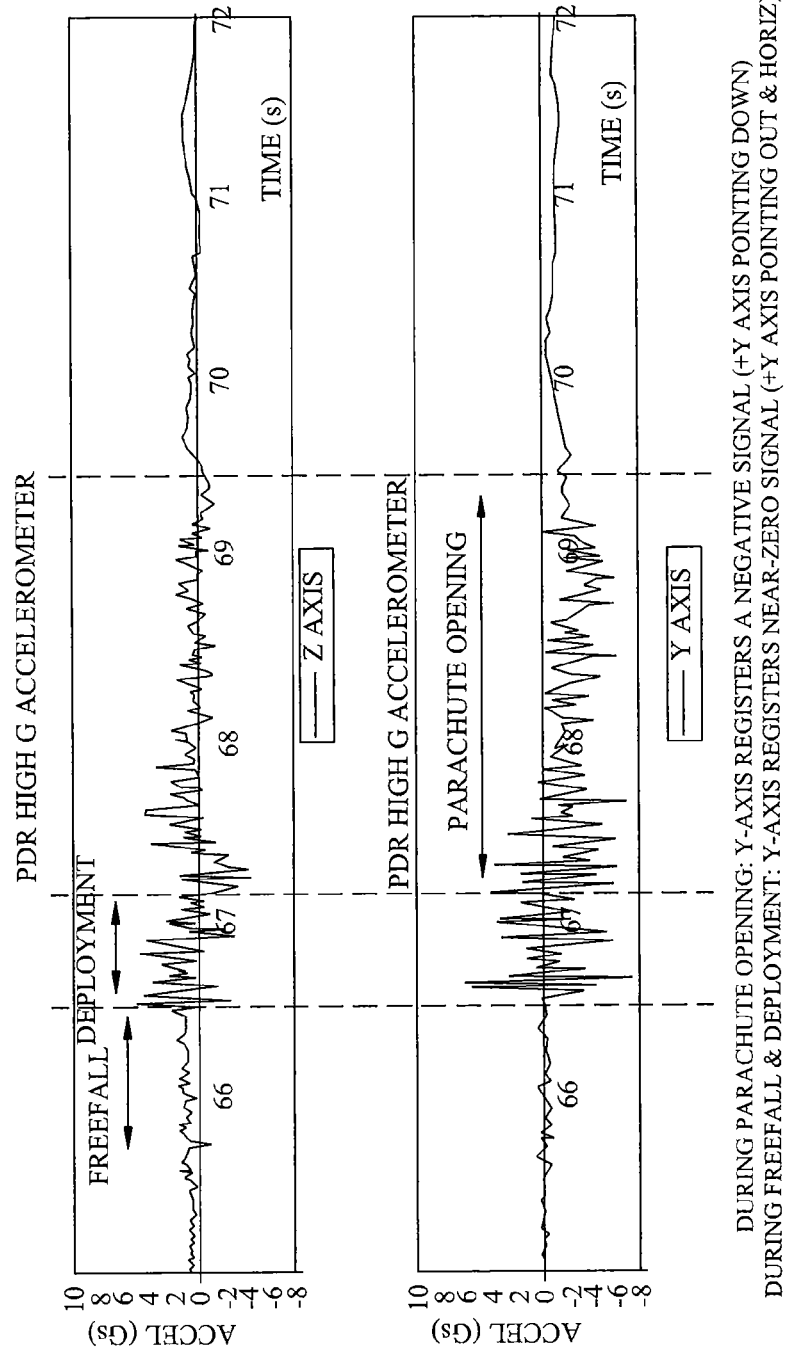
FIG. 54 shows parachute deployment and opening events as recorded by the PDR device high-g accelerometer and the output data therefrom.
Figure 55:
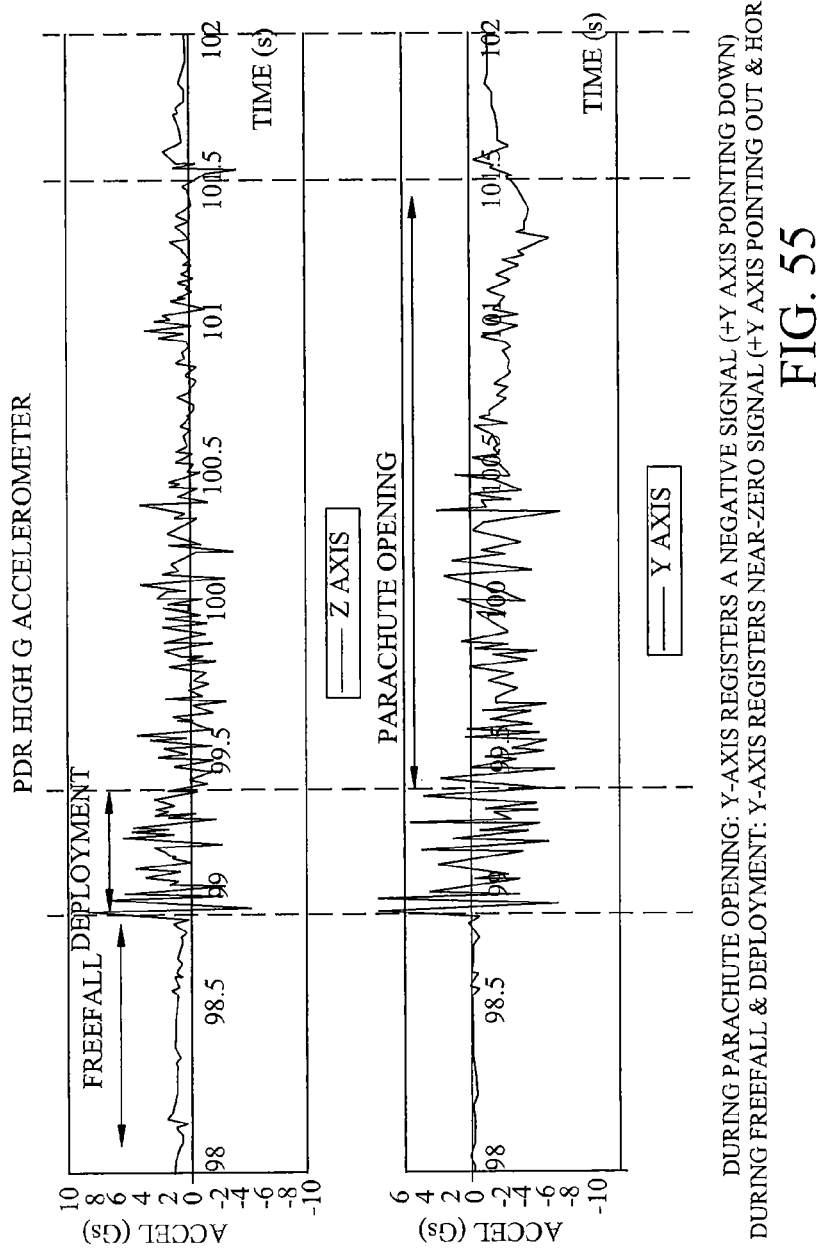
FIG. 55 shows parachute deployment and opening events as recorded by the PDR device high-g accelerometer and the output data therefrom for another test jump.

As shown in FIGS. 52, 54 and 55, the PDR accelerometer 404a,b and gyrometer 406 signals are distinct enough during each stage of a jump to provide a set of useful markers by which the duration of these stages can be evaluated. Duration is a key element here, by which the external forces applied on a parachutist can be estimated via the Momentum-Impulse Theorem (or MI theorem for short). This is particularly true—and important—during the parachute opening stage when the loads on the body are at their highest.

The MI theorem links, via Newton's $2^{nd}$ law of motion, the momentum change during time interval $t_f - t_i$ of a parachutist's body 500 (here represented by a point mass located at the body's CG), to the time integral of the net external forces acting on the body. Focusing on the momentum and force components along the fall trajectory of the parachutist, one has the following expression, which involves the time-varying net force $F_{net}(t)$ and the body weight component tangential to the trajectory):

$$mV_f - mV_i = \int_i^f -F_{net}(t)dt + \int_i^f W\cos\theta dt \quad (2)$$

Here m and W refer to the mass and weight of the jumper, respectively. The flight angle $\theta(t)$ is defined so that a 0°-value corresponds to a parachute-payload system falling straight down, and a 90°-value to a system traveling horizontally (and to the right). The speeds $V(t_i) \equiv V_i$ and $V(t_f) \equiv V_f$ refer to the jumper's tangential speeds at times $t_f$ and $t_i$, respectively. Note that with this notation, both $V_i$ and $V_f$ are positive as long as 0°<$\theta(t)$<90°. Moreover, $-F_{net}$ corresponds to the tangential component of the total force (i.e., besides weight) applied on the body 500: namely, body drag during free-fall, or body drag plus riser pull during parachute deployment and opening (note that per FIG. 56, $F_{net}$ is opposite to V, hence the negative sign in equation (2).

Although equation (2) is exact and applies to any time intervals $t_f - t_i$ of relevance to any of the five stages of a jump, its use will be limited here to parachute 502 opening, with $t_f - t_i$ corresponding to the beginning and end of this particular stage.

Noting that dividing the integral of $F_{net}$ by the interval $t_f - t_i$ in equation (2) yields an equation involving the average force $F_{aver}$, one has:

$$mV_f - mV_i = -F_{aver}(t_f - t_i) + \int_i^f W\cos\theta dt \quad (3)$$

This result is also exact. In what follows we are interested in two specific types of trajectories, namely purely vertical and purely horizontal trajectories, for which equation (3) simplifies greatly (and exactly).

$$mV_f - mV_i = -F_{aver}(t_f - t_i) \text{ horizontal} \quad (4)$$

$$mV_f - mV_i = (-F_{aver} + W)(t_f - t_i) \text{ vertical} \quad (5)$$

When applied to parachute 502 inflation, these two expressions actually yield lower and upper bounds on parachute drag (and thus averaged riser force).

Accordingly, the values of the time interval $(t_f - t_i)$ and speed increment/decrement $(V_f - V_i)$, as well as of the weight W, will bound the average (tangential) net force. Since the speed increment/decrement isn't directly measured by in this context of using PDR data as event markers, it is assumed that the system decelerates significantly during inflation (yielding $V_f \ll V_i$)—a scenario that is valid for personnel or cargo parachutes (or more generally "landing" parachutes). This assumption then allows recasting equations (3) and (4) and (5) as:

$$F_{aver} \approx \frac{mV_i}{(t_f - t_i)} \text{ (horizontal)} \quad (6)$$

$$F_{aver} \approx \frac{mV_i}{(t_f - t_i)} + W \text{ (vertical)} \quad (7)$$

Note that this result does not apply to stabilization parachutes (or "drogues") which typically do not decelerate a great deal during inflation. At this point, the MI theorem shows that an average force estimate can be obtained from knowing: 1) the mass and weight of the jumper's body; 2) the fall speed just prior to deployment; and 3), the duration of the opening stage, as inferred from the raw PDR accelerometer data used as event markers (see FIGS. 54 and 55). Given that the weight, jump altitude and jump type are data entered into the "configuration file" of the PDR prior to jumping, the value of the mass m and fall speed $V_i$ can also be estimated by the PDR, and the average force thus calculated from the time intervals, albeit post-jump (Note: here m=W/g with g=32.17 ft/s²; $V_i \sim (2 W/\rho \cdot 10 \text{ ft}^2)^{0.5}$ for a free-fall, or $V_i$=known measured number (TBD) for static line jumps from C-130 or C-17 aircraft).

The "peak" or maximum riser force sustained by the jumper ($F_{max}$) can also be estimated from equation (1), this time via the use of two approximations, rather than just one as with $F_{aver}$. Using $F_{max}$ (besides weight) in equation (2) yields:

$$mV_f - mV_i = -F_{max}(t_f - t_i)I_F^{if} + \int_i^f W\cos\theta(t)dt \quad (8)$$

where $$I_F^{if} = \int_i^f \frac{|F_D(t)|dt}{F_{max}(t_f - t_i)} \quad (9)$$

Parameter $I^{if}$ is the so-called drag integral which contains the information related to the shape of the $F_{net}$-vs.-t curve, effectively a measurement of the (normalized) area under that curve. This integral is such that the force evolutions involving a nearly constant force during the entire time interval is characterized by $I^{if} \sim 1$, while evolutions characterized by a dominating triangular peak yield $I^{if} \sim \frac{1}{2}$. For unreefed "round" or near-hemispherical personnel parachutes 502a such as the (US Army) T-10 and (USAF) C-9, one finds $I^{if}$~0.50-0.65; and for personnel slider-reefed parafoils (including the US Army MC-4) and slider-reefed round parachutes (Butler HX-600), one has $I^{if}$~0.40-0.50. Assuming again $V_f \ll V_i$ (thus restricting to personnel canopies), and focusing again on purely horizontal and vertical 0trajectories, equation (8) and the $I^{if}$ values prescribed in known references yield the following results:

Unreefed round parachute types (incl. Army T-10):

$$F_{peak} = F_{max} \approx \frac{mV_i}{(t_f - t_i)(0.50 \text{ to } 0.65)} \text{ (horizontal)} \quad (10)$$

$$F_{peak} = F_{max} \approx \frac{mV_i}{(t_f - t_i)(0.50 \text{ to } 0.65)} + W \text{ (vertical)} \quad (11)$$

Slider-reefed parafoils and round types (incl. Army MC-4 and possibly the Army T-11):

$$F_{peak} = F_{max} \approx \frac{mV_i}{(t_f - t_i)(0.40 \text{ to } 0.50)} \text{ (horizontal)} \quad (12)$$

$$F_{peak} = F_{max} \approx \frac{mV_i}{(t_f - t_i)(0.40 \text{ to } 0.50)} + W \text{ (vertical)} \quad (13)$$

Here again the time interval is obtained from the accelerometer data used as event markers (FIGS. 54 and 55) and from all other data pre-calculated by the PDR using its "use file." Note that equations (12) and (13) may be applicable to the Army T-11 which is also a slider-reefed canopy very much like the hemispherical Butler HX-600. Although further load-cell testing with a T-11 needs to be implemented to get the needed drag integral data, Applicant believes that equations (12) and (13) could be a good educated guess and thus a good starting point for this particular parachute. (Note: the US Army may already have such load cell data, obtained during the R&D phase of the T-11 program (i.e., ATPS Program)).

Average and peak riser forces (neglecting body drag) sustained during the test jumps pdrtj1tal and pdrtj2ta can be quickly calculated from equations (7) and (13) since both parachute deployment and opening occurred along a purely vertical fall trajectory. This simple calculation is implemented in the Excel spreadsheet. FIGS. 57 and 58 show the typical outputs of the spreadsheet. This type of free-fall parachute jump will contrast with static-line jumps for which the trajectory is ballistic (i.e., 2-dimensional), and for which 4a,b and 8a,b need to be used to get bounded estimates of the forces. The input parameters for jumps pdrtj1tal and pdrtj2tal are as follows:

W=2201 bs (as weighted on a scale) and using m=W/g with g=32.17 ft/s$^2$ yields m=6.5351

Deploy altitude=4000 to 5000 ft MSL (yielding $\rho$=0.00211 to 0.0020 sl/ft$^3$)

The fall speed prior to parachute opening is usually very close to the fall rate during deployment, which itself is close to the speed of free-fall. Being standard skydiving jumps, the fall rates sustained during the free-falls of pdrtj1tal and pdrtj2tal are thus expected to be in the range of 100 to 110 mph. Converting such free-fall speeds in feet per second yields:

$V_i$=147 to 162 ft/s

Naturally, and because of the purely vertical nature of the trajectory, the fall rates can also be obtained from the PDR pressure data when the free-fall is stable, namely during time intervals 53.56 s–67.11 s (pdrtj1tal) and 73.89 s-98.85 s (pdrtj2tal). This PDR data suggest the following fall rates at the time of parachute deployment:

$V_i$=159 ft/s (pdrtj1tal) and 166 ft/s (pdrtj2tal)

i.e., values which are quite consistent with published values. The falls speed uncertainties in both types of estimates arise from the changes in body shape that occur as results of maneuvering.

The information on parachute opening duration needed in equations (6)-(7) and (12)-(13) is provided here by the PDR accelerometer 404a,b data, which suggest $t_f - t_i$=2.5 s (±0.10 s) for both pdrtj1tal and pdrtj2tal (see y-axis data, in FIGS. 54 and 55). It should be noted that during deployment, the body and PDR rotate from a horizontal to a vertical attitude; then both PDR device 310 and parachutist body 502, 502a remain vertical during parachute opening.

Given the initial speeds (V) from the PDR data and drag integral ($I^{if}$), using equations (7) and (13) yields the average and peak riser forces in the range of $F_{aver}$~655-6741 bs and $F_{peak}$~1089-13551 bs.

The force information just obtained can be easily translated into decelerations and compared to the PDR acceleration data, given the simple and vertical nature of the trajectory:

$$ma_{aver} \approx F_{aver} - W$$
$$ma_{peak} \approx F_{peak} - W$$ (vertical axis pointing up)

Figure 59:
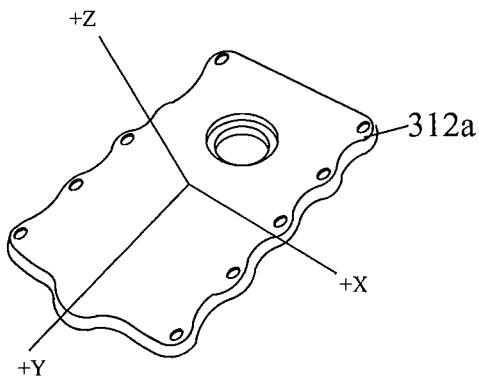
FIG. 59 shows the PDR device accelerometer access convention on the front cover of the PDR device.

From equation (7), one gets $a_{aver/g}$ values displayed in FIG. 58, i.e., in the range of $a_{aver}/g$~1.98 to 2.06 g's and $a_{peak}/g$~3.95 to 5.16 g's. The comparison of these numbers with PDR Y-axis accelerometer (FIGS. 54 and 55) is straightforward, that is, once the axis conventions used in equation (7) and with the PDR are first identified. Using Applicant's convention (FIG. 59), and the fact that the +Y axis pointed downwards during parachute opening (see PDR emplacement on the harness in FIG. 51, where the "on" button is facing out and up), one uses the formula $a_{pdr}^{called}/g=(a_{pdr}^{raw\ output}/g)+1$ to get the true (or "called") acceleration from the raw data in this particular PDR orientation. And since the reference +Y axis is opposite to the axis used in equation (7), one has $a_{eq,9}/g = -a_{pdr}^{called}/g$. From these conventions, we have $a_{eq,9}/g = -a_{pdr}^{called}/g - (a_{pdr}^{raw\ output}/g) - 1$ or $a_{pdr}^{raw\ output}/g = -(a_{eq,9}/g) - 1$ i.e., results that "predict" the raw PDR Y-axis accelerometer data reading as:

$a_{pdr}^{raw\ output}/g|_{aver}$~−2.98 to −3.06 g's and $a_{pdr}^{raw\ output}/g|_{peak}$~−4.95 to −6.16 g's These numbers are consistent with the averaged PDR Y-accelerometer data during parachute opening (FIGS. 54 and 55):

Pdrtj1tal: $a_{pdr}^{raw\ output}/g|_{aver}$~−2.62±0.69 g's (i.e., data with 1.38 standard deviation)

and

Pdrtj2tal: $a_{pdr}^{raw\ output}/g|_{aver}$~−2.51±0.96 g's (i.e., data with 1.93 standard deviation)

Known raw peak deceleration data also compares favorably with the results of equations (12)-(13).

Ultimately, PDR accelerometer output yield the accelerations sustained by the body 500, and by virtue of Newton's $2^{nd}$ law of motion, the resultant force at play. With regards to the latter, PDR accelerometer data potentially offer a more complete and more accurate calculation of the riser forces. But as outlined below, the required analysis is significantly more involved. Moreover, such an analysis requires further characterizations of the system (i.e., supplemental input data).

Figure 56:
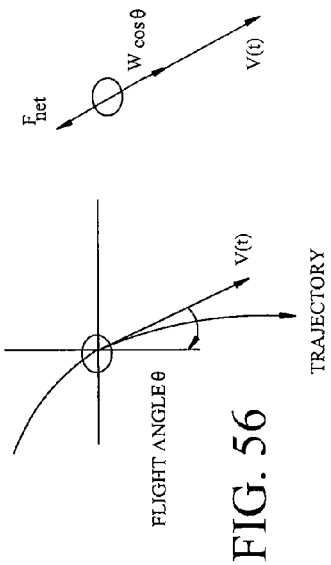
FIG. 56 shows a diagram of trajectory parameters for a parachute and payload.

Because the PDR will most likely be located a distance away from any parachutist 500 center of gravity (CG), its accelerometer and gyro data yield direct information not of the body but of the PDR's own translations and gyrations (see FIG. 56). Obtaining motion information of the jumper 500 CG, or of any other body part (such as the head), will require coordinate and axes transformations from the PDR's reference axes to other reference frames located on the body's CG and on the ground (FIG. 56).

Calculating the motions of a parachutist's CG (here assumed as "known" or at least "knowable") is achieved via the calculation of the position vector $R_{CG}$ shown in FIG. 56. This step first requires knowing with some accuracy the location of the PDR with respect to the CG, resulting in the vector $R_{pdr-cg}$ which is then used in the calculation of $R_{CG}$ via a vector addition operation ($R_{CG}=R_{pdr-cg}+R_{PDR}$). The CG acceleration calculation follows from using the PDR acceleration data ($a_{PDR}$) in the acceleration vector identity $a_{CG}=a_{pdr-cg}+a_{PDR}$, with the acceleration $a_{pdr-cg}$ of the straight line joining the PDR and body CG ($R_{pdr-cg}$) calculated from the tilting rate of the PDR accelerometer axes as obtained from the PDR gyros 406.

Figure 60:
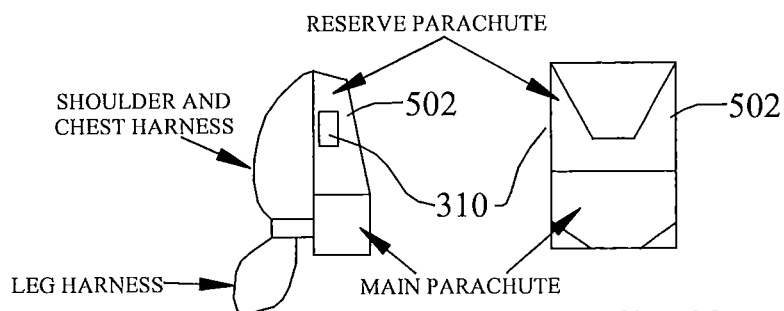
FIG. 60 shows front and side views for one place of locating the PDR device on a parachute or harness.

In principle, the acceleration algorithm just described can work for any PDR axes orientations. However, simplification in the mathematics can be achieved if the PDR axes are fixed on the parachute equipment 502 in ways to be aligned with the main symmetry axes of the body 500 as well as with the gravitational field. One way is to align one of the axes with the jumper's head-to-feet line; another along the line formed by the jumper's extended arms; and the third along a direction orthogonal to the first two axes. Attaching the PDR to the front section of the shoulder harness as shown in FIG. 51 would approximately meet this requirement. Alternatively, placing the PDR device 310 in a pouch sewn externally to the side of the reserve container would work as well (and perhaps more accurately), but only whenever the reserve parachute remains unused (FIG. 60). Yet another location, i.e., inside the reserve container and against the back pad, has been mentioned in previous discussions and would offer an even better alternative.

Figure 61:
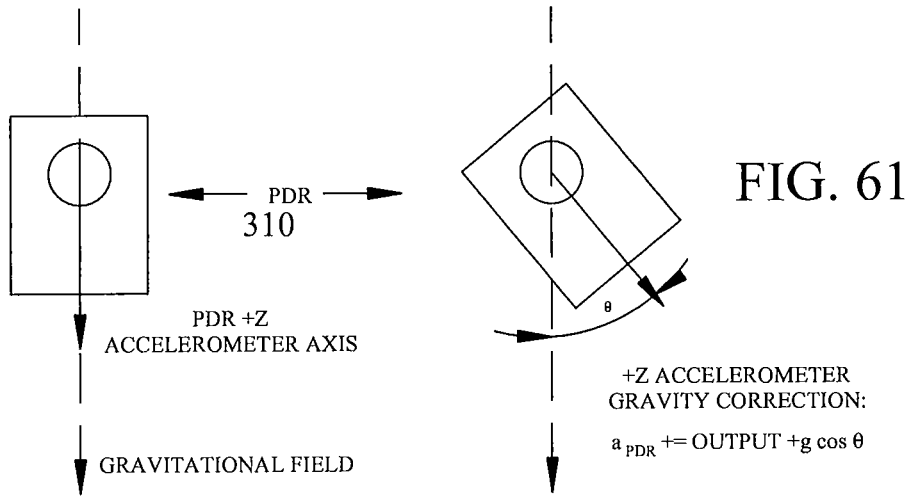
FIG. 61 shows measurement of the angle of the PDR relative to the Z axis for gravity correction of the PDR accelerometer.

Knowing the direction of the gravitational field is necessary to figure out the axes of the reference frame fixed to ground as well as to remove the effects of gravity from the PDR acceleration outputs. The latter is important since gravity yields non-zero accelerometer readings even when the PDR sits on a table at rest or moves at constant velocity. Thus the knowledge of the value of the angle θ (FIG. 61), as well as the other angles measured for the +X and +Y accelerometer axes, is needed at all times in order to gravity-correct the PDR accelerometer at all times (FIG. 61). These angles can be computed over time using the PDR gyro data, as long as the orientation of the PDR axes with respect to the gravity field is known at some time prior to the jump. Thus a calibration step is needed, after the unit is powered up but prior to the jump itself. Such a step can be as simple as an agreed-upon number of taps on the PDR unit by the jumper or jumpmaster, with the jumper in a standing position.

Figure 62:
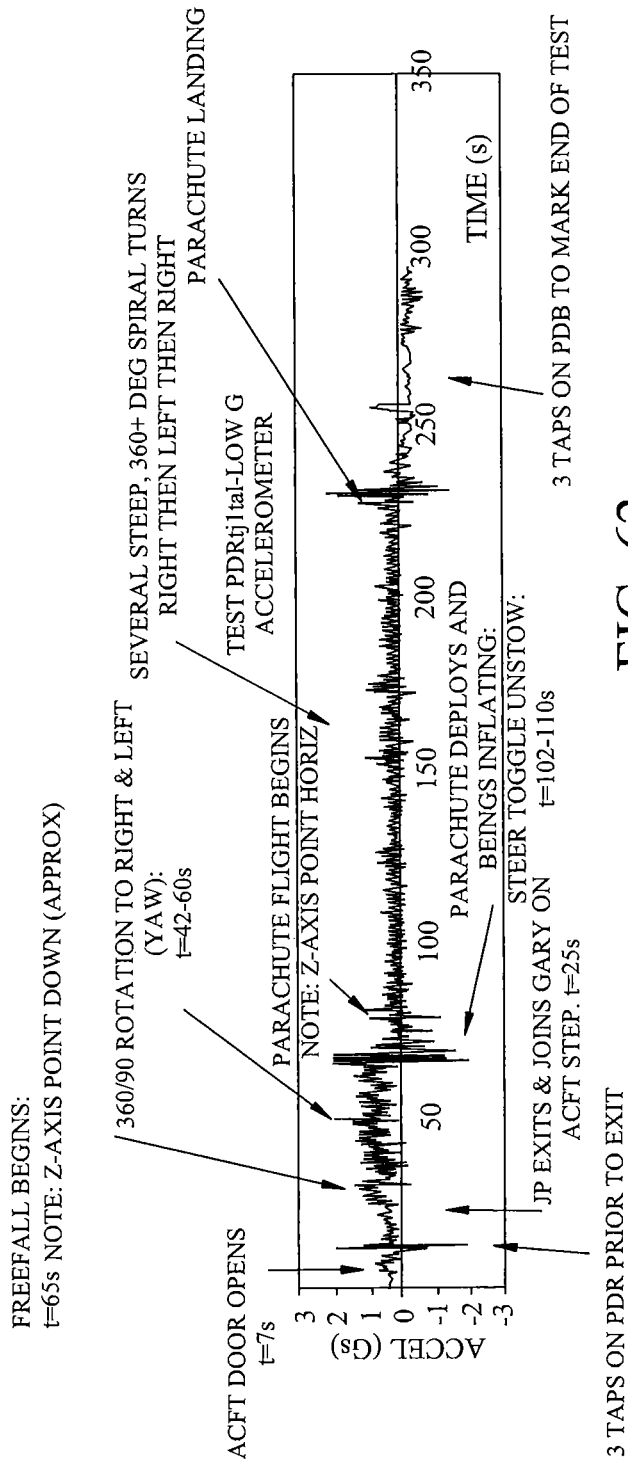
FIG. 62 is the Z axis accelerometer output during one test jump.
Figure 63:
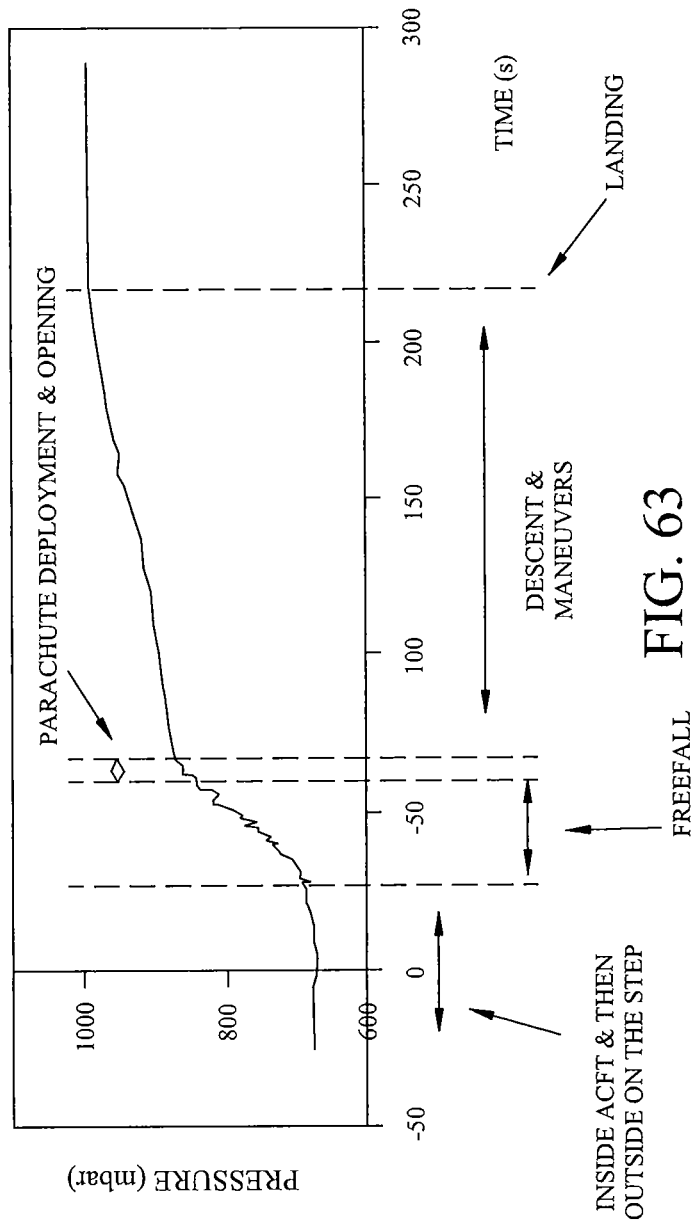
FIG. 63 shows the pressure data output of the PDR during the test jump related to FIG. 62.

A typical PDR pressure data output is shown in FIGS. 62 and 63, in comparison with the output of the Z-axis high-g accelerometer. Unlike with the accelerometer data, the pressure readings among the various stages of a jump are different enough to track the duration of most, but not all events. For example, the change of slope is particularly striking during parachute deployment and opening. During deployment, the fall rate of the jumper remains close to that of the free-fall, but then decreases rapidly when the parachute begins inflating. On the other hand, and unlike accelerometer data, pressure data is not that particularly useful in discriminating the various parafoil flight maneuvers that could be executed during the descent, although it becomes obvious at the moment of landing.

Pressure data is more useful for the calculation of the vertical component of the fall rate when the trajectory is 2- or 3-dimensional (or "ballistic"). When the trajectory is purely vertical, the vertical component of the fall rate becomes the fall rate. Both calculations can be carried out using the methods described below.

Although discussed in the context of long duration freefall by skydivers, the following methodology may also be used to calculate the vertical component of the fall rate in the ballistic trajectories of static-line jumpers.

Because the atmospheric pressure is correlated with altitude H (Mean Sea Level reference), it is possible to extract parachutist fall rates (i.e., altitude loss rates) from pressure rates. As shown in equation 1 below, the fall rate ($V_{freefall}$) is measured from the PDR pressure data (P), in particular from the rate dP/dt of pressure change per unit time during the free-fall, an input that is directly extracted from the PRD pressure data (see FIGS. 64 and 65). But the calculation requires also knowing the variation of atmospheric pressure as a function of altitude (dP/dH)—an input that isn't known from the PDR data stream. Such pressure profile may be obtained from daily/hourly measurements at locations nearest to the jump. Alternatively, one can use the profile of the so-called Standard Atmosphere which is mathematically described by equations (15) and (16) used here.

$$\frac{dP}{dt} = \frac{dP}{dH}\frac{dH}{dt} = \frac{dP}{dH} V_{freefall} \tag{14}$$

$$\frac{dP}{dH} = \frac{(-AB)}{(1-AH)} P \tag{15}$$

$$P = P_0(1-AH)^B \tag{16}$$

$$A = \frac{LH}{T_0}$$

$$B = \frac{gM}{RL}$$

where:
$P_0$=sea level standard atmospheric pressure (1013.25 mbar)
L=temperature lapse rate (0.0065° K/m
$T_0$=sea-level standard temperature (288.15° K)

g=acceleration of gravity at the Earth's surface (9.81 m/s²)

M=molar mass of dry air (0.02896 kg/mol)

R=universal gas constant (8.31447 J/(° K mol)

Note that equation (16) is valid for altitudes below 36,089 ft (MSL) where the temperature decreases linearly with height. Above that level both pressure and dP/dH decrease exponentially with height.

The value of $V_{freefall}$ during test jumps pdrtj1tal and pdrtj2tal can be obtained by first solving equation (14) for $V_{freefall}$:

$$V_{freefall} = \frac{dP/dt}{dP/dH}$$

Figure 64:
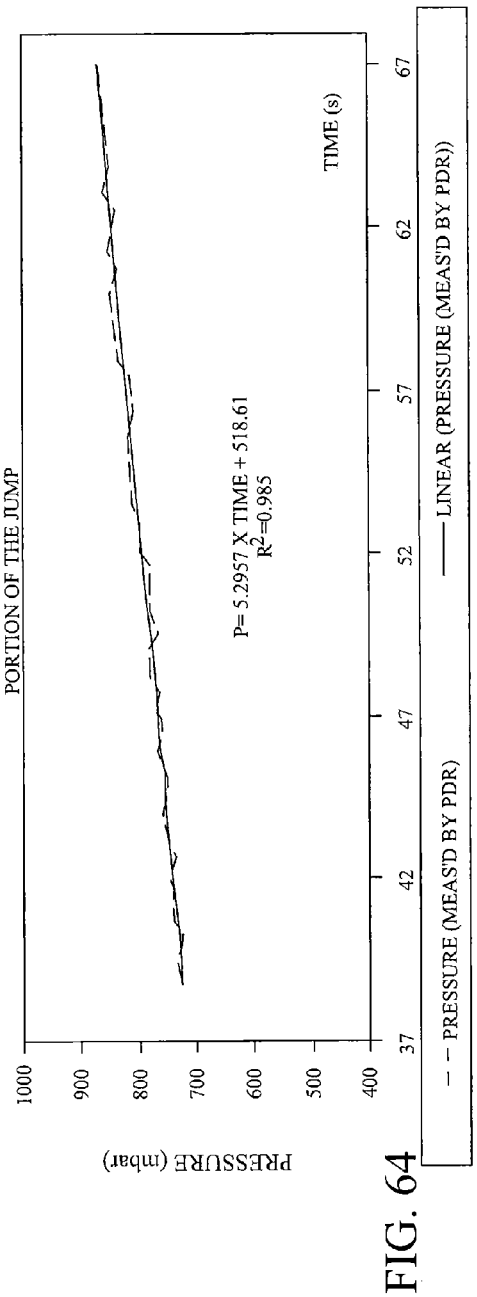
FIG. 64 shows the PDR device pressure data output during one jump.
Figure 65:
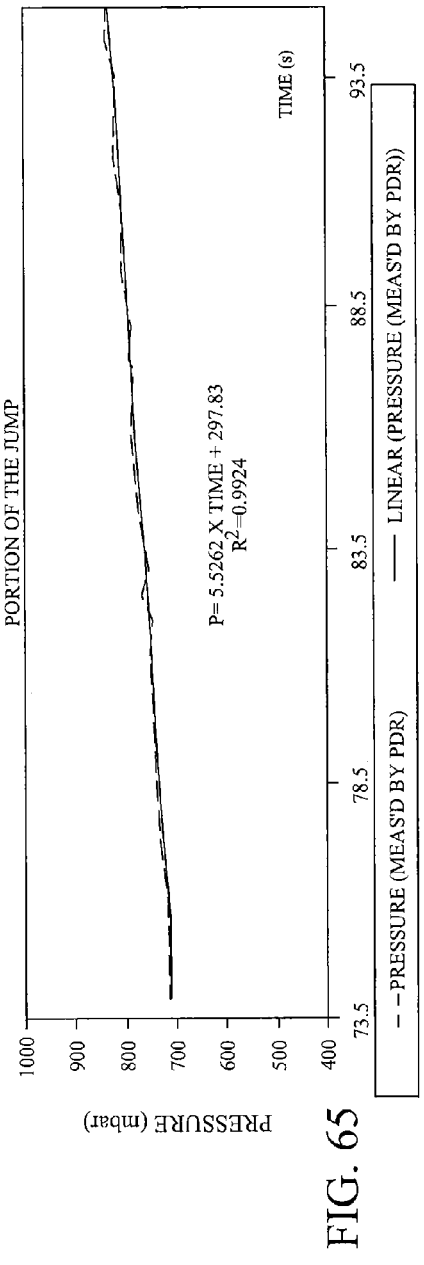
FIG. 65 shows the PDR device pressure data output from another jump.

Equations (15) and (16) are then used to get dP/dH, again in lieu of actual meteorological data. Here dP/dt is obtained from the PDR pressure readings, i.e., by calculating the slope of the pressure vs. time curve. In FIGS. 64 and 65, the slope (during free-fall) is remarkably constant and so dP/dt has the same value during the entire stage namely, 5.2957 mbar/s (pdrtj1tal) and 5.5262 mbar/s (pdrtj2tal). The difference between both slopes arose from the jumper wearing different jumpsuits, i.e., a "slow" (or loose) suit during pdrtj1tal and a "fast" (or tight) suit during pdrtj2tal. The computations (versus altitude) are shown in FIG. 66, with the fall speeds at deployment time (3000 to 4000 ft) evaluated at 159 ft/s and 166 ft/s, i.e., values that are in agreement with the published free-fall data.

Other test jumps were performed with a full tactical support package as shown in FIGS. 67 and 67a.

Each parachutist 500a carried either two PDRs 310 or one PDR 310 plus a smartphone for verification purposes. The PDR 319 unit was installed in the AR-2 pouch located on the left side of the MC-4 (365 cubic inches) parachute system as shown in FIGS. 67 and 67a. This location was used because the AR-2 pouch is close to the subject's center of gravity. The PDR was also rotated by approximately −60° on the z-axis, which requires a rotation transformation for correction. For each test, the PDR devices were activated and deactivated at the training facility, which captured the following events:

Travel to Airfield

Aircraft Motion (ascend, cruise)

Parachute Motion (jump from the aircraft; free-fall; parachute deployment and opening; descent and landing)

Travel to Facility

The tables below summarize the test subjects and jumps performed during the two days at YPG.

TABLE 23

YPG Subject Details

| Subject | PDR Devices | Jumper ID | Weight (lbs) | Height (in) |
|---|---|---|---|---|
| 1 | 4.6, 4.10 | Jumper 1 | 320/297 | 74/73 |
| 2 | 4.6, 4.10 | Jumper 2 | 350 | 68 |
| 3 | 4.7, Android | Jumper 3 | 340 | 71 |

TABLE 24

YPG Jump Details

| Test | Type | Date | Time (pacific) | Altitude (ft) | Approx. Free-Fall Duration (sec) |
|---|---|---|---|---|---|
| Jump1 | HAHO | Apr. 9, 2013 | 8 am | 10,000 | 4 |
| Jump2 | HAHO | Apr. 10, 2013 | 8 am | 17,000 | 4 |
| Jump3 | HAHO | Apr. 10, 2013 | 1 pm | 12,500 | 4 |

For each jump, the subjects performed similar tasks such as deploying from the back of the aircraft, free-falling for ~4 seconds and maneuvering to a targeted landing zone. The following sections provide a detailed analysis of the data collected in this test.

Figure 68:
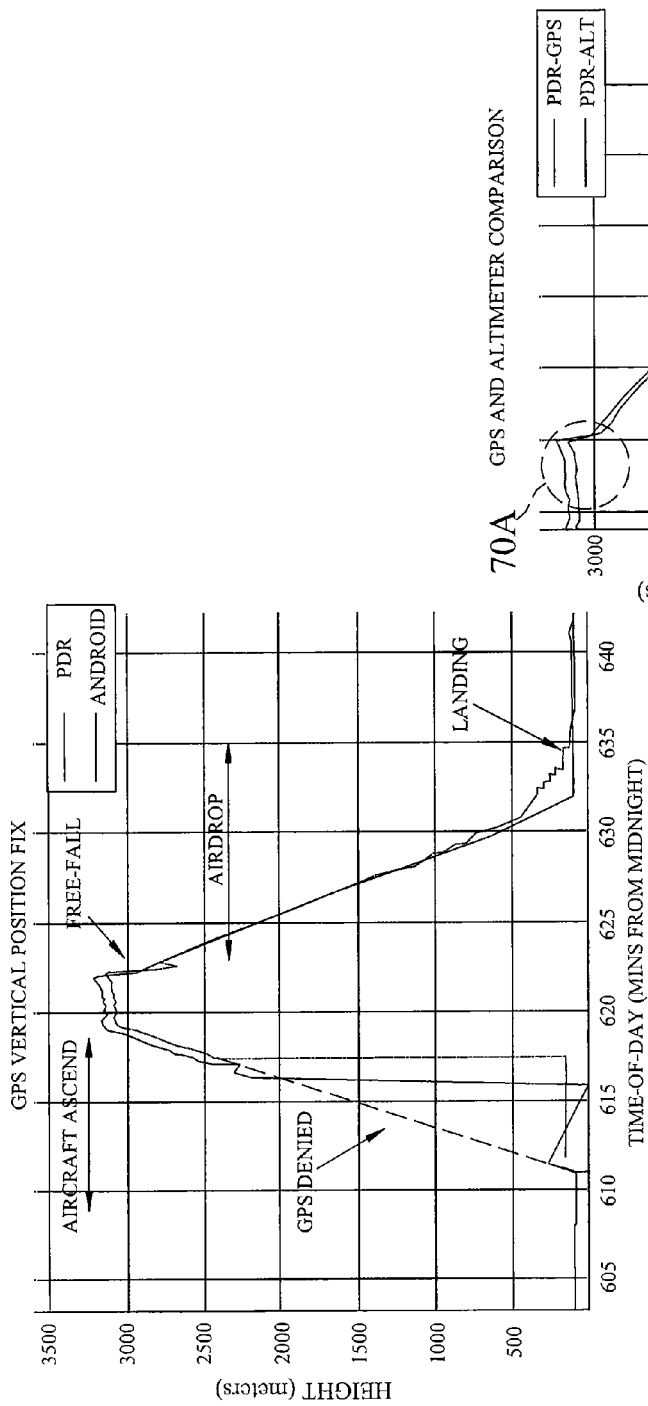
FIG. 68 shows altitude measurements as compared between the GPS on the PDR device and an android device on one of the test jumps.

As described in Table 23, a PDR device was paired with an Android phone to verify and compare GPS performance during the airdrop. The devices were located on the side of the subject (AR-2 pouch), which provided excellent reception. In addition, the aircraft was equipped with a GPS repeater, which allowed the GPS to maintain lock prior to deployment. The recorded GPS altitude data for the PDR and Android device is shown in FIG. 68. The plot illustrates and verifies the subject's altitude profile throughout the scenario. The maximum error between the two devices is about 80 meters, and both devices lost GPS lock during the aircraft ascend phase.

Figure 69:
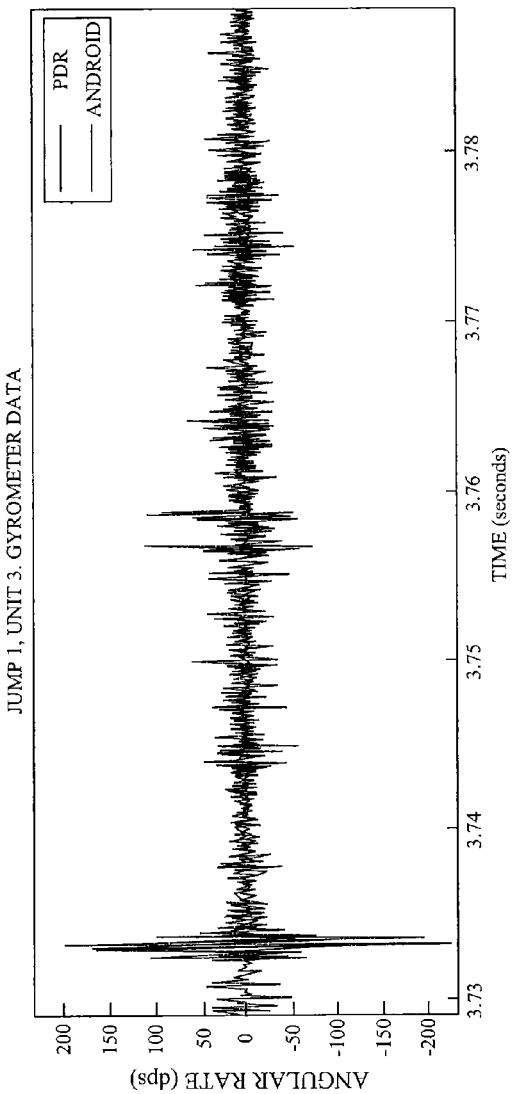
FIG. 69 is a comparison of recorded gyrometer angular data for the PDR device and an android device for the jump associated with FIG. 68.
Figure 70A:
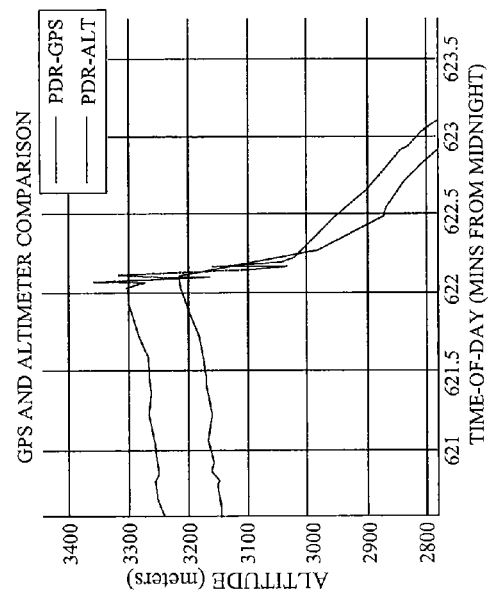
FIG. 70A shows an enlarged area of the comparison between GPS and altimeter for the area indicated in FIG. 70.

The data collected by the PDR device and the smartphone can also be verified through gyrometer data. The recorded gyrometer angular rate data for the PDR and Android device is shown in FIG. 69.

The plot verifies the correctness of the PDR gyrometer data by comparing it with the Android device gyrometer data. Both sets of gyrometer data show similar trends.

Figure 70:
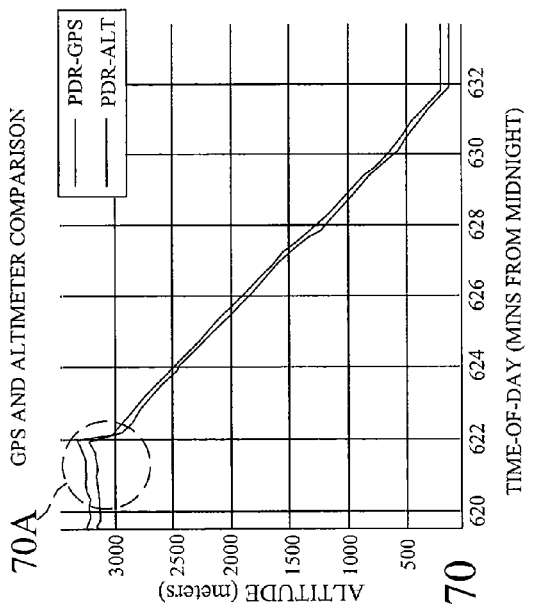
FIG. 70 is a comparison of the GPS and altimeter data for one test jump.

The graphs in FIG. 70 and A compare the estimated altitude between the PDR's GPS and altimeter sensor. The measured atmospheric pressure is converted to meters by using equation (1), which assumes a constant sea-level pressure of 1013.25 mbar.

The maximum error between the GPS and altimeter is approximately 90 meters, and both devices captured an accurate descent rate during the airdrop. The altimeter measured anomalies in the air pressure during free-fall, which is caused by air pressure variations around the subject during flight.

Figure 71:
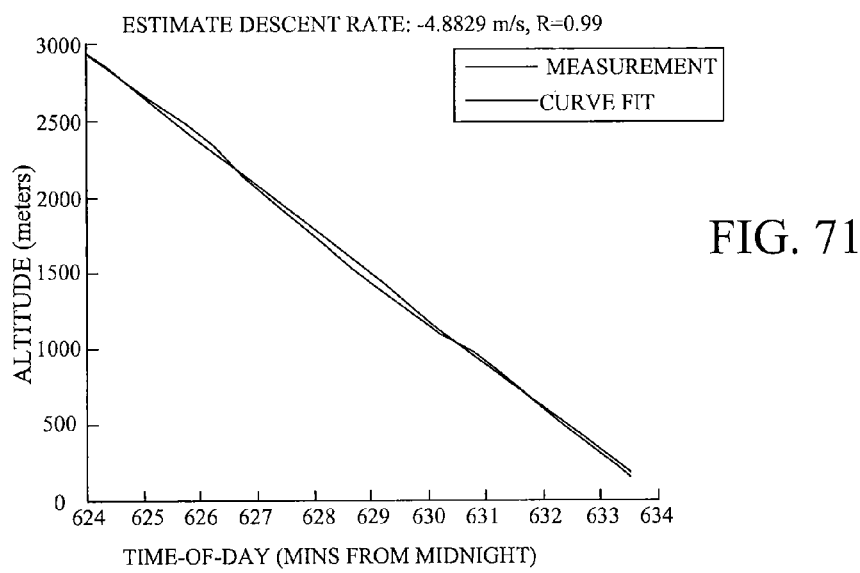
FIG. 71 is a graph showing descent rate calculated from the altimeter for one of the test jumps.

The graph in FIG. 71 shows the descent rate calculated from the altimeter for subject1/jump1. The descent rate is estimated by curve fitting a linear line to the estimated altitude as shown in FIG. 71. The estimated average descent rate is −4.88 m/s.

Figure 72:
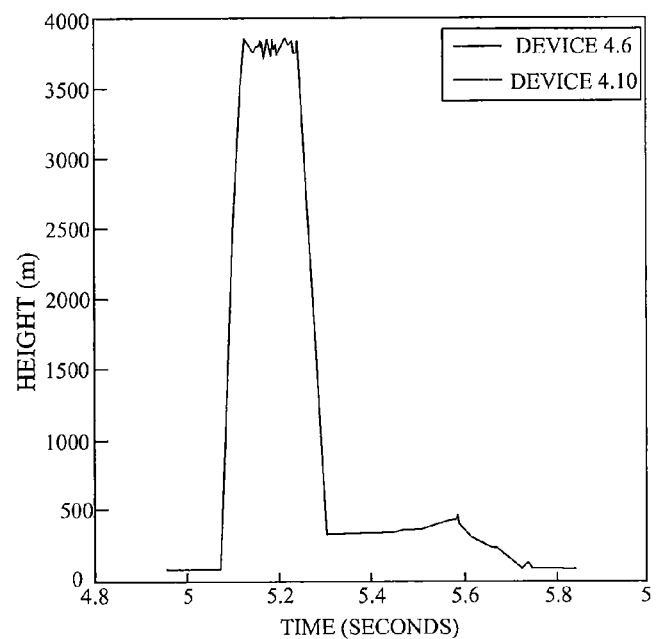
FIG. 72 shows a graph data of altitude comparison for two PDR devices carried by a parachutist in a test jump.
Figure 72A:
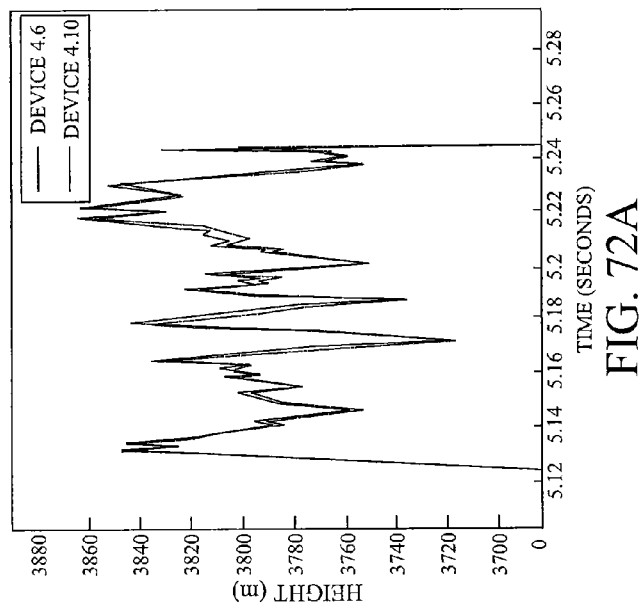
FIG. 72A is an enlarged view of the peak altitude portion of the graph from FIG. 72.

The recorded altimeter data for PDR 310 Unit 2, Devices 4.6 and 4.10 is shown in FIGS. 72 and 72A (the right graph is a zoomed in version of the left). These plots verify the correctness of the pressure data by comparing measurements across PDR devices. These signals are so closely aligned that any differences between the signals can only be seen in the zoomed in plot.

Figure 73:
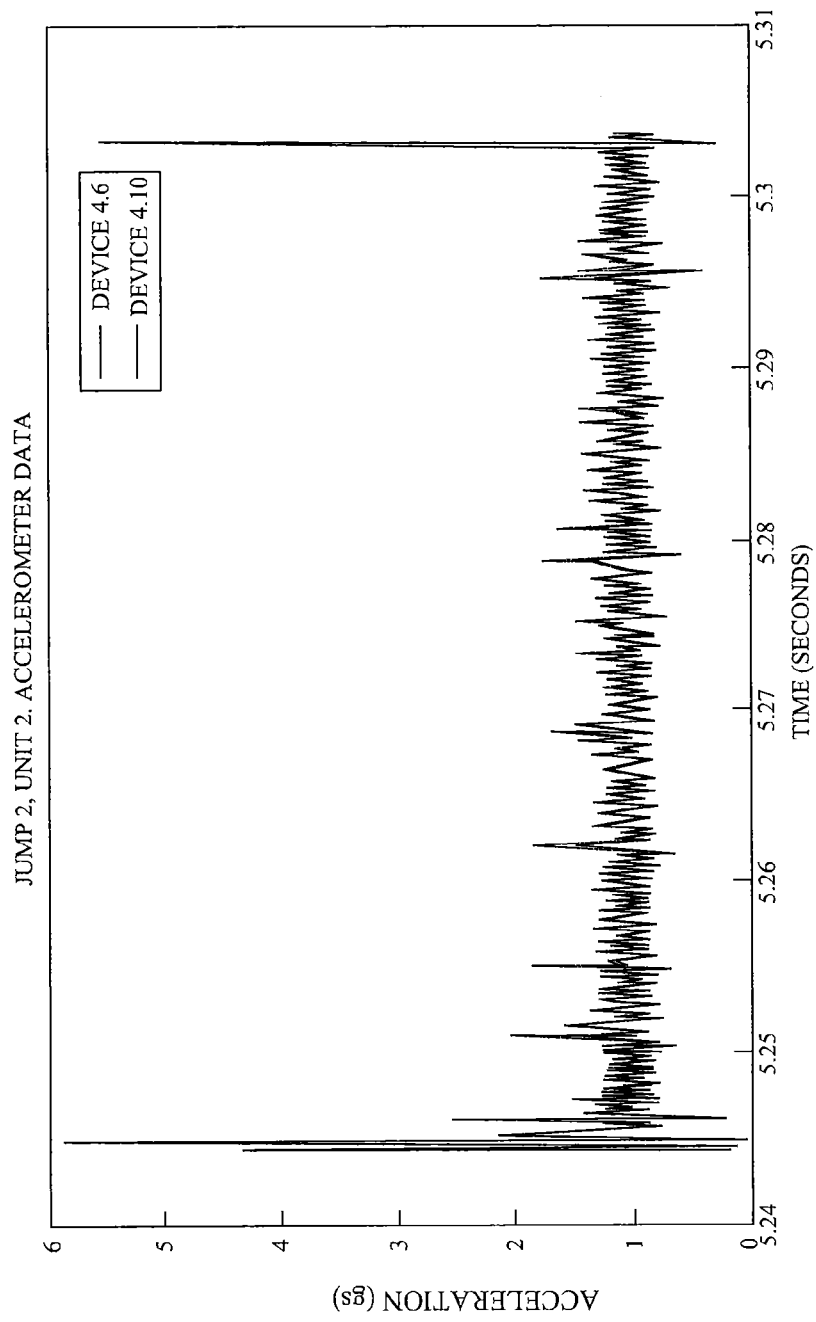
FIG. 73 shows recorded accelerometer data comparing to measurements taken by two different PDR devices.

The recorded accelerometer data for PDR 310 Unit 2, Devices 4.6 and 4.10 is shown in FIG. 73. This plot verifies the correctness of the accelerometer data by comparing measurements across PDR devices. Acceleration shown is the sum of the squares to account for axes misalignment. The standard deviation of the difference between the signals is 0.205 g-forces. This is mostly due to a slight time misalignment, as a visual inspection of the data shows extremely similar results between the two devices.

Figure 74:
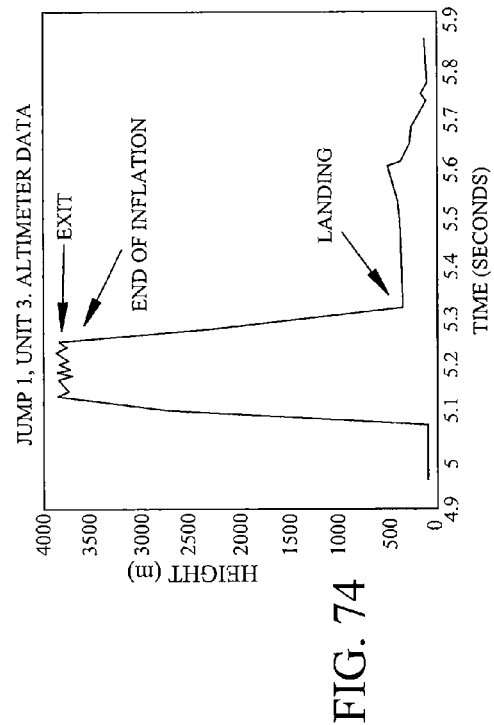
FIG. 74 is a graph of altimeter data from the PDR device during one test jump.
Figure 74A:
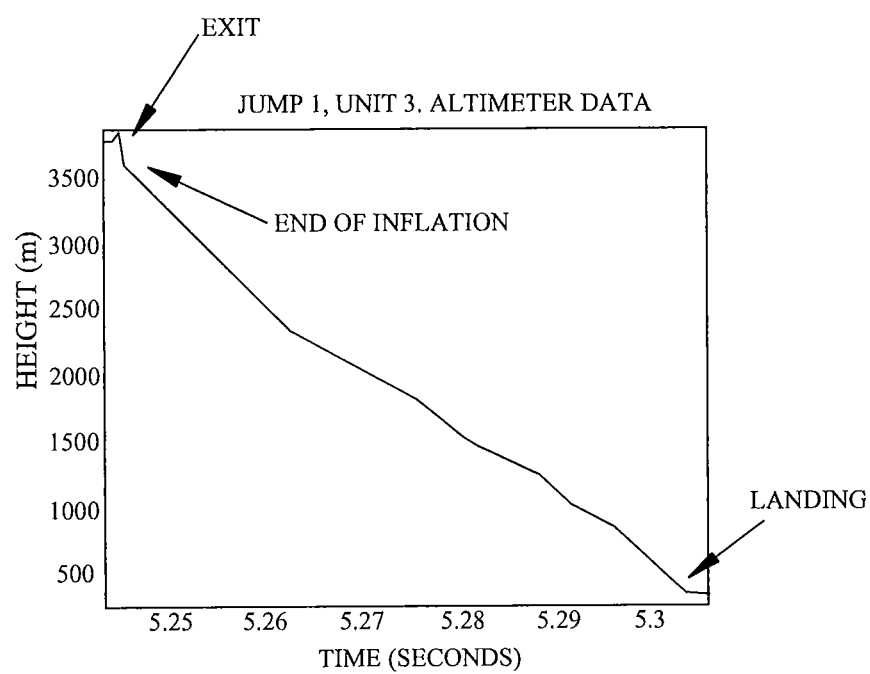
FIG. 74A is an expanded view of the accelerometer graph of FIG. 74 between exit of a parachutist to landing.

The altimeter data can be used to identify key events during the flight. Patterns in the data, along with data characteristics like maximum, minimum, and slope, are used to find the times of exit, the end of parachute inflation, and landing. These event marker times are used to calculate the time span of free-fall, deployment/inflation, and descent along with the descent rate (using the height information). These times can also then be applied to the data from the other sensors to identify data characteristics during different events. The recorded altimeter data for Jump 1, Unit 3 is shown in FIGS. 74 and 74A. The identified event markers have been automatically detected by the post-processing software.

The accelerometer data is processed for the period of time between exit from the plane and landing, as identified by the altimeter data processing. This data can then be examined for significant events and data patterns.

Figure 75:
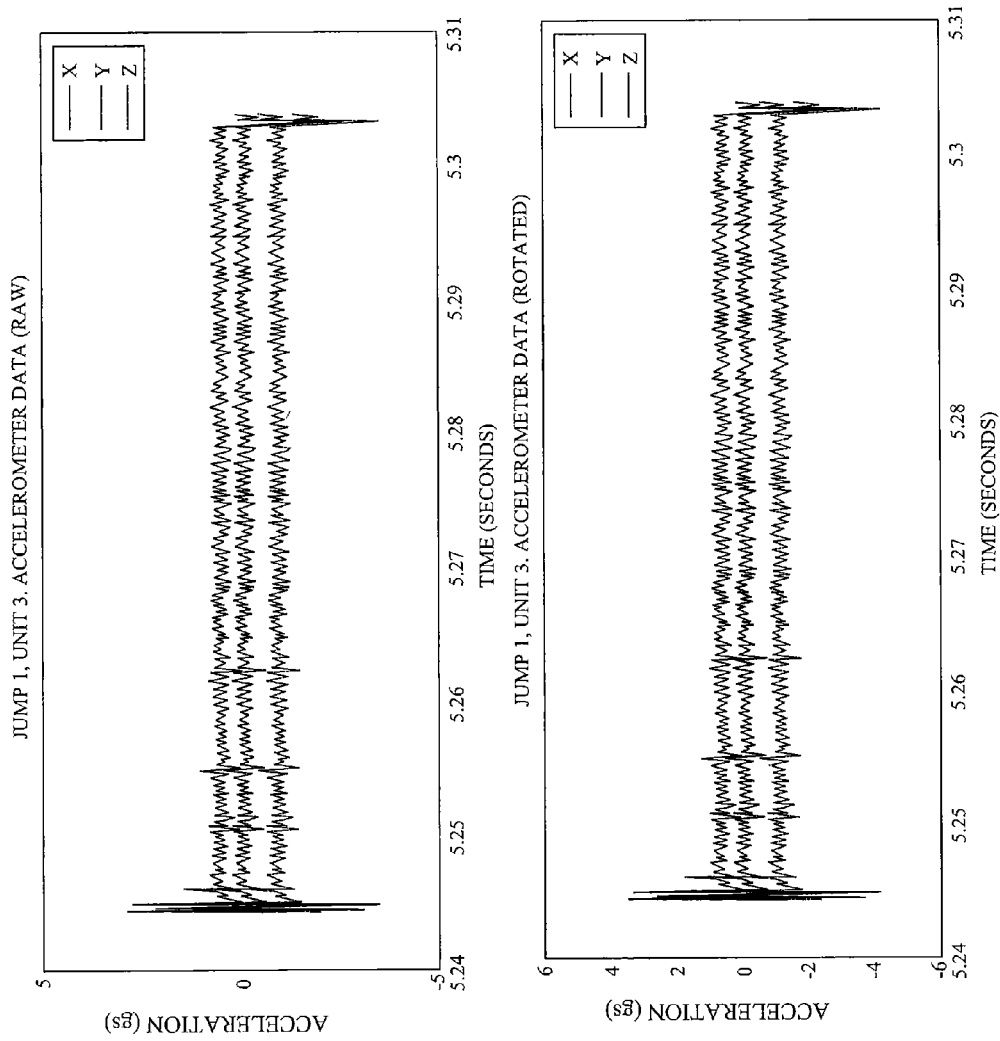
FIG. 75 is a graph of acceleration data output in a raw form compared with the Y axis rotated to be vertical.

Before using the acceleration data, the axes are automatically transformed from their frame relative to the jumper so that they align with an absolute coordinate system in which the y-axis points towards the sky. This transformation for data from Jump 1 Unit 3 can be seen in FIG. 75.

This data visually aligns with expectations for the jumper's acceleration. The big spike at the beginning is free-fall and parachute deployment. The spike at the end is when the jumper lands on the ground. As expected, for the entire middle period, the y-axis shows −1 g of acceleration and the x-axis and z-axis show almost zero acceleration. This confirms that the y-axis is pointing up as the jumper descends.

Figure 76:
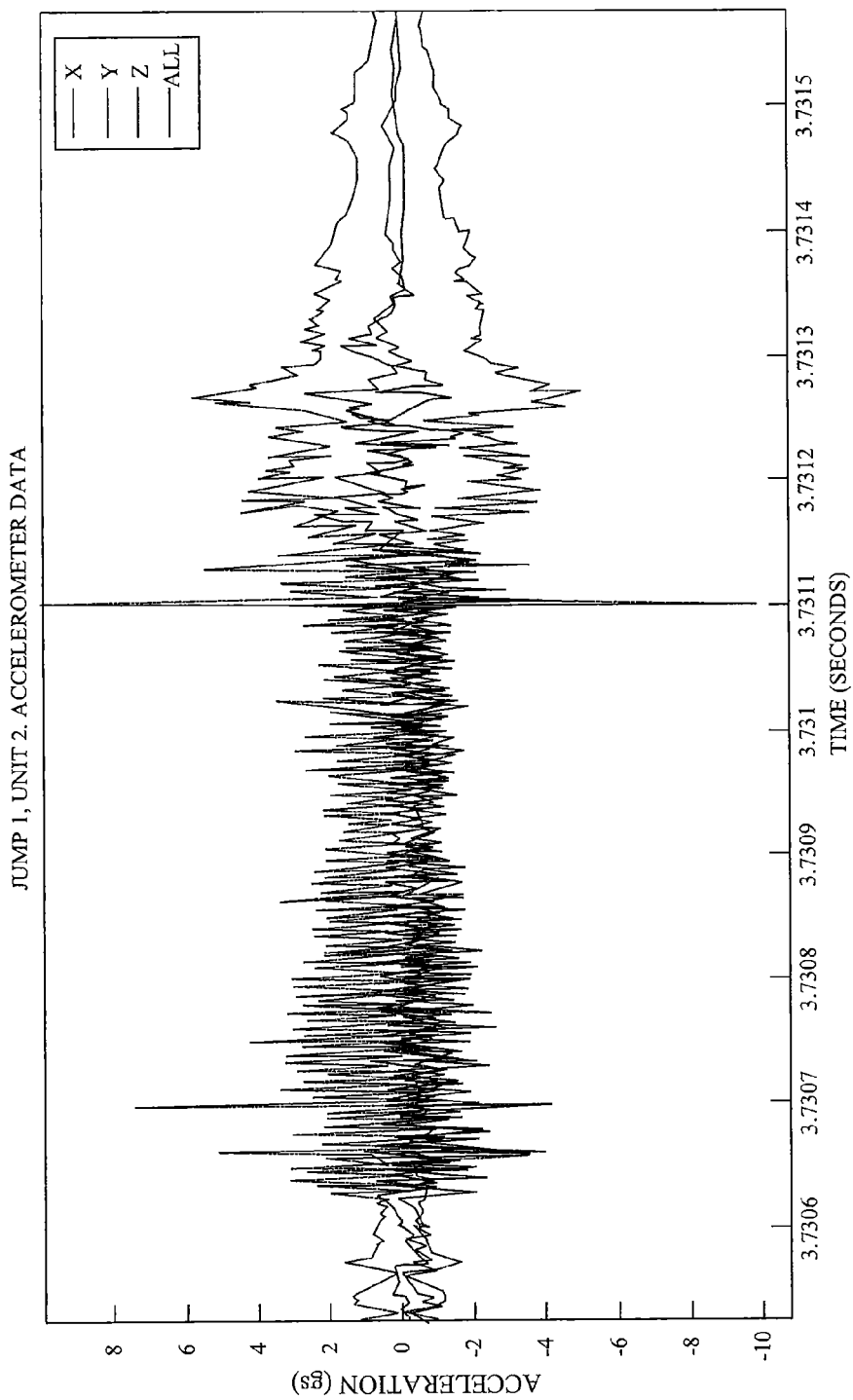
FIG. 76 is a graph of accelerometer data output from the PDR device during one of the test jumps during the time between when the parachutist exits the plane and the chute is deployed.

The accelerometer data from the period of plane exit through parachute inflation can then be examined to determine the force felt by the jumper. A zoomed-in version of the accelerometer data for Jump 1 Unit 2 during this period of time can be seen in FIG. 76.

Different events can easily be identified through the differences in acceleration. The maximum force for a given axis will be experienced in the y-axis due to the jumper's 500, 500a orientation at the time of parachute 502, 502a deployment. This maximum acceleration is automatically detected by software processing, which in this case is 8.192 Gs. This equates to $$F_{inflation} = mA \qquad (17)$$
$$F_{inflation} = \left(\frac{158.7[\text{kg}]}{1[\text{g-force}]}\right)(8.192*[\text{g-force}]*9.8[\text{m/s}\wedge 2])$$
$$F_{inflation} = 12740\text{N}$$

where 158.7 is the weight of Subject 2 in kg and g-forces are converted to meters/squared second.

Figure 77:
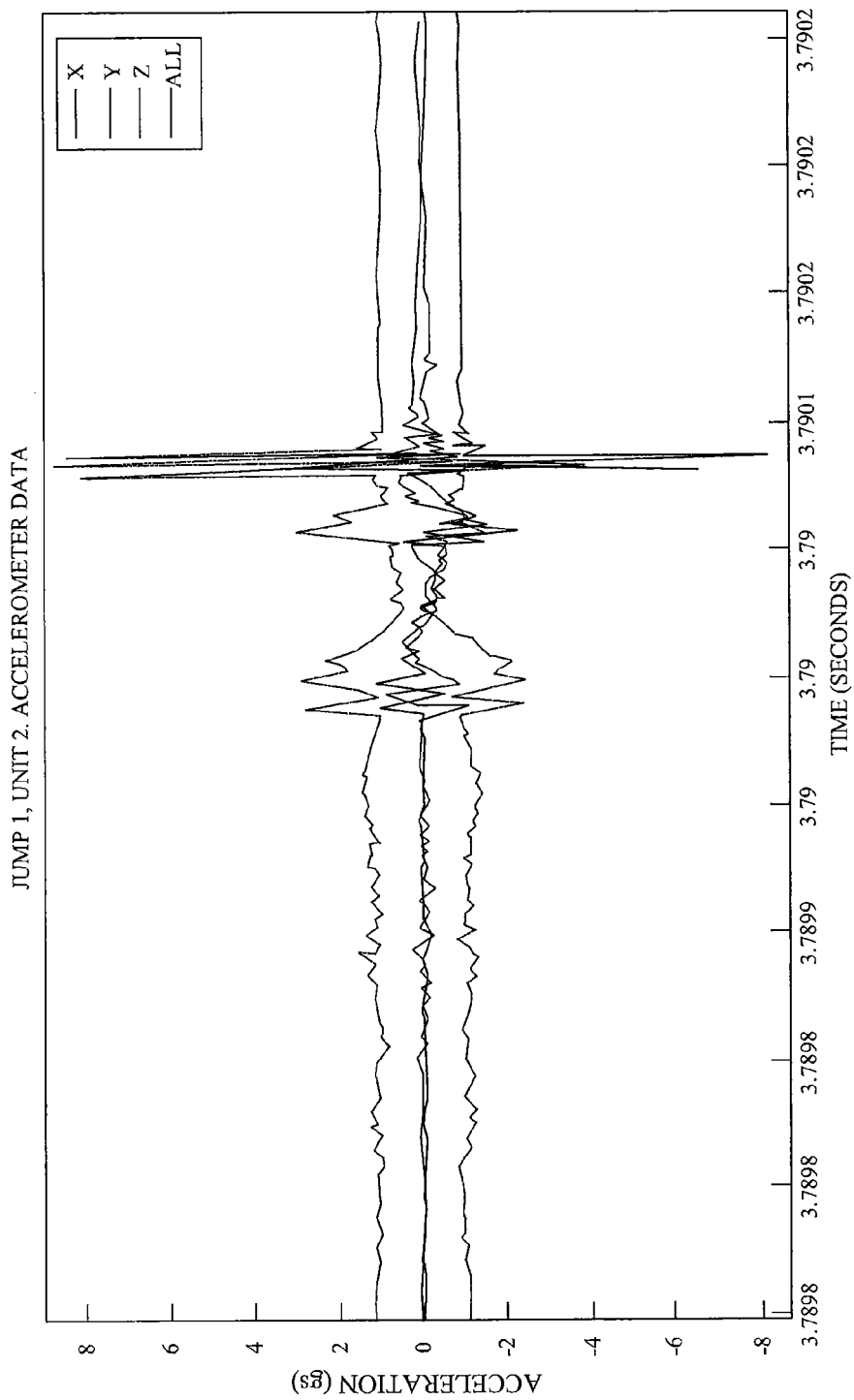
FIG. 77 is a graph of accelerometer data output from the PDR device during the landing of a test jump.

A similar analysis can be done for the landing. A zoomed-in version of the accelerometer data for Jump 1 Subject 2 during this period of time can be seen in FIG. 77.

The maximum force for a given axis will be experienced in the y-axis due to the jumper's orientation at the time of parachute deployment. In this example, landing is identified at a time of 37900 seconds, which is the first time the acceleration in the y-axis exceeds 2 gs since the start of the descent. The two additional spikes are likely due to gear and landing and motions of the jumper post-landing. The acceleration force is automatically detected by software processing, which in this case is 2.35 Gs. This equates to $$F_{inflation} = mA \qquad (18)$$
$$F_{inflation} = \left(\frac{158.7[\text{kg}]}{1[\text{g-force}]}\right)(2.35*[\text{g-force}]*9.8[\text{m/s}\wedge 2])$$
$$F_{inflation} = 3654\text{N}$$

where 158.7 is the weight of Subject 2 in kg and g-forces are converted to meters/squared second.

Additional analysis can be done on this data to detect the average force felt by the jumper and the accumulated force felt by the jumper. This can be done for certain periods of time or over the entire duration of the jump.

The gyrometer data is processed for the period of time between exit from the plane and landing, as identified by the altimeter data processing. This data can then be examined for significant events and data patterns.

Figure 78:
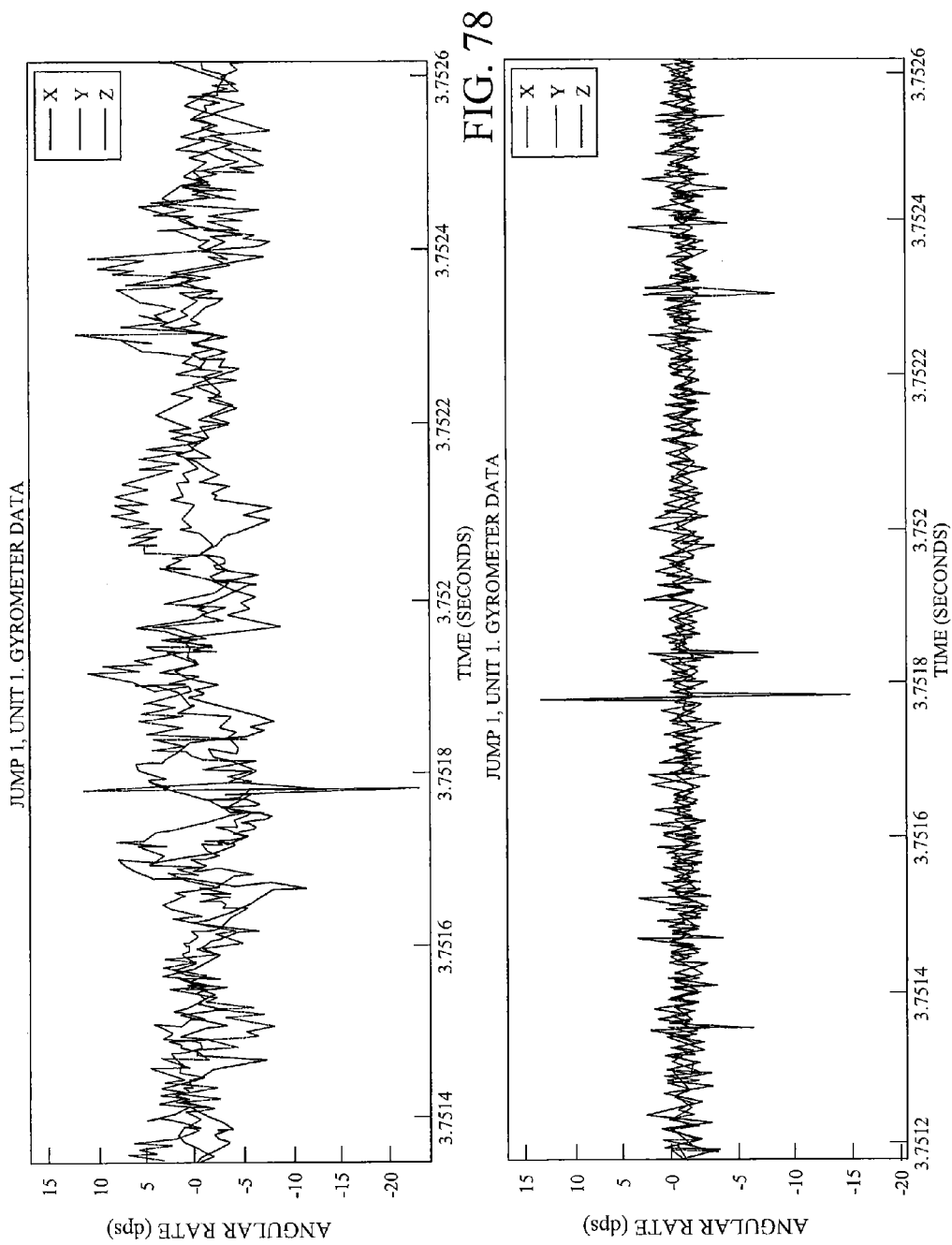
FIG. 78 shows comparison graphs of gyrometer data output from the PDR device of raw data versus high pass filter data for a test jump.

The gyrometer data for Jump 1 Subject 1 can be seen in FIG. 78. The top plot shows raw gyrometer data. As can be seen, this data is encumbered by slow oscillations around the various axes. This low frequency information is not representative of any significant jump characteristics and obscures the important gyrometer data. Therefore, this data is high-pass filtered before it is examined, leaving only the high frequency information.

The filtered gyrometer data for the middle portion of Jump 1 Subject 1 can be seen in FIG. 79. This data shows a relatively smooth flight for most of the descent. However, spikes can be seen every couple of minutes, identifying a point of high rotation. The spikes indicate the jumper 500a spinning, and can be isolated to get a count of the number of spins during a given period of time. Spikes are identified in the plot by the magenta and cyan dots. The ratio of spin count to time can be an indicator for the smoothness of the flight.

The same information can be viewed in FIG. 80, which shows the filtered gyrometer data for the free-fall and deployment/inflation part of the jump. Again, the magenta and cyan dots show the amount of time spent in a rotation greater than 20 dps. These identified times can be used as a count and a ratio (of spins to time). The angular rate can also be integrated over a duration of time to see the total rotation experienced by the jumper. These angular rate calculations and counts can be used for an assessment of smoothness or how smooth the jump was overall (or for certain duration of time).

A jump in which the reserve parachute had to be deployed (hereafter referred to as "Reserve Parachute Jump") shows very different patterns from normal deployments. In a typical jump, major changes in vertical velocity (the derivative of the height measurements from the altimeter) occur immediately after exiting the aircraft. The vertical velocity spikes at around −2 (arbitrarily normalized units for comparison). Then after a major spike it becomes constant at some negative magnitude (for the period of descent). At the end of the descent, vertical velocity returns to zero. A plot of vertical velocity can be seen in FIG. 81.

Figure 81:
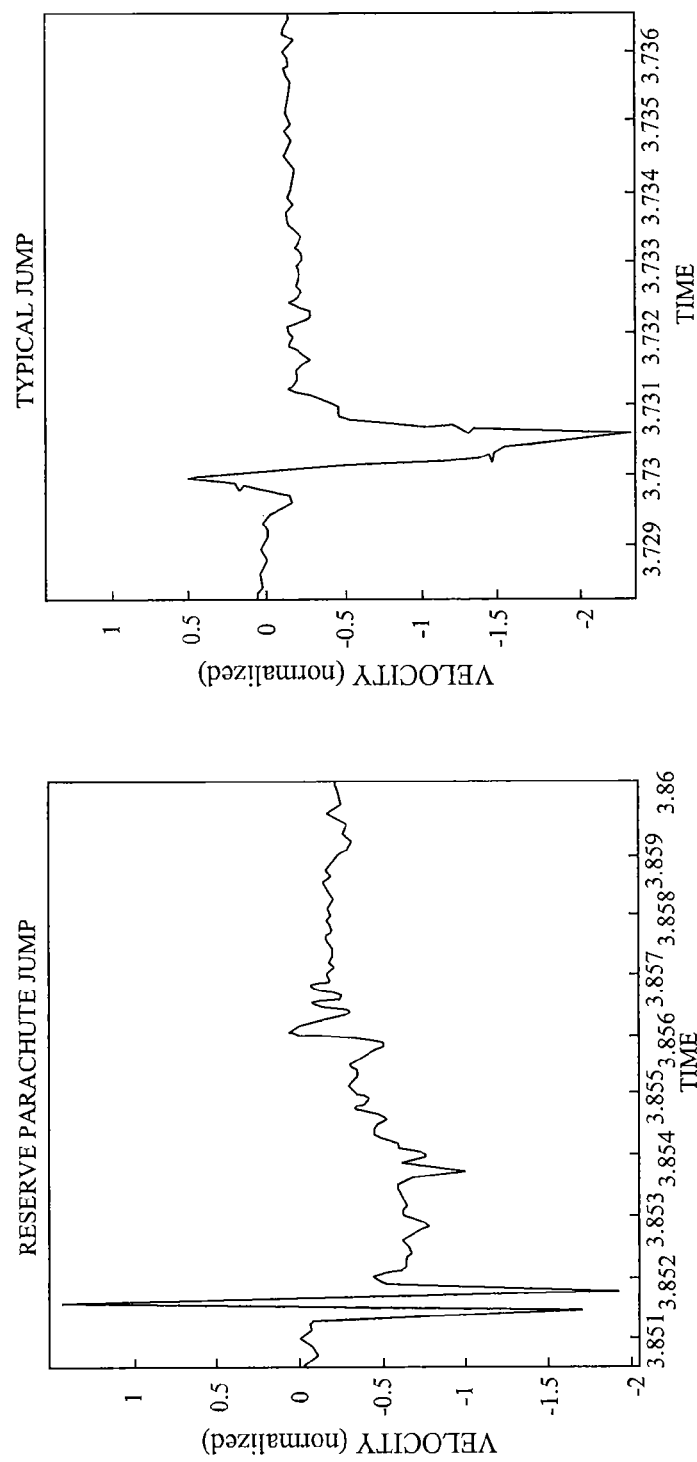
FIG. 81 is a graph of vertical velocity comparisons after exiting an aircraft when using a reserve parachute as compared to a typical jump.

In the plot on the right of FIG. 81 of a typical jump, the data is as expected. The velocity spikes one time and then quickly becomes constant at around −0.2, indicating stable descent. In the plot on the left of FIG. 81 of the Reserve Parachute Jump, multiple velocity spikes precede a period of abnormally fast descent. The velocity doesn't stabilize until almost 50 seconds in, as opposed to other "normal" jumps where the velocity stabilized in 10-20 seconds.

In a typical jump, there are major fluctuations in acceleration observed across all axes for the first 4-5 seconds post-jump during free fall. Then for about 2 seconds there are large spikes in the y-axis (which points up during descent) during parachute deployment and inflation. After parachute inflation, the acceleration is observed to quickly stabilizes, with the y-axis at −1 g and the x and z axes at 0 g. This whole process takes about 7 seconds.

Figure 82:
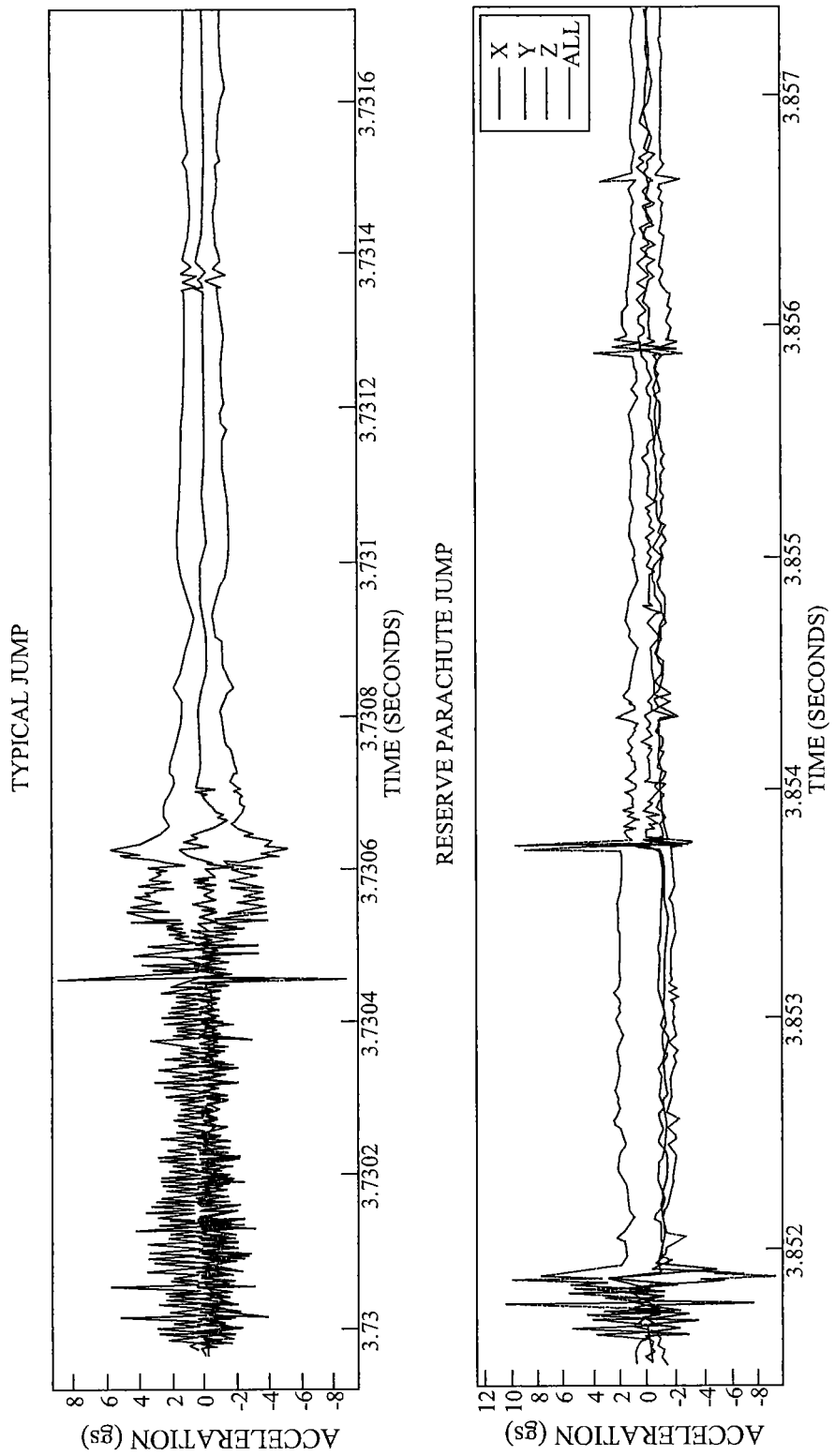
FIG. 82 is a graph of acceleration data for a typical jump compared to a reserve parachute jump.

A plot of jump acceleration can be seen in FIG. 82. In the upper plot of a typical jump, the data is as expected. Free-fall, from the time of jump (37,300 seconds) to the time of parachute inflation (37,304.5), lasts 4.5 seconds. Parachute deployment inflation (from 37,304.5 to 37,306.5 seconds) lasts 2 seconds. Within the next few seconds, the acceleration has stabilized and everything is as expected.

In the lower plot of the Reserve Parachute Jump, there is the expected initial area of free fall and deployment lasting around 7 seconds. However, there is then a period of about 15 seconds of relative stability in an unusual orientation. This is following by additional large acceleration spikes for another 30 seconds. The acceleration doesn't reach normal descent levels until about 50 seconds post jump.

In a typical jump, there are major fluctuations in rotation across all axes for the first 7 seconds during free fall and parachute deployment/inflation. All rotations then stabilize for the remainder of descent with spikes every 20 seconds or so due to assumed intentional jumper spins.

Figure 83:
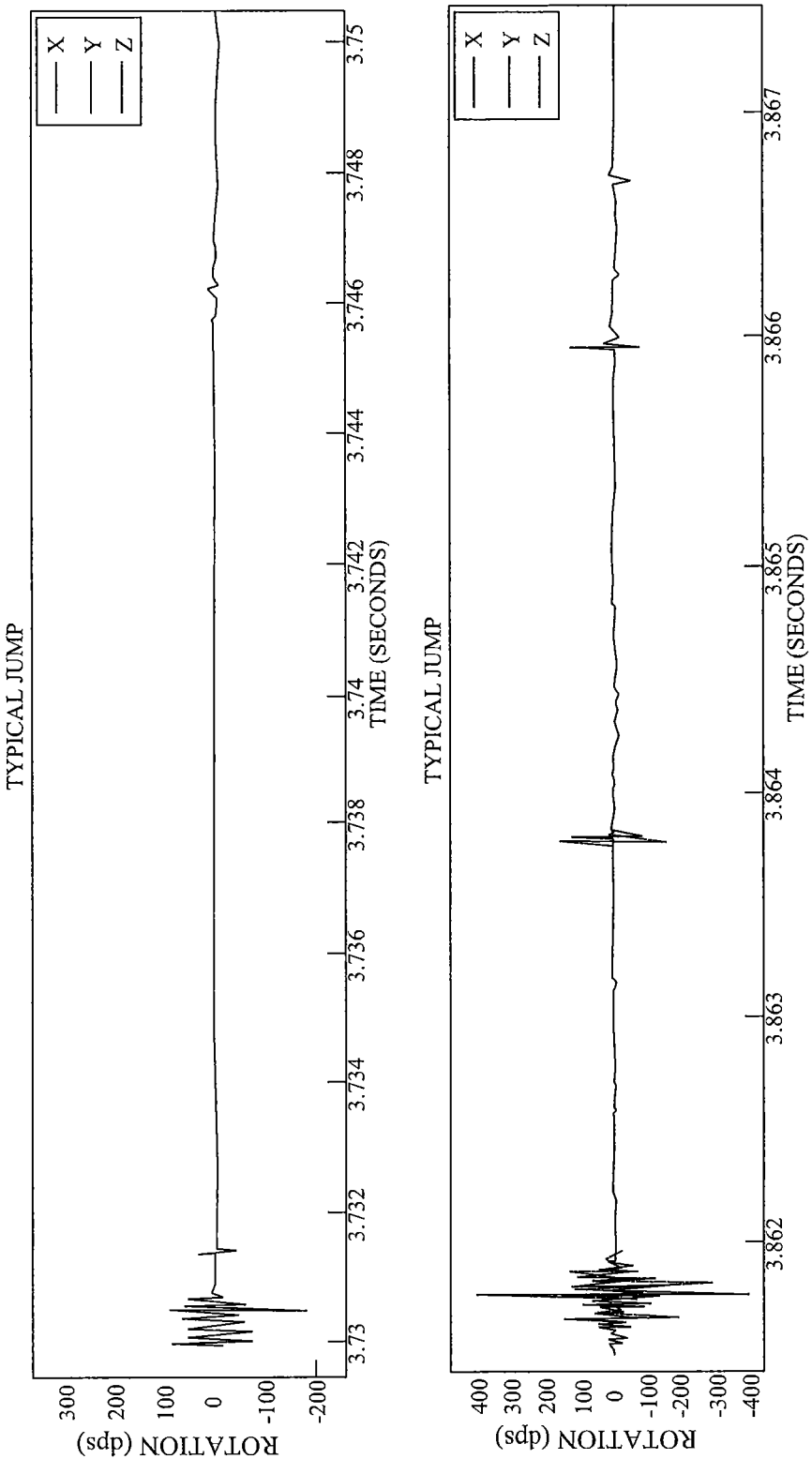
FIG. 83 is a graph of the comparison of rotation data from a typical jump as compared to a reserve parachute jump.

A plot of jump rotation can be seen in FIG. 83. In the upper plot of a typical jump, the data is as expected. Major spikes in rotation occur within the first 7 seconds post jump. Within the next few seconds, rotation has essentially ceased.

In the lower plot of the Reserve Parachute Jump, major events can be seen in the rotation data for the duration of the first 50 seconds post jump. The initial 7 seconds of rotation are followed by two additional periods of activity in which rotation exceeds 100 dps, a rate much higher than normal for post inflation rotation.

Typical maximum forces on the jumper were usually in the range of 4-6Gs during parachute inflation, with one instance as high as 8.5 Gs. In the Reserve Parachute Jump, initial force went as high as 9.3G. What is unusual is the multiple later occurrences also reaching over 4 Gs (on at least 3 separate occasions), indicating larger loads than should be expected.

While the invention has been taught with specific reference to these embodiments, one skilled in the art will recognize that changes can be made in form and detail without departing from the spirit and scope of the invention.

The invention claimed is:

1. A parachute data recorder system comprising:
a housing, said housing including a seal for resistance to moisture and environmental impact;
a plurality of sensors mounted in said housing, including an accelerometer, an altimeter, a gyrometer, GPS, and a second accelerometer, one of said accelerometers being a low-g accelerometer sensitive to a range including expected average acceleration and the other being a high-g accelerometer with a range including expected peak acceleration;
wherein a high end of said high-g accelerometer with a range including expected peak acceleration is at least two times that of a high end of the range of the low-g accelerometer sensitive to a range including expected average acceleration;
a microprocessor mounted in said housing for recording and processing data from said sensors;
a wireless connection unit mounted in said housing for transmitting data in said microprocessor; and
an electronic connection port.

2. The parachute data recorder system as set forth in claim 1, wherein initiation of recording is started by stress or strain inducement from parachute deployment.

3. The parachute data recorder system as set forth in claim 1, including an interface configured to support recording information including a parachute rigger's identification, date and serial number for both primary and secondary parachutes as well as jumper identification, aircraft type, date of jump, jump location, parachute harness type, equipment configuration, jumper weight, and jump master inspection.

4. The parachute data recorder system as set forth in claim 1, wherein said housing includes a front cover and a rear cover mounted together with fasteners received in threaded apertures or threaded inserts in the apertures and one or more apertures is devoid of a fastener for receiving tie-offs to mount said housing.

5. The parachute data recorder system as set forth in claim 1 including a sealed cap covering the electronic connection port.

6. The parachute data recorder system as set forth in claim 1 further including a main control button including a tactile switch wherein pressing and holding the main button enables the system and wherein a subsequent quick push activates recording capabilities or pressing and holding the button disables the system.

7. The parachute data recorder system as set forth in claim 1, further including an LED indicator, including four unique states including an idol status showing as a solid first color, a recording status wherein the first color is blinking, a busy status showing as a solid second color, and a solid third color indicating an unrecoverable system error.

8. The parachute data recorder system as set forth in claim 1, further including a strict power sequential sensing and initialization routine and inquiry whether a main button is pressed wherein recording is enabled or if USB is attached to said electronic connection port, to connect the unit to a mass-storage device driver or enable wireless connection.

9. A parachute data recorder system comprising:
a housing, said housing including a seal for resistance to moisture and environmental impact;
a plurality of sensors mounted in said housing, including an accelerometer, an altimeter, a gyrometer, and a GPS;
a microprocessor mounted in said housing for recording and processing data from said sensors, said system calculates average and peak riser forces sustained during jumps;
a wireless connection unit mounted in said housing for transmitting data in said microprocessor; and
an electronic connection port.

10. A method of recording dynamic and static data for parachute jumps including the steps of:
providing a sensor and recording system including a sealed housing, sensors including a GPS, a low-g accelerometer sensitive to a range including expected average acceleration, a high-g accelerometer with a range including expected peak acceleration, an altimeter, and a gyrometer, and a microprocessor;
wherein a high end of the low-g accelerometer sensitive to a range including expected average acceleration is ±2 g's of the expected average acceleration, and a high end of the range of the high-g accelerometer with a range including expected peak acceleration is ±2 g's of the expected peak acceleration;

inputting data related to a jump to be performed including a parachute rigger's identification, a date a parachute was packed, serial number of the parachute;

activating the unit prior to a jump;

said sensors recording dynamic jumping data relative to a parachute jump.

11. The method of recording dynamic and static data for parachute jumps as set forth in claim 10, further including the steps of selecting and holding a main control switch to power the system on, and quickly pushing the main control switch to activate recording capabilities.

12. The method of recording dynamic and static data for parachute jumps as set forth in claim 11, further including the step of pressing and holding said main control switch to disable said system.

13. The method of recording dynamic and static data for parachute jumps as set forth in claim 11, further including the step of initiating recording of sensor data by stress or strain inducement from parachute deployment.

14. The method of recording dynamic and static data for parachute jumps as set forth in claim 10, further including the steps of providing an interface to the sensor and recording system and recording information related to a parachute riggers identification, packing date, and serial number for both primary and secondary parachutes, jumper identification, aircraft type, date of jump, jump location, parachute harness type, equipment configuration, jump plate, or jump master inspection.

15. The method of recording dynamic and static data for parachute jumps as set forth in claim 10, including the steps of providing front and rear covers mounted together with fasteners and apertures, leaving one or more apertures devoid of a fastener, and using the apertures as tie-ons to mount said housing.

16. The method of recording dynamic and static data for parachute jumps as set forth in claim 10, further including the steps of providing an LED indicator, and indicating the unique states of the system using said LED indicator, wherein an idol status shows as a solid first color, a recording status shows with the first color blinking, a busy status shows as a solid second color, and an unrecoverable system error shows as a solid third color.

17. The method of recording dynamic and static data for parachute jumps as set forth in claim 10, including the step of calculating average and peak rise of forces sustained during jumps.

18. The method of recording dynamic and static data for parachute jumps as set forth in claim 10, further including the steps of transforming coordinate and axes of the sensor and recording system to other referenced frames coinciding with a jumper's center of gravity and on the ground.

19. The method of recording dynamic and static data for parachute jumps as set forth in claim 10, including the step of providing a wireless connection and web-based graphical user interface for tracking of inventory and uses of parachute equipment and for downloading data from the recording system.

* * * * *